US012672879B2

(12) United States Patent
Shi

(10) Patent No.: US 12,672,879 B2
(45) Date of Patent: Jul. 7, 2026

(54) CLIP APPARATUS

(71) Applicant: HANGZHOU AGS MEDTECH CO., LTD., Hangzhou (CN)

(72) Inventor: Baiming Shi, Hangzhou (CN)

(73) Assignee: HANGZHOU AGS MEDTECH CO., LTD., Hangzhou (CN)

( * ) Notice: Subject to any disclaimer, the term of this patent is extended or adjusted under 35 U.S.C. 154(b) by 225 days.

(21) Appl. No.: 18/693,145

(22) PCT Filed: Sep. 16, 2022

(86) PCT No.: PCT/CN2022/119233
§ 371 (c)(1),
(2) Date: Mar. 18, 2024

(87) PCT Pub. No.: WO2023/041011
PCT Pub. Date: Mar. 23, 2023

(65) Prior Publication Data
US 2024/0398423 A1 Dec. 5, 2024

(30) Foreign Application Priority Data

Sep. 18, 2021 (CN) .......................... 202111111648.2
Sep. 30, 2021 (CN) .......................... 202111162631.X
(Continued)

(51) Int. Cl.
*A61B 17/128* (2006.01)
*A61B 17/00* (2006.01)

(52) U.S. Cl.
CPC ..................... *A61B 17/1285* (2013.01); *A61B 2017/00473* (2013.01)

(58) Field of Classification Search
CPC ... A61B 17/083; A61B 17/10; A61B 17/1222; A61B 17/128; A61B 17/1285; A61B 2017/00473; A61B 2090/037
See application file for complete search history.

(56) References Cited

U.S. PATENT DOCUMENTS 2,256,382 A * 9/1941 Dole .................. A61B 17/0682
72/409.05
4,296,751 A * 10/1981 Blake, III ............ A61B 17/128
606/143
(Continued)

FOREIGN PATENT DOCUMENTS

CN 203328756 U 12/2013
CN 1.10393564 A 11/2019
(Continued)

OTHER PUBLICATIONS

Partial Supplementary European Search Report in European Application No. 22869378.4 mailed on Nov. 26, 2024, 14 pages.
(Continued)

*Primary Examiner* — Ryan J. Severson
(74) *Attorney, Agent, or Firm* — METIS IP LLC

(57) ABSTRACT

Embodiments of the present disclosure provide a clip apparatus. The clip apparatus may include a conveying device and a plurality of clip devices. The conveying device may include a sheath pipe provided with a passage. The plurality of clip devices are provided outside of the passage of the sheath pipe. The plurality of clip devices are releasably connected in sequence, and each of the plurality of clip devices is configured to clip tissue.

19 Claims, 40 Drawing Sheets

(30) Foreign Application Priority Data

| Nov. 11, 2021 | (CN) | ......................... 202111334658.2 |
| Jul. 28, 2022 | (CN) | ......................... 202210896808.7 |

(56) References Cited

U.S. PATENT DOCUMENTS

| 4,556,058 | A | * | 12/1985 | Green ................... A61B 17/128 |
| | | | | 606/174 |
| 4,612,932 | A | * | 9/1986 | Caspar ............... A61B 17/0682 |
| | | | | 606/143 |
| 4,671,278 | A | * | 6/1987 | Chin .................... A61B 17/128 |
| | | | | 606/143 |
| 5,192,288 | A | * | 3/1993 | Thompson ......... A61B 17/1285 |
| | | | | 606/143 |
| 5,464,416 | A | | 11/1995 | Steckel |
| 5,779,720 | A | * | 7/1998 | Walder-Utz .......... A61B 17/083 |
| | | | | 606/151 |
| 6,719,767 | B1 | * | 4/2004 | Kimblad .............. A61B 17/064 |
| | | | | 606/151 |
| 7,011,667 | B2 | * | 3/2006 | Kobayashi ......... A61B 17/1285 |
| | | | | 606/139 |
| 7,011,669 | B2 | * | 3/2006 | Kimblad .............. A61B 17/064 |
| | | | | 606/151 |
| 7,223,271 | B2 | * | 5/2007 | Muramatsu ........ A61B 17/1285 |
| | | | | 606/139 |
| 7,879,052 | B2 | | 2/2011 | Adams et al. |
| 8,523,880 | B2 | * | 9/2013 | Kissel .................. A61B 17/083 |
| | | | | 606/232 |
| 10,188,383 | B2 | * | 1/2019 | Miraki ............... A61B 17/0485 |
| 10,729,448 | B2 | | 8/2020 | Patel et al. |
| 10,820,903 | B2 | * | 11/2020 | Randhawa ........... A61B 17/083 |
| 11,071,552 | B2 | * | 7/2021 | Saenz Villalobos ......................... A61B 17/1227 |
| 11,123,064 | B2 | * | 9/2021 | Chen .................... A61B 17/122 |
| 11,369,386 | B2 | * | 6/2022 | Wallace ................. A61G 13/04 |
| 11,583,293 | B2 | | 2/2023 | Menn et al. |
| 11,992,223 | B2 | | 5/2024 | Muyari et al. |
| 12,465,369 | B2 | | 11/2025 | Tsuji et al. |
| 2002/0128667 | A1 | * | 9/2002 | Kobayashi ......... A61B 17/1227 |
| | | | | 606/139 |
| 2002/0151916 | A1 | * | 10/2002 | Muramatsu ........ A61B 17/1227 |
| | | | | 606/158 |
| 2003/0153946 | A1 | * | 8/2003 | Kimblad .............. A61B 17/064 |
| | | | | 606/151 |
| 2004/0204724 | A1 | * | 10/2004 | Kissel ................ A61B 17/0487 |
| | | | | 606/151 |
| 2004/0249414 | A1 | * | 12/2004 | Kissel .................... A61B 17/10 |
| | | | | 606/221 |
| 2005/0216036 | A1 | * | 9/2005 | Nakao .................. A61B 17/083 |
| | | | | 606/139 |
| 2009/0318937 | A1 | | 12/2009 | Matsuoka et al. |
| 2014/0316440 | A1 | * | 10/2014 | Gordon ............... A61B 17/122 |
| | | | | 606/142 |
| 2016/0183937 | A1 | * | 6/2016 | Miraki .............. A61B 17/0485 |
| | | | | 606/232 |
| 2018/0078258 | A1 | | 3/2018 | Randhawa et al. |
| 2019/0167265 | A1 | | 6/2019 | Chen et al. |
| 2019/0231353 | A1 | | 8/2019 | Saenz Villalobos et al. |
| 2020/0008811 | A1 | | 1/2020 | Itoh et al. |
| 2020/0405317 | A1 | * | 12/2020 | Wallace ................. A61B 34/37 |
| 2022/0386856 | A1 | | 12/2022 | Shi et al. |
| 2023/0172616 | A1 | * | 6/2023 | Goldenberg ......... A61B 17/083 |
| | | | | 606/142 |
| 2024/0398423 | A1 | * | 12/2024 | Shi ..................... A61B 17/1285 |

FOREIGN PATENT DOCUMENTS

| CN | 211270957 U | 8/2020 |
| CN | 211355689 U | 8/2020 |
| CN | 212490043 U | 2/2021 |
| CN | 213406175 U | 6/2021 |
| JP | 2006087537 A | 4/2006 |
| JP | 5383222 B2 | 8/2010 |
| JP | 2014188344 A | 10/2014 |
| WO | 2015000561 A1 | 1/2015 |

OTHER PUBLICATIONS

International Search Report in PCT/CN2022/119233 mailed on Dec. 13, 2022, 8 pages.
Written Opinion in PCT/CN2022/119233 mailed on Dec. 13, 2022, 9 pages.
International Search Report in PCT/CN2022/122089 mailed on Dec. 21, 2022, 8 pages.
Written Opinion in PCT/CN2022/122089 mailed on Dec. 21, 2022, 6 pages.

* cited by examiner

320A

320B

<u>800, 850</u>

870

871

870

820 (830)

500

900

326

530

327

530

840

841

842

843

860

510

CLIP APPARATUS

CROSS-REFERENCE TO RELATED APPLICATIONS

This application is a U.S. national stage under 35 U.S.C. § 371 of International Application No. PCT/CN/2022/119233, filed on Sep. 16, 2022, which claims priority to Chinese patent Application NO. 202111111648.2, filed on Sep. 18, 2021, Chinese Patent Application NO. 202111162631. X, filed on Sep. 30, 2021, Chinese Patent Application NO. 202111334658.2 filed on Nov. 11, 2021, and Chinese Patent Application NO. 202210896808.7 filed on Jul. 28, 2022, the entire contents of each of which are hereby incorporated by reference.

TECHNICAL FIELD

The present disclosure relates to the field of medical apparatus, and in particular, to a clip apparatus.

BACKGROUND

Having existed for more than 50 years, and having gone through the stages from disease diagnosis to disease treatment, endoscopes have become very effective and reliable for the treatment of some diseases. The flexible endoscope has been widely used in the fields of the digestive, gynecological, urinary, respiratory, and cardiovascular due to its characteristics of not requiring surgical openings and being minimally invasive. At the same time, technical requirements of miniaturization, maneuverability, and high flexibility are set for the surgical instruments that are compatible with the flexible endoscope. The stomach and intestines of living organisms often experience bleeding, mucosal damage, or even perforation due to various diseases, accidents, or injuries during endoscopic diagnosis and treatment. In the clinic, bleeding can be stopped by mechanical compression with a clip device. The clip device can grasp the tissue around the wound and temporarily hold the wound edges together to close the wound, and it is also used for wound closure. However, existing clip devices commonly used in clinical procedures are single-shot clip devices (e.g., hemostatic clips), which require multiple changes of instruments for clipping and repositioning for large wounds or multiple bleeding points. This places a significant workload on surgeons, as repeated insertion and removal of hemostatic clips can consume a lot of time, leading to prolonged surgery and missing the optimal time for hemostasis, resulting in increased surgical risks due to significant bleeding in the gastrointestinal tract.

SUMMARY

One of the embodiments of the present disclosure provides a clip apparatus comprising a conveying device and at least two clip devices. The conveying device may include a sheath pipe provided with a passage and a core shaft extending axially within the passage of the sheath pipe. The at least two clip devices may include a first clip device and a second clip device. The first clip device and the second clip device may respectively include at least one clipping portion, the clipping portions may include a first clipping portion provided in the first clip device and a second clipping portion provided in the second clip device, and the clipping portions may be provided outside the passage of the sheath pipe.

According to the above-described scheme, the clip apparatus may be provided with different counts of clip devices, and a user may choose a clip apparatus provided with a suitable count of clip devices according to a size of a trauma of tissue to be stopped from bleeding as predicted in the surgery. The operation of clipping the tissue may be performed a plurality of times without repeated insertion, and clipping closure of large wounds or a plurality of bleeding points may be achieved in a shorter time, reducing surgical risks and costs.

BRIEF DESCRIPTION OF THE DRAWINGS

The present disclosure is further described in terms of exemplary embodiments. These exemplary embodiments are described in detail with reference to the drawings. These embodiments are non-limiting exemplary embodiments, in which like reference numerals represent similar structures throughout the several views of the drawings, and where.

Figure 1:
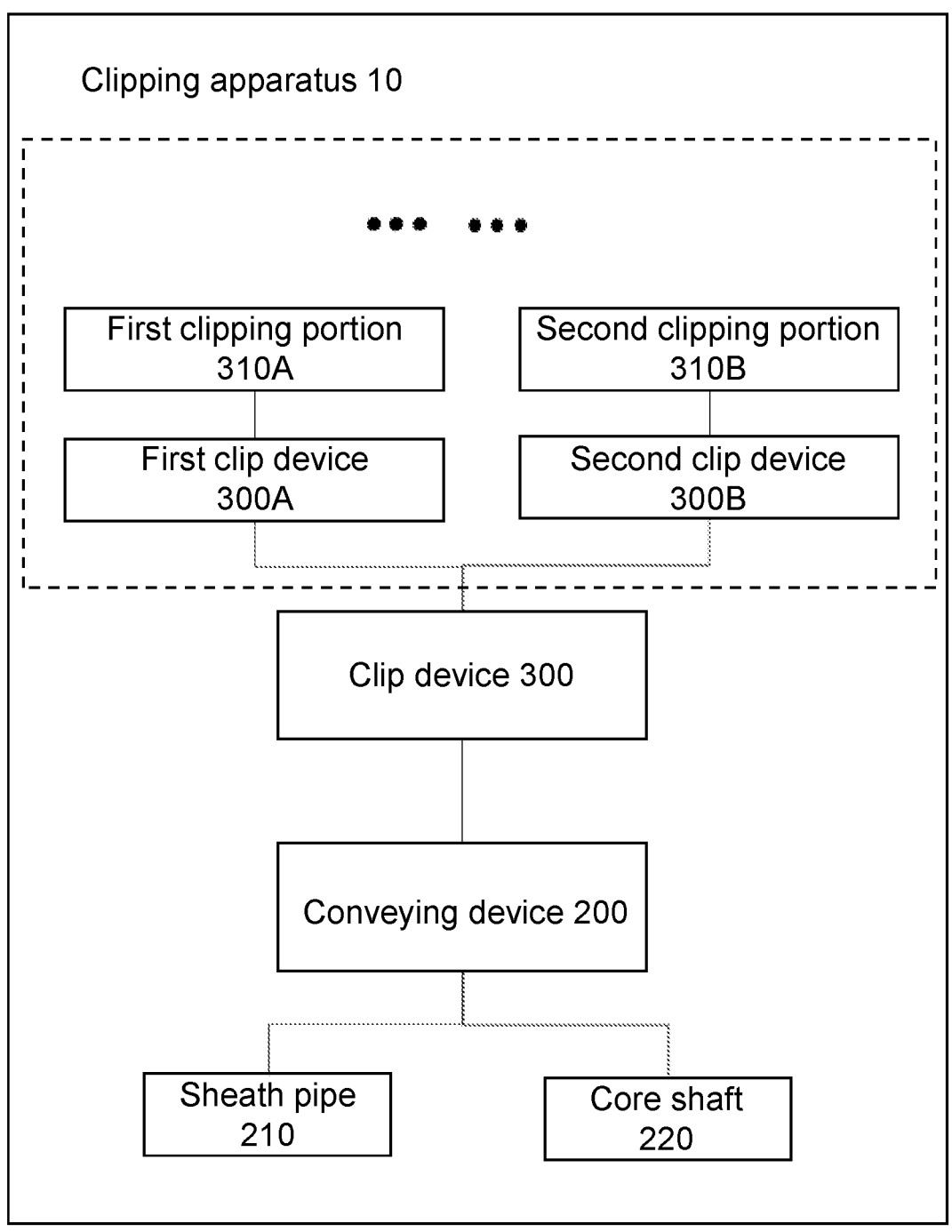
FIG. 1 is a block diagram illustrating an exemplary structure of a clip apparatus according to some embodiments of the present disclosure.

Description of markers in the accompanying drawings: 10, a clip apparatus; 20, a tissue; 100, a control device; 110, a fixed handle; 120, a sliding handle; 200, a conveying device; 210, a sheath pipe; 220, a core shaft; 221, a connecting head; 230, a bushing; 231, a second outer connecting portion; 232, an elastic arm; 233, a bonding hole; 300, a clip device; 300A, a first clip device; 300B, a second clip device; 300C, a third clip device; 310, a clipping portion; 310A, a first clipping portion; 310B, a second clipping portion; 310C, a third clipping portion; 311, a first outer connecting portion; 312, a resisting portion; 320, a clipping arm; 320A, a first clipping arm; 320B, a second clipping arm; 321, a clipping claw; 322, a curved arm; 323, a bending portion; 324, an inner connecting hole; 325, a first hole; 326, a pin roll; 327, an arching portion; 328, a fixing hole; 330, a first mating portion; 340, a second mating portion; 350, a second docking portion; 360, a first snap portion; 370, an accommodating slot; 380, a projection of a first distal end; 390, a projection of a second distal end; 391, a notch; 392, a passing hole; 400, an extension portion; 400A, a first extension portion; 400B, a second extension portion; 410, a bonding portion at a distal end; 420, a curved portion; 430, a bonding portion at a proximal end; 440, a third mating portion; 450, a first docking portion; 470, a second snap portion; 500, a locking portion; 500A, a first locking portion; 500B, a second locking portion; 510, a locking convexity; 511, a first locking slot; 512, a second locking slot; 520, a locking concavity; 521, a third locking slot; 530, a locked portion; 540, a locking stopper; 600, a bonding member; 600A, a first bonding member; 600B, a second bonding member; 600C, a third bonding member; 610, a first bonding portion; 620, a second bonding portion; 621, a deformation portion; 622, a first bevel; 700, a connecting member; 700A, a first connecting member; 700B, a second connecting member; 700C, a third connecting member; 710, a first connecting portion; 711, a snap hook; 7111, a resilient support arm; 7112, a hook structure; 720, a second connecting portion; 721, a tab; 722, a tongue piece; 730, a third connecting portion; 800, a storage pipe; 800A, a first storage pipe; 800B, a second storage pipe; 810, a passage; 810A, a first passage; 810B, a second passage; 820, a first outer connecting hole; 830, a second outer connecting hole; 840, a limit portion; 841, a fixing claw; 842, a fixing end; 843, a sliding slot; 850, an external pipe; 860, an internal pipe; 870, a blocking portion; 871, a penetrating hole; 900, a spacer portion; 910, a spacer hole; 920, a fracture; 930, a mating slot; 931, a guiding bevel.

DETAILED DESCRIPTION

To more clearly illustrate the technical solutions related to the embodiments of the present disclosure, a brief introduction of the drawings referred to the description of the embodiments is provided below. Obviously, the drawings described below are only some examples or embodiments of the present disclosure. Those having ordinary skills in the art, without further creative efforts, may apply the present disclosure to other similar scenarios according to these drawings. Unless obviously obtained from the context or the context illustrates otherwise, the same numeral in the drawings refers to the same structure or operation.

As shown in the present disclosure and claims, the words "one", "a", "a kind" and/or "the" are not especially singular but may include the plural unless the context expressly suggests otherwise. In general, the terms "comprise," "comprises," "comprising," "include," "includes," and/or "including," merely prompt to include operations and elements that have been clearly identified, and these operations and elements do not constitute an exclusive listing. The methods or devices may also include other operations or elements.

FIG. 1 is a block diagram illustrating an exemplary structure of a clip apparatus according to some embodiments of the present disclosure.

As shown in FIG. 1, some embodiments of the present disclosure provide a clip apparatus 10 that may be applied to a medical endoscope to perform operations such as clipping, hemostasis, suturing, etc., during endoscopic surgery.

In some embodiments, the clip apparatus 10 may include a conveying device 200 and at least two clip devices 300. The conveying device 200 has a good pass-through property, and the conveying device 200 and the at least two clip devices 300 pass through an endoscopic working passage into the human body or other organisms to approach a tissue to be clipped. The tissue refers to an organ tissue of the human body or other organisms. In some embodiments, the conveying device 200 may include a sheath pipe 210 provided with a passage and a core shaft 220 extending axially within the passage of the sheath pipe 210. The at least two clip devices 300 may be provided on a distal end and controlled by the core shaft 220 to perform operations such as opening, closing, locking, releasing, etc. In some embodiments, the sheath pipe 210 may be flexible and may bend in any direction.

The "proximal end" and "distal end" referred to in the embodiments of the present disclosure may indicate directions. The "proximal end" is toward a side where an operator is located, and the "distal end" is toward a side that extends into the body for treatment. The "proximal end" and the "distal end" may also denote a portion of a structure that is located in a corresponding direction, and should not be regarded only as end portions. "Axial direction" and "radial direction" in the embodiment of the present disclosure may indicate directions, where the "radial direction" is perpendicular to the "axial direction", or the "axial direction" is a direction in which the passage of the sheath pipe 210 extends, and the "radial direction" is a direction perpendicular to the direction in which the passage of the sheath pipe 210 extends.

In some embodiments, a count of clip devices 300 may be two, or more than two. In some embodiments, the clip apparatus 10 may be assembled with 2 to 10 clip devices 300, e.g., 3, 4, 5, 6, 7, 8, 9, etc. In some embodiments, the at least two clip devices 300 may include a first clip device 300A and a second clip device 300B. The first clip device 300A and the second clip device 300B respectively may include at least one clipping portion 310. The clipping portions 310 may include a first clipping portion 310A provided in the first clip device 300A and a second clipping portion 310B provided in the second clip device 300B. The clipping portions 310 may be provided outside the passage of the sheath pipe 210, i.e., both the first clipping portion 310A and second clipping portion 310B may be provided outside the passage of the sheath pipe 210. It should be understood that when the clip apparatus 10 may include a plurality of clip devices 300, the clipping portions of the plurality of clip devices 300 may all be provided outside the passage of the sheath pipe 210. The clipping portions 310 may perform operations such as opening, closing, locking, releasing, etc., to enable the clip devices 300 to complete a surgical operation. For example, the clip devices 300 may clip a wound of tissue to keep the wound closed for healing.

According to the above-described embodiments, the clip apparatus 10 may be provided with different counts of clip devices 300, and a user may choose the clip apparatus 10 provided with a suitable count of clip devices 300 according to a size of a trauma of tissue to be stopped from bleeding as predicted in the surgery. The operation of clipping the tissue may be performed a plurality of times without repeated insertion, and clipping closure of large wounds or a plurality of bleeding points may be achieved in a shorter time, reducing surgical risks and costs.

Figure 2:
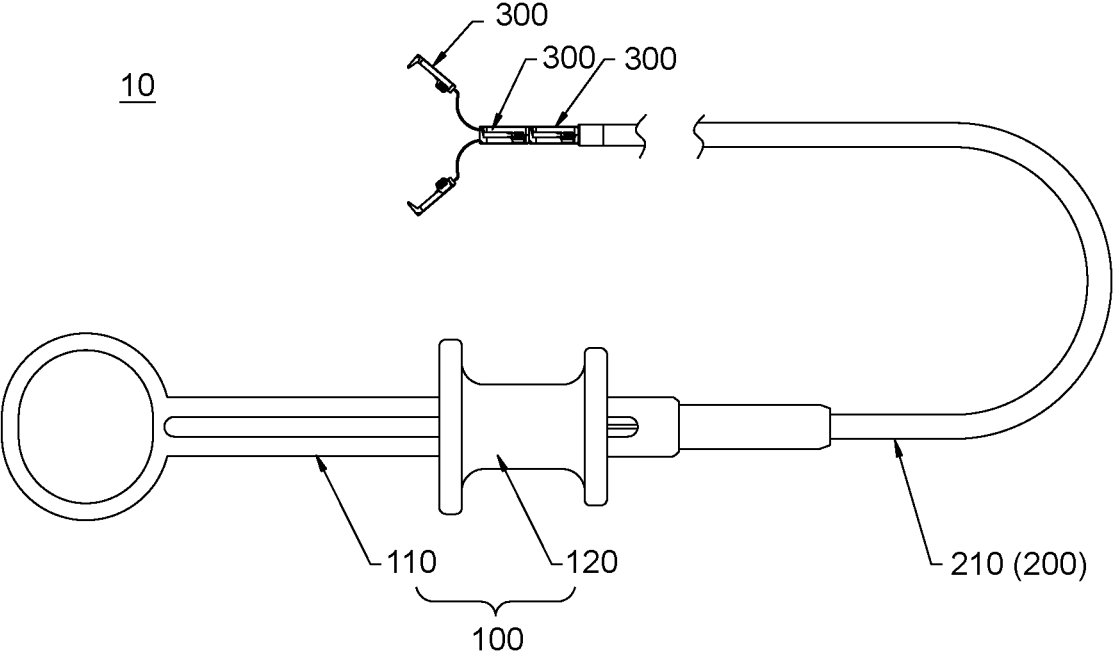
FIG. 2 is an exemplary diagram illustrating a structure of a clip apparatus according to some embodiments of the present disclosure.

FIG. 2 is an exemplary diagram illustrating a structure of a clip apparatus according to some embodiments of the present disclosure.

As shown in FIG. 2, the clip apparatus 10 may include a control device 100, the conveying device 200, and the at least two clip devices 300. The control device 100 may be provided on a distal end of the conveying device 200 and the at least two clip devices 300 may be provided on a proximal end of the conveying device 200. In some embodiments, the control device 100 may include a fixed handle 110 and a sliding handle 120. The sliding handle 120 may slide in an axial direction relative to the fixed handle 110, and a distal end of the sliding handle 120 may be fixedly connected to a proximal end of the core shaft 220. The user controls, outside of the body, the core shaft 220 to move along an axial direction of the passage of the sheath pipe 210 by controlling the sliding handle 120 to move along the axial direction of the fixed handle 110, which enables the clip device 300 to complete the corresponding surgical operation.

Figure 3A:
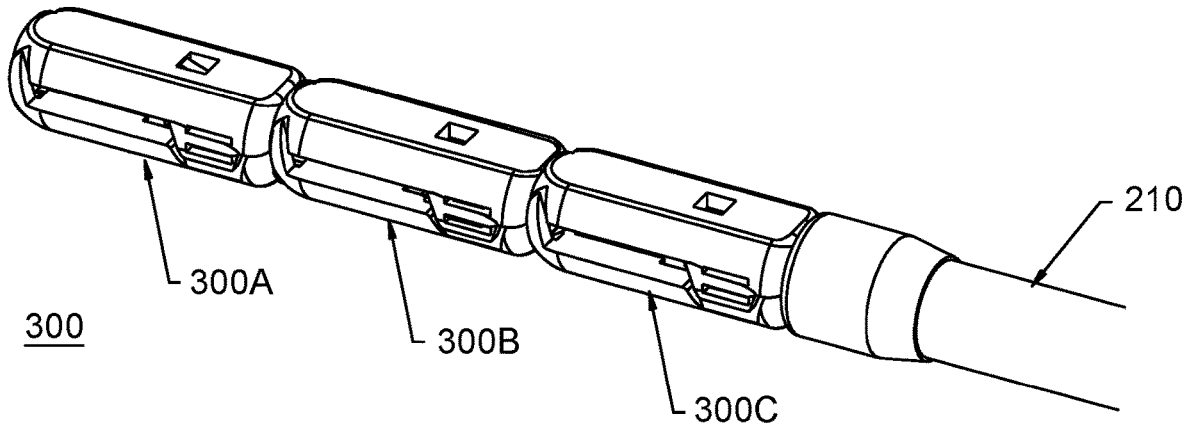
FIG. 3A is an exemplary diagram illustrating assembling a clip device according to some embodiments of the present disclosure, where a first clip device is in a closed state.
Figure 3B:
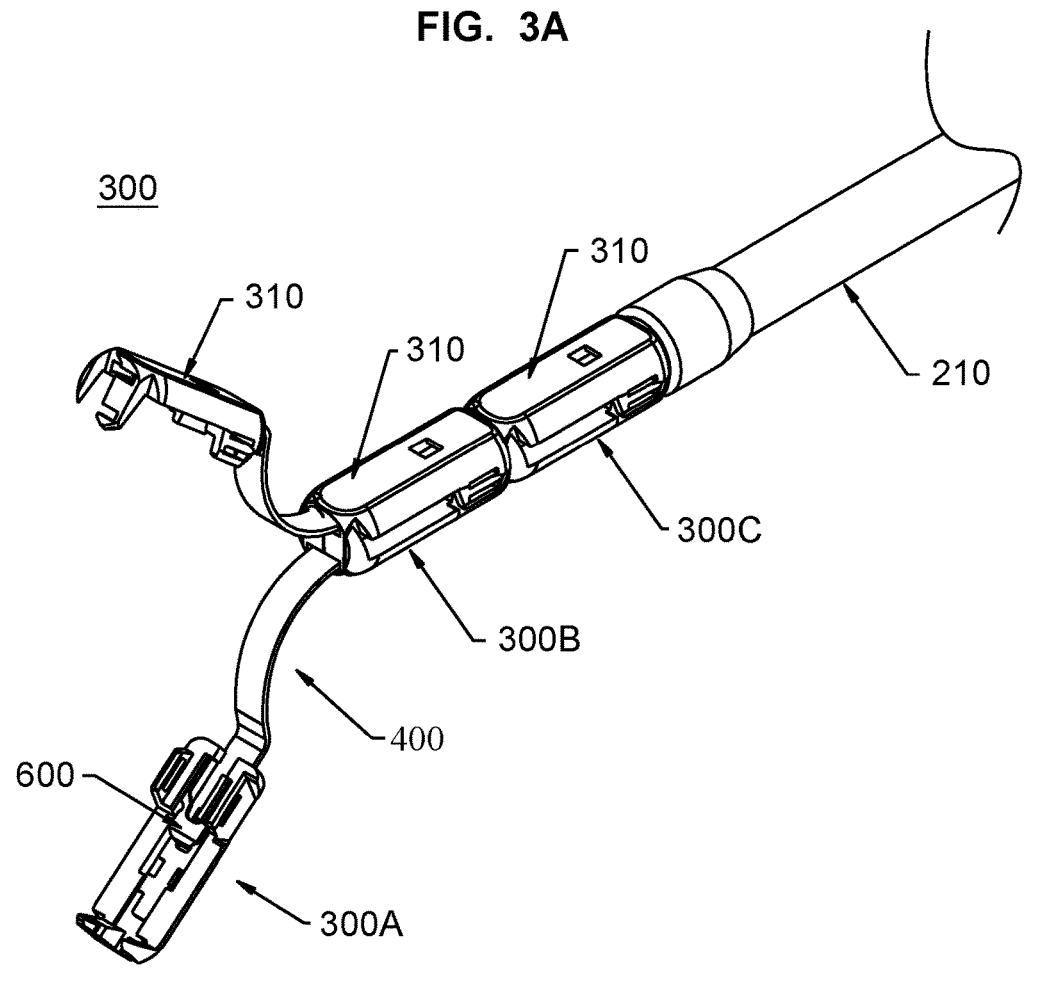
FIG. 3B is an exemplary diagram illustrating assembling a clip device according to some embodiments of the present disclosure, where a first clip device is in an opening state.

FIG. 3A is an exemplary diagram illustrating assembling a clip device according to some embodiments of the present disclosure, where the first clip device is in a closed state. FIG. 3B is an exemplary diagram illustrating assembling a clip device according to some embodiments of the present disclosure, where the first clip device is in an opening state.

In some embodiments, the at least two clip devices 300 may be releasably connected in sequence, and a proximal end of one of the clip devices 300 may be releasably connected to the sheath pipe 210. "Releasably connected" in the embodiments of the present disclosure refers to that two members remain connected when conditions are met (e.g., when an applied external force is less than a predetermined threshold) and achieve a release of the connection when the conditions are not met (e.g., when the applied external force is greater than the predetermined threshold).

As shown in FIGS. 3A and 3B, in some embodiments, the at least two clip devices 300 may include a first clip device 300A, a second clip device 300B, and a third clip device 300C provided in sequence from a distal end to a proximal end, and the proximal end of the third clip device 300C may be releasably connected to a distal end of the sheath pipe 210. After completing at least one of operations such as opening, closing, locking, etc., a release of the connection between the first clip device 300A and the second clip device 300B may be achieved and the first clip device 300A may stay in the human body. After continuing to perform the at least one of the operations such as opening, closing, locking, etc., a release of the connection between the second clip device 300B and the third clip device 300C may be achieved and the second clip device 300B may stay in the human body. After continuing to perform at least one of the operations such as opening, closing, locking, etc., a release of the connection between the third clip device 300C and the sheath pipe 210 may be achieved and the third clip device 300C may stay in the human body. In some embodiments, the clip apparatus 10 may include two or more clip devices 300, and the releasing process of the clip devices 300 may be referenced to the releasing process of the first clip device 300A, the second clip device 300B, and the third clip device 300C.

In some embodiments, a total length of the at least two clip devices 300 when connected to each other may be less than a sum of a length of each of the at least two clip devices 300, which results in the total length of the at least two clip devices 300 connected to each other outside of the sheath pipe 210 being smaller and facilitating operations. In some embodiments, a portion of the structure of the clip device 300 (e.g., an extension portion 400 referred to below) may be stored within another clip device 300, or a portion of the structure of the clip device 300 (e.g., the extension portion 400 referred to below) may be stored within the sheath pipe 210 to reduce the length of the at least two clip devices 300 connected to each other outside of the sheath pipe 210.

Different embodiments of the clip apparatus 10 may be illustrated in the following using three exemplary embodiments, provided that the embodiments of the present disclosure include, but are not limited to, example one, example two, and example three, and that, without conflict, features of the three examples may be combined or referred in any combination, which is not limited in the present disclosure.

The clip apparatus of example one may be described in detail below in conjunction with FIGS. 4-12E.

Figure 4:
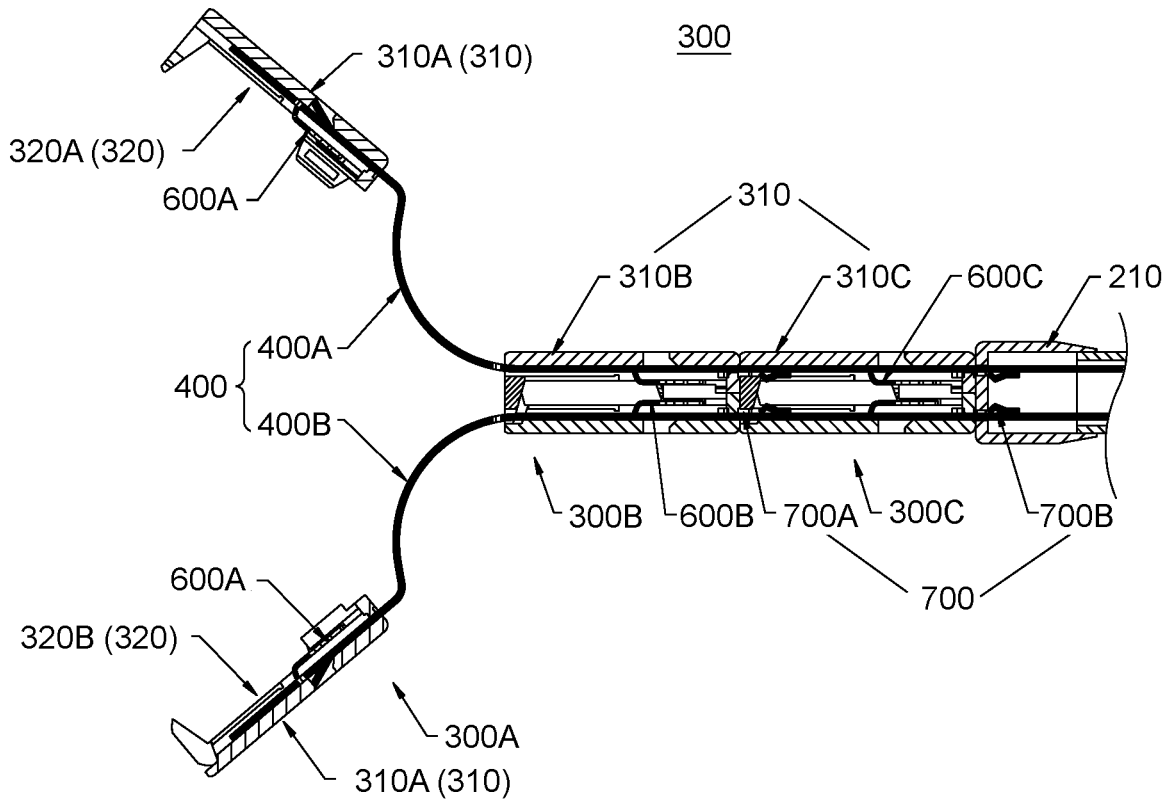
FIG. 4 is a diagram illustrating a cross section of a clip device along an axis according to some embodiments of the present disclosure.

FIG. 4 is a diagram illustrating a cross section of a clip device along an axis according to some embodiments of the present disclosure.

As shown in FIG. 4, in some embodiments, the at least two clip devices 300 may further include the extension portion 400, and the extension portion 400 may be connected to the at least two clipping portions 310. A proximal end of the extension portion 400 may be connected to the core shaft 220 (not shown in FIG. 4), and a distal end of the extension portion 400 may be switchably connected to one of the clipping portions 310. The "switchably connected" may be that a release of the connection between a distal end of the extension portion 400 and one of the clipping portions 310 is achieved and then the distal end of the extension portion 400 is switched to connecting to one of the rest of the clipping portions 310. Exemplarily, the clipping portions 310 may include the first clipping portion 310A provided in the first clip device 300A and the second clipping portion 310B provided in the second clip device 300B. The distal end of the extension portion 400 may be releasably connected to the first clipping portion 310A. When a release of the connection between the distal end of the extension portion 400 and the first clipping portion 310A is achieved, the distal end of the extension portion 400 may be releasably connected to the second clipping portion 310B. In some embodiments, when the extension portion 400 is connected to the first clipping portion 310A, the extension portion 400 and the first clipping portion 310A may form the first clip device 300A. When the extension portion 400 is connected to the second clipping portion 310B, the extension portion 400 and the second clipping portion 310B may form the second clip device 300B.

In some embodiments, the core shaft 220 may be of a split structure with the extension portion 400, and the distal end of the core shaft 220 may be fixedly connected to the proximal end of the extension portion 400 through snap-fit, welding, etc. In some embodiments, the core shaft 220 may be of a one-piece structure with the extension portion 400, and the distal end of the core shaft 220 may extend to form the extension portion 400.

In some embodiments, the total length of the at least two clip devices 300 when connected to each other may be less than a sum of a length of each of the at least two clip devices 300. The clip devices 300 may include the clipping portions 310 and the extension portion 400. The length of each of the clip devices 300 may be a distance from a distal end of one of the clipping portions 310 to an end of the extension portion 400 protruding from one of the rest of the clip devices 300 or the sheath pipe 210 immediately adjacent thereto when the clip device 300 is in a fully opening state. For example, the length of the clip device 300A may be a sum of a length of the clipping portions 310 and a length of a portion of the extension portion 400 that protruding from the clip device 300B when the clip device 300A is open. When the clip devices 300 are connected to each other, at least a portion of the extension portion 400 may extend into the plurality of clipping portions 310, and the plurality of clipping portions 310 are connected to each other. A total length of the clipping portions 310 connected to each other refers to the total length of the clip devices 300 connected to each other, which is known to be less than the sum of the length of each of the clip devices 300.

In some embodiments, the core shaft 220 may control the clipping portions 310 to perform operations such as opening, closing, locking, releasing, etc., through the extension portion 400. The core shaft 220 may move axially within the sheath pipe 210 to drive the extension portion 400 to move axially relative to the sheath pipe 210, and the axial movement of the extension portion 400 may control the clipping portions 310 connected thereto to open, close, lock, release, etc., thereby completing the action of clipping the tissue. When the clipping portions 310 are in the opening state, one of the clipping portions 310 may be separated from one of the rest of the clipping portions 310 or the sheath pipe 210, and the extension portion 400 may extend out of the one of the rest of the clipping portions 310 or the sheath pipe 210 to provide a span that is large enough for clipping more tissue. At this time, the length of the clip device 300 protruding from the one of the rest of the clipping portions 310 or the sheath pipe 210 immediately adjacent thereto is the length of the clip device 300. After locking at least one of the clipping portions 310, the extension portion 400 may be separated from the locked clipping portion 310, leaving the clipping portion 310 to stay in the body. By releasably connecting the clipping portions 310 with the extension portion 400, the clipping portion 310 with a small size may be allowed to stay in the body, which may provide a larger operating space for subsequent surgical operations, and reduces the impact on the human body.

In some embodiments, each of the clipping portions 310 may include a clipping arm 320. The clipping arm 320 may include a first clipping arm 320A and a second clipping arm 320B. The extension portion 400 may include a first extension portion 400A and a second extension portion 400B, with both a proximal end of the first extension portion 400A and a proximal end of the second extension portion 400B extending into the sheath pipe 210 to be connected to the core shaft 220. The first clipping arm 320A of the at least two clipping portions 310 may be provided on a portion of the first extension portion 400A extending out of the sheath pipe 210, and the second clipping arm 320B of the at least two clipping portions 310 may be provided on a portion of the second extension portion 400B extending out of the sheath pipe 210. In some embodiments, the first extension portion 400A and the second extension portion 400B may control the clipping portions 310 to perform operations such as opening, closing, locking, and releasing. When the clipping portions 310 are open, the first clipping arm 320A and the second clipping arm 320B may be located away from each other. When the clipping portions 310 are closed, the first clipping arm 320A and the second clipping arm 320B may be located close to each other. When the clipping portions 310 are locked, the first clipping arm 320A and the second clipping arm 320B may be locked to each other. When the clipping portions 310 are released, the first clipping arm 320A and the second clipping arm 320B may remain locked and stay in the human body.

In some embodiments, when the clipping portions 310 are in the opening state, an included angle between the first clipping arm 320A and the second clipping arm 320B may be less than or equal to 180° to form a clipping space that facilitates clipping the tissue.

Figure 5:
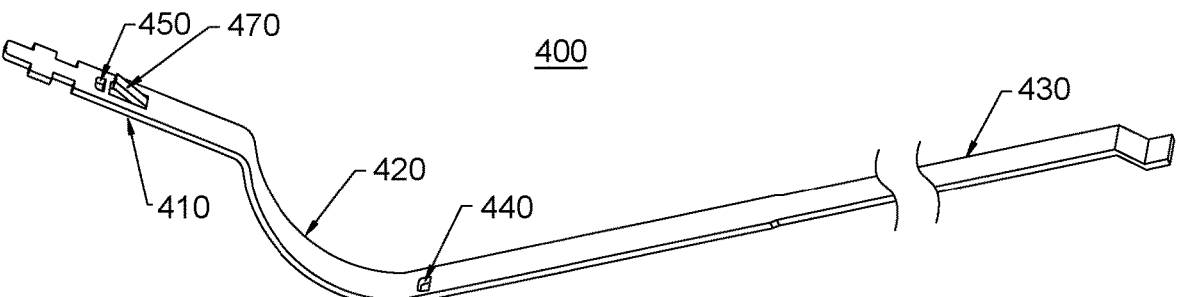
FIG. 5 is an exemplary diagram illustrating a structure of an extension portion according to some embodiments of the present disclosure.

FIG. 5 is an exemplary diagram illustrating a structure of an extension portion according to some embodiments of the present disclosure.

As shown in FIG. 4 and FIG. 5, in some embodiments, the extension portion 400 may be provided with a bonding portion at a distal end 410, a curved portion 420, and a bonding portion at a proximal end 430. The bonding portion at the distal end 410 may be releasably connected to the clipping arm 320, the curved portion 420 may connect the bonding portion at the distal end 410 to the bonding portion at the proximal end 430, and the bonding portion at the proximal end 430 may be connected to the core shaft 220.

In some embodiments, the plurality of clipping portions 310 may be sequentially arranged along an axial direction of the sheath pipe 210. In some embodiments, when the bonding portion at the distal end 410 of the extension portion 400 is releasably connected to the first clipping portion 310A, the rest clipping portions 310 (e.g., the second clipping portion 310B, etc.) located between the first clipping portion 310A and the distal end of the sheath pipe 210 may remain connected to the bonding portion at the proximal end 430 of the extension portion 400. At this time, the extension portion 400 may move axially relative to the rest clipping portions 310.

In some embodiments, the curved portion 420 may be flexible. In some embodiments, the curved portion may be made of materials such as metallic stainless steel, etc. In some embodiments, by setting a bending degree of the curved portion 420 and/or an included angle between a connection region connecting the bonding portion at the distal end 410 and the curved portion 420, it is possible to set a distance between the first clipping arm 320A and the second clipping arm 320B when the clipping portions 310 are in the opening state. In some embodiments, the extension portion 400 may be moved from a proximal end to a distal end to open the first clipping portion 310A located in the bonding portion at the distal end 410 of the extension portion 400, and the curved portion 420 causes a larger distance between the first clipping arm 320A and the second clipping arm 320B. When the extension portion 400 is moved from the distal end to the proximal end, the curved portion 420 may be deformed by extrusion due to the constraints of the radial dimensions of the rest of the clipping portions 310 or the sheath pipe 210, which converts the clipping portions 310 from the opening state to the closed state, and the curved portion 420 may be stored into the other clipping portion 310 or the sheath pipe 210 to save space.

In some embodiments, the curved portion 420 may be bent outward along a radial direction (i.e., a concave surface of the curved portion 420 is turned away from an axis of the clip devices 300) relative to the bonding portion at the proximal end 430, and the curved portion 420 may be bent inward along the radial direction (i.e., the concave surface of the curved portion 420 is turned towards the axis of the clip devices 300) relative to the bonding portion at the distal end 410. The radial direction refers to a radial direction of the sheath pipe 210 or a radial direction of the clip devices 300, which is perpendicular to an axis of the sheath pipe 210 or the axis of the clip devices 300. In some embodiments, the curved portion 420 may be curved, and the bonding portion at the proximal end 430 may be tangent to the curved portion 420, reducing resistance and wear at a junction of the bonding portion at the proximal end 430 and the curved portion 420 as the bonding portion at the proximal end 430 moves in and out of the clipping portion 310 or the sheath pipe 210. In some embodiments, a junction between the bonding portion at the distal end 410 and the curved portion 420 may have a rounded and smooth transition to reduce the concentration of stress at the junction between the bonding portion at the distal end 410 and the curved portion 420, preventing the bonding portion at the distal end 410 from fracturing at the junction. In other embodiments, the curved portion 420 may include, but is not limited to, an arcuate, a folded line, or other curved shape.

In some embodiments, the clip apparatus 10 may further include a bonding member 600, and the bonding member 600 may be configured to releasably connect the extension portion 400 to at least one of the clipping portions 310. In some embodiments, the bonding member 600 may be provided within the clipping portions 310 and releasably connected to the bonding portion at the distal end 410 of the extension portion 400. More descriptions regarding the bonding member 600 may be found in the embodiments of the bonding member 600 hereinafter.

Figure 6:
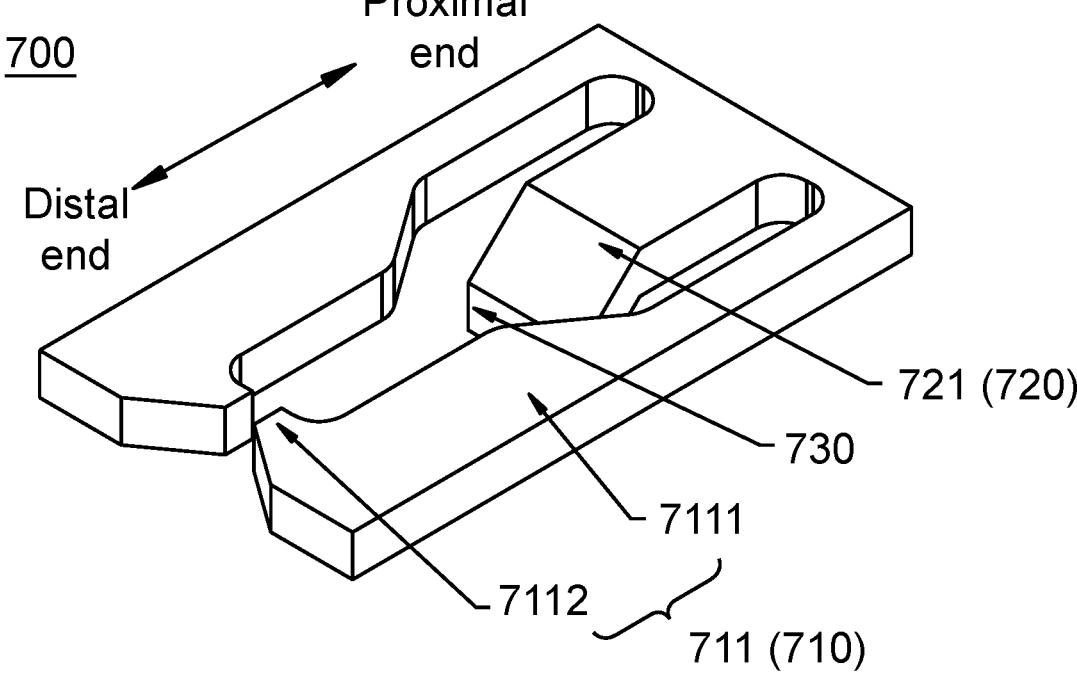
FIG. 6 is an exemplary diagram illustrating a structure of a connecting member according to some embodiments of the present disclosure.
Figure 7:
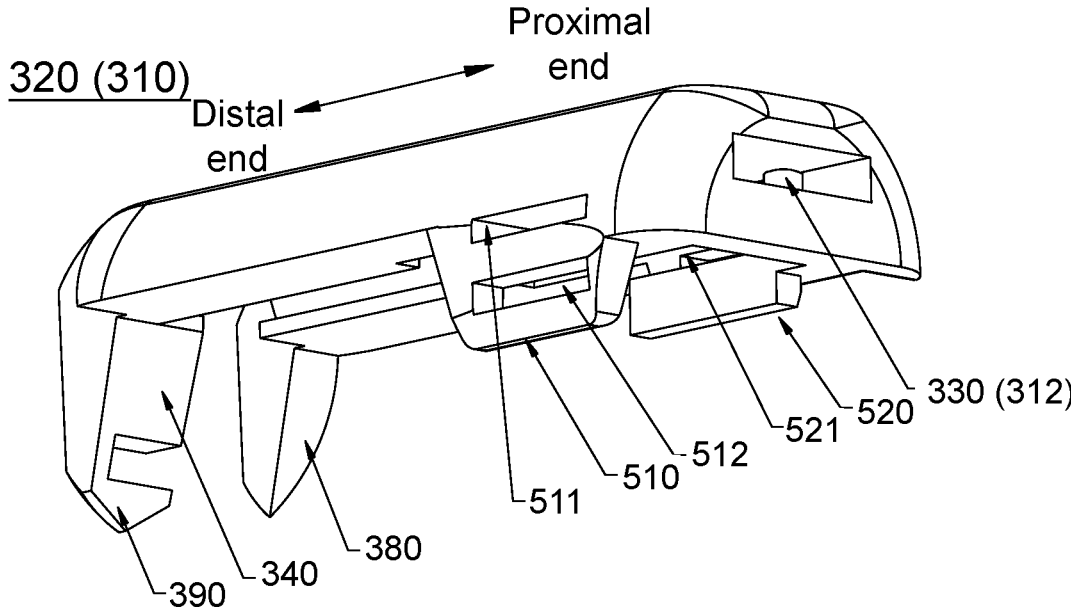
FIG. 7 is a first exemplary diagram illustrating a structure of a clipping arm according to some embodiments of the present disclosure.

FIG. 6 is an exemplary diagram illustrating a structure of a connecting member according to some embodiments of the present disclosure. FIG. 7 is a first exemplary diagram illustrating a structure of a clipping arm according to some embodiments of the present disclosure.

As shown in FIG. 4 and FIG. 6, in some embodiments, the clip apparatus 10 may further include a connecting member 700. At least one of the clipping portions 310 may be releasably connected to at least one of the rest of the clipping portions 310 through the connecting member 700, and/or at least one of the clipping portions 310 may be releasably connected to the sheath pipe 210 through the connecting member 700. A connection between two of the clipping portions 310 and/or a connection between the clipping portions 310 and the sheath pipe 210 may be achieved utilizing the connecting member 700, which can improve the stability of the clipping portions 310, avoiding relative movement or relative rotation between the clipping portions 310 or between the clipping portions 310 and the sheath pipe 210.

As shown in FIG. 4, FIG. 6, and FIG. 7, in some embodiments, the connecting member 700 may include a first connecting portion 710 and a second connecting portion 720, the proximal end of at least one of the clipping portions 310 may include a first mating portion 330, a distal end of at least one of the rest of the clipping portions 310 and/or a distal end of the sheath pipe 210 may include a second mating portion 340. In some embodiments, the first connecting portion 710 may mate with the first mating portion 330, and the second connecting portion 720 may mate with the second mating portion 340 to achieve the connection between two of the clipping portions 310 and/or the connection between the clipping portions 310 and the sheath pipe 210. In some embodiments, a release of the mating of the first connecting portion 710 and the first mating portion 330 and a release of the mating of the second connecting portion 720 and the second mating portion 340 may achieve a release of the connection between two of the clipping portions 310, and/or a release of the connection between the clipping portions 310 and the sheath pipe 210.

In some embodiments, the clipping portions 310 may include the first clipping portion 310A provided in the first clip device 300A and the second clipping portion 310B provided in the second clip device 300B. The proximal end of the first clipping portion 310A may include a first mating portion 330, and the distal end of the second clipping portion 310B may include the second mating portion 340. A distal end of the connecting member 700 may be provided on the proximal end of the first clipping portion 310A and may mate with the first mating portion 330 through the first connecting portion 710, and the proximal end of the connecting member 700 may be provided on the distal end of the second clipping portion 310B and may mate with the second mating portion 340 through the second connecting portion 720, to realize the connection between the first clipping portion 310A and the second clipping portion 310B. A release of the mating of the first connecting portion 710 and the first mating portion 330 and a release of the mating of the second connecting portion 720 and the second mating portion 340 may achieve a release of connection between the first clipping portion 310A and the second clipping portion 310B. In some embodiments, one, two, or more connecting members 700 may be provided on a connection region connecting the first clipping portion 310A and the second clipping portion 310B to increase the stability of the connection between the first clipping portion 310A and the second clipping portion 310B.

As shown in FIG. 6, in some embodiments, the connecting member 700 may be constructed in a tabular structure to reduce the radial space that the connecting member 700 takes up in the clipping portion 310. In some embodiments, the connecting member 700 may also be constructed in other structures, such as an elongate structure, which is not limited in the present disclosure.

In some embodiments, the mating of the first connecting portion 710 and the first mating portion 330 may limit the connecting member 700 from moving toward an proximal end relative to the clipping portions 310, and the mating of the second connecting portion 720 and the second mating portion 340 may limit the connecting member 700 from moving toward a distal end relative to the clipping portions 310. When the connecting member 700 is connected between the two clipping portions 310, axial movement between the two clipping portions 310 may be limited.

As shown in FIG. 6 and FIG. 7, in some embodiments, the first connecting portion 710 may include a snap hook 711. In some embodiments, the snap hook 711 may include two resilient support arms 7111 and hook structures 7112. A proximal end of each of the two resilient support arms 7111 may be connected to the proximal end of the connecting member 700, and a distal end of each of the two resilient support arms 7111 may extend to the distal end of the connecting member 700 and may be formed as a free end. The hook structure 7112 may be provided on the distal end of each of the two resilient support arms 7111, and two hook structures 7112 on the two resilient support arms 7111 may be provided opposite each other. In some embodiments, the first mating portion 330 of the clipping portions 310 may be a limit column, and an axial direction of the limit column may be provided in a radial direction of the clipping portion 310. In some embodiments, the snap hook 711 may mate with the limit column. For example, the limit column may cross over the hook structure 7112 and stop between the two resilient support arms 7111 through the hook structures 7112, such that the first connecting portion 710 may mate with the first mating portion 330. In some embodiments, deformation, fracture, or displacement of the snap hook 711 by a force may achieve a release of the mating of the snap hook 711 and the limit column and a release of the mating of the first connecting portion 710 and the first mating portion 330. For example, when the connecting member 700 is subjected to a force from a distal end to a proximal end, the two resilient support arms 7111 of the snap hook 711 may deform and depart away from each other, and the hook structure 7112 may be disengaged from the limit column. As another example, the hook structure 7112 of the snap hook 711 may break away from the distal end of each of the resilient support arms 7111 to achieve a release of connection between the snap hook 711 and the limit column. As yet another example, the hook structure 7112 may rotate relative to each of the resilient support arms 7111 to achieve a release of connection between the snap hook 711 and the limit column.

In some embodiments, after the first connecting portion 710 mates with the first mating portion 330, deformation, fracture, or displacement of the limit column of the first mating portion 330 may achieve a release of the mating of the first connecting portion 710 and the first mating portion 330.

In some embodiments, the connecting member 700 may include a tab 721 constructed as a resilient arch. One end of the tab 721 may be connected to the proximal end of the connecting member 700, another end may be formed toward the distal end of the connecting member 700 as a free end, and an outer arched surface of the tab 721 may be constructed as the second connecting portion 720. In some embodiments, the tab 721 may be provided between the two resilient support arms 7111 of the first connecting portion 710, and the tab 721 may bend into an arch shape in a thickness direction of the connecting member 700. In some embodiments, an axial length of the tab 721 may be less than an axial length of each of the resilient support arms 7111.

In some embodiments, the second mating portion 340 of the clipping portion 310 may include a limit surface. The outer arched surface of the tab 721 may mate with the limit surface to cause the second connecting portion 720 to mate with the second mating portion 340. A release of the mating of the outer arched surface of the tab and the limit surface achieves a release of the mating of the second connecting portion 720 and the second mating portion 340.

In some embodiments, the tab 721 may be deformed in the thickness direction of the connecting member 700 by being subjected to a force, and the deformation of the tab 721 causes the second connecting portion 720 (i.e., the outer arched surface of the tab 721) to protrude from a surface of the connecting member 700 along the thickness direction. At this time, the outer arched surface may mate with the limit surface, and the outer arched surface may return to its original shape and the mating of the outer arched surface and the limit surface may be released when the force on the tab 721 is released.

In some embodiments, the first connecting portion 710 and the second connecting portion 720 may include other structures, and the first mating portion 330 and the second mating portion 340 may include other structures, which may be referred to in the structure of the connecting member 700 in example two below but not constitute a limitation on the structure of the connecting member 700 in the present disclosure.

As shown in FIG. 4 and FIG. 6, in some embodiments, the connecting member 700 may include a third connecting portion 730. The third connecting portion 730 may be subjected to a force to satisfy a preset condition to achieve a release of the connection between the at least one of the clipping portions 310 and at least one of the rest of the clipping portions 310, and/or the connecting member 700 may achieve a release of the connection between the at least one of the clipping portions 310 and the sheath pipe 210. In some embodiments, the preset condition may include that the third connecting portion 730 is subjected to a force from a distal end to a proximal end and the force reaches a predetermined threshold. When the preset condition is satisfied, a release of the mating of the first connecting portion 710 of the connecting member 700 and the first mating portion 330 of the clipping portions 310 is achieved, and a release of the mating of the second connecting portion 720 of the connecting member 700 and the second mating portion 340 of the another clipping portions 310 is achieved, then a release of the connection between two adjacent clipping portions 310 is achieved, and/or a release of the connection between the clipping portions 310 and the sheath pipe 210 is achieved.

In some embodiments, after the release of the connection between the at least one of the clipping portions 310 and the at least one of the rest of the clipping portions 310, the third connecting portion 730 may be operable to drive the connecting member 700 to move into the at least one of the rest of the clipping portions 310. In some embodiments, after the connecting member 700 is subjected to a force to achieve a release of the connection between the at least one of the clipping portions 310 and the sheath pipe 210, the connecting member 700 may be operable to move into the sheath pipe 210.

In some embodiments, the third connecting portion 730 and the second connecting portion 720 may be different portions in an integral structure, and the second connecting portion 720 may be deformed or displaced to form the third connecting portion 730. In some embodiments, the connecting member 700 may include the tab 721, with one end of the tab 721 being connected to the proximal end of the connecting member 700, and another end of the tab 721 being formed towards the distal end of the connecting member 700 as a free end, which constitutes the third connecting portion 730. More descriptions regarding the tab 721 may be found in related descriptions of the tab 721 hereinabove.

In some embodiments, the third mating portion 440 of the extension portion 400 may include a hole or a slot, and the third mating portion 440 may be provided on a bonding portion at the proximal end 430 of the extension portion 400.

In some embodiments, the tab 721 is constructed as a resilient arch. When the connecting member 700 is provided in the clipping portions 310 or the sheath pipe 210, in the thickness direction of the connecting member 700, the tab 721 is squeezed and deformed so that the second connecting portion 720 may mate with the second mating portion 340 of the clipping portions 310. When the extension portion 400 moves to a position of the free end of the tab 721, at this time, the tab 721 is released from being squeezed and returns to its original shape, and the third mating portion 440 of the extension portion 400 may mate with the third connecting portion 730 of the tab 721.

In some embodiments, the third connecting portion 730 and the second connecting portion 720 may be separately molded, e.g., the third connecting portion 730 and the second connecting portion 720 may be different resilient members provided on different locations in the connecting member 700.

As shown in FIG. 4 through FIG. 6, in some embodiments, the extension portion 400 may provide an operative force for the third connecting portion 730. The extension portion 400 may include the third mating portion 440, which is releasably connected to the third connecting portion 730. In some embodiments, the preset condition for the third connecting portion 730 to be subjected to a force may include that the extension portion 400 is moved from a distal end to a proximal end. When the extension portion 400 provides the third connecting portion 730 with an operating force greater than the predetermined threshold, the tab 721 may be deformed, thereby changing the shape or state of the second connecting portion 720 to achieve a release of the mating of the second connecting portion 720 and the second mating portion 340. Then, the extension portion 400 may drive the third connecting portion 730 to move from a distal end to a proximal end. When the third connecting portion 730 moves from the distal end to the proximal end, the release of the mating of the first connecting portion 710 of the connecting member 700 and the first mating portion 330 of the clipping portions 310 is achieved, and the release of the mating of the second connecting portion 720 of the connecting member 700 and the second mating portion 340 of the clipping portions 310 is achieved. In some embodiments, the extension portion 400 may be moved from the distal end to the proximal end, and when the extension portion 400 provides a sufficiently large operating force on the third connecting portion 730, the tab 721 and the snap hook 711 may be deformed simultaneously, the deformation of the tab 721 may change the shape or state of the second connecting portion 720 to achieve the release of the mating of the second connecting portion 720 and the second mating portion 340, and the deformation of the snap hook 711 may achieve the release of the mating of the first connecting portion 710 and the first mating portion 330.

In some embodiments, there are a plurality of the connecting members 700, and one of the plurality of connecting members 700 may provide an operating force on one of the rest of the plurality of connecting members 700. In some embodiments, the preset condition for the third connecting portion 730 to be subjected to the force may include that at least one of the connecting members 700 pushes at least one of the rest of the connecting members 700 to move from a distal end to a proximal end. In some embodiments, the connecting member 700 may include a first connecting member 700A and a second connecting member 700B. The first connecting member 700A connects the second clipping portion 310B and the third clipping portion 310C, the second connecting member 700B connects the third clipping portion 310C and the sheath pipe 210. When the first connecting member 700A enters into the third clipping portion 310C under the action of the extension portion 400, the proximal end of the first connecting member 700A abuts against the distal end of the second connecting member 700B. When a pushing force generated by the first connecting member 700A on the second connecting member 700B is greater than a predetermined threshold, deformation, fracture, or displacement of the snap hook 711 of the second connecting member 700B or the limit column of the third clipping portion 310C achieve a release of a mating of the first connecting portion 710 of the second connecting member 700B and the first mating portion 330 of the third clipping portion 310C and a release of a mating of the second connecting portion 720 of the second connecting member 700B and the second mating portion 340 of the third clipping portion 310C.

As shown in FIGS. 4-7, in some embodiments, the clipping portions 310 may include the first clipping portion 310A, the second clipping portion 310B, and the third clipping portion 310C, and the connecting member 700 may include the first connecting member 700A and the second connecting member 700B. The first connecting member 700A may connect the second clipping portion 310B to the third clipping portion 310C, and the second connecting member 700B may connect the third clipping portion 310C to the sheath pipe 210. The extension portion 400 may release the first clipping portion 310A from the second clipping portion 310B after controlling the first clipping portion 310A to clip the tissue. At this time, the second clipping portion 310B is connected to the distal end of the extension portion 400 and may be configured to clip the tissue, and after the distal end of the extension portion 400 enters into the second clipping portion 310B, the third mating portion 440 of the extension portion 400 may mate with the third connecting portion 730 of the first connecting member 700A. When moved from the distal end to the proximal end, the extension portion 400 may drive the first connecting member 700A to move into the third clipping portion 310C, at this time a release of the connection between the second clipping portion 310B and the third clipping portion 310C may be achieved. After the release of the connection between the second clipping portion 310B and the third clipping portion 310C, the third clipping portion 310C is connected to the distal end of the extension portion 400, at this time, the third clipping portion 310C may be configured to clip the tissue. The extension portion 400 continues to move from the distal end to the proximal end until the proximal end of the first connecting member 700A abuts against the distal end of the second connecting member 700B. The extension portion 400 continues to drive the first connecting member 700A to move from the distal end to the proximal end, achieving the release of the mating of the first connecting portion 710 of the second connecting member 700B and the first mating portion 330 of the third clipping portion 310C and the release of the mating of the second connecting portion 720 of the second connecting member 700B and the sheath pipe 210, thus achieving the release of the connection between the third clipping portion 310C and the sheath pipe 210.

In some embodiments, the third connecting portion 730 may also be operated by other members, which is not limited in the present disclosure.

As shown in FIG. 6 and FIG. 7, in some embodiments, the clipping portions 310 may include a resisting portion 312. After the connecting member 700 is moved into the clipping portions 310, the proximal end of the connecting member 700 abuts against the resisting portion 312 such that the connecting member 700 stays in the clipping portion 310. In some embodiments, the first mating portion 330 may form the resisting portion 312. After the connecting member 700 is moved into the clipping portion 310 and abuts against one of the rest of the connecting members 700 to achieve a release of the mating of the first connecting portion 710 of the one of the rest of the connecting members 700 and the first mating portion 330 of the clipping portions 310, the proximal end of one of the connecting members 700 may abut against the resisting portion 312 (i.e., the first mating portion 330) such that the connecting member 700 stays in the clipping portion 310. In some embodiments, the resisting portion 312 may be provided separately from the first mating portion 330, with the resisting portion 312 being closer to the distal end of the clipping portion 310 relative to the first mating portion 330. After moving into the clipping portion 310, the connecting member 700 may firstly abut against the resisting portion 312, then released from the extension portion 400 and stay in the clipping portion 310. The extension portion 400 may continue to move from the distal end to the proximal end and mate with the next connecting member 700, and a release of the connection between the connecting member 700 and the clipping portion 310 and/or sheath pipe 210 may be achieved through the extension portion 400.

In some embodiments, the resisting portion 312 may also be a structure different from the first mating portion 330, which is capable of preventing the connecting member 700 from moving from the distal end to the proximal end.

Figure 8:
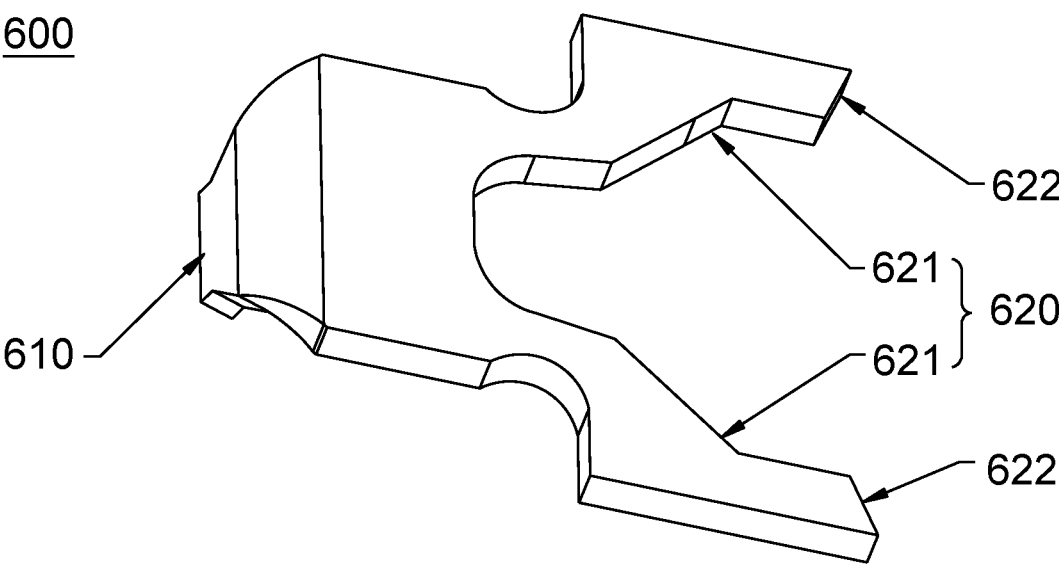
FIG. 8 is an exemplary diagram illustrating a structure of a bonding member according to some other embodiments of the present disclosure.
Figure 9:
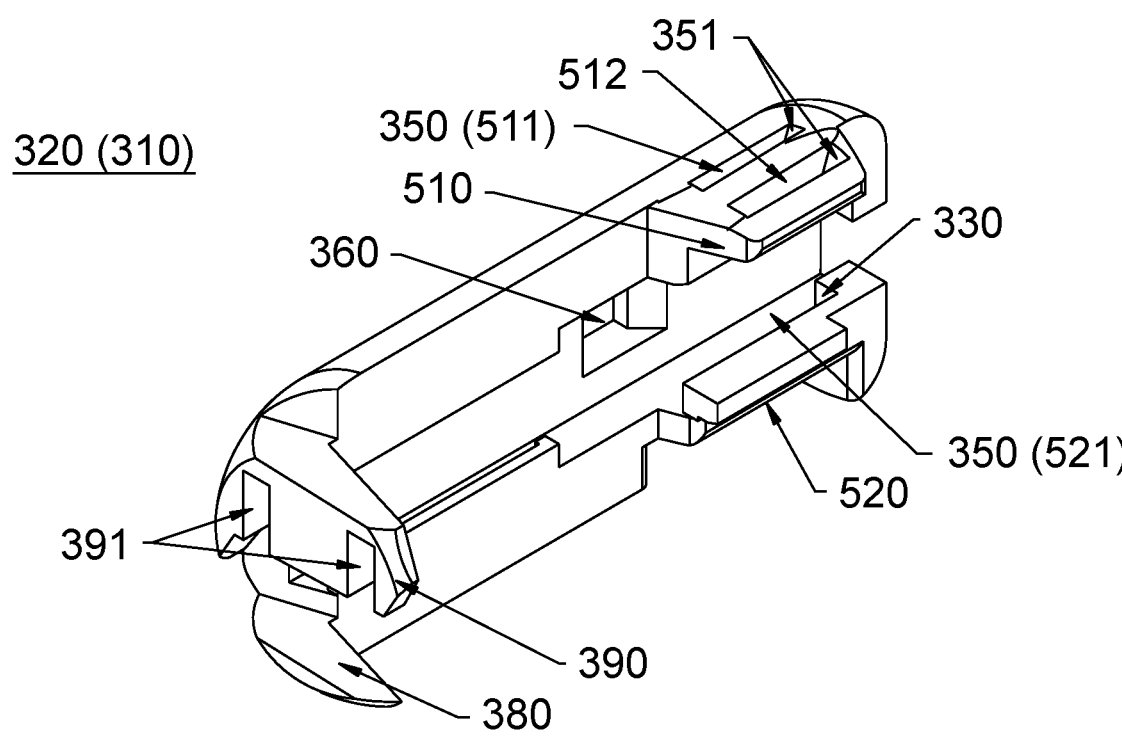
FIG. 9 is a second exemplary diagram illustrating a structure of a clipping arm according to some embodiments of the present disclosure.

FIG. 8 is an exemplary diagram illustrating a structure of a bonding member according to some other embodiments of the present disclosure. FIG. 9 is a second exemplary diagram illustrating a structure of a clipping arm according to some embodiments of the present disclosure.

As shown in FIG. 3 B and FIG. 8, in some embodiments, the clip device 300 may further include the bonding member 600, the bonding member 600 may be configured to releasably connect at least one of the clipping portions 310 to the extension portion 400. In some embodiments, when the extension portion 400 is moved from a distal end to a proximal end, a release of the connection between the bonding member 600 and the clipping portions 310, and/or a release of the connection between the extension portion 400 and the bonding member 600 may achieve a release of the connection between the clipping portions 310 and the extension portion 400. By providing the bonding member 600, the stability of the connection between the clipping portions 310 and the extension portion 400 may be improved.

As shown in FIG. 5, FIG. 8, and FIG. 9, in some embodiments, the bonding member 600 may include a first bonding portion 610 and a second bonding portion 620, the distal end of the extension portion 400 may include a first docking portion 450, and at least one of the clipping portions 310 may include a second docking portion 350, the first bonding portion 610 may be releasably connected to the first docking portion 450, and the second bonding portion 620 may mate with the second docking portion 350. In some embodiments, the second bonding portion 620 may detachably mate with the second docking portion 350, e.g., plugged in, snapped together, etc. In some embodiments, the second bonding portion 620 does not detachably mate with the second docking portion 350, e.g., mating by welding, etc.

In some embodiments, the first bonding portion 610 and/or the first docking portion 450 may deform, fracture, or displace under a force, and the clipping portions 310 and the extension portion 400 may be released. When the extension portion 400 is moved from the distal end to the proximal end, the first docking portion 450 applies a force from the distal end to the proximal end to the first bonding portion 610. When the force reaches a preset force value, the first docking portion 450 and the first bonding portion 610 are released, thereby releasing the clipping portions 310 and the extension portion 400.

As shown in FIG. 4, FIG. 5, FIG. 8, and FIG. 9, in some embodiments, the clip apparatus 10 may include a plurality of bonding members 600, with each clipping portion 310 of at least two clip devices 300 provided with at least one bonding member 600. Exemplarily, the first clip device 300A is provided with a first bonding member 600A, the second clip device 300B is provided with a second bonding member 600B, and the third clip device 300C is provided with a third bonding member 600C. The extension portion 400 is moved from a distal end to a proximal end, and after the first docking portion 450 of the extension portion 400 is released from the first bonding portion 610 of the first bonding member 600A, the first docking portion 450 enters into the second clip device 300B and is releasably connected to the first bonding portion 610 of the second bonding member 600B. After the first docking portion 450 of the extension portion 400 is released from the first bonding portion 610 of the second bonding member 600B, the first docking portion 450 enters into the third clip device 300C and is releasably connected to the first bonding portion 610 of the third bonding member 600C.

In some embodiments, the first docking portion 450 of the extension portion 400 may include a first groove provided on the bonding portion at the distal end 410 of the extension portion 400, and the first groove may include, but is not limited to, a countersunk groove, an aperture groove, etc. The first bonding portion 610 of the connecting member 700 may include a bending structure. The first groove and the bending structure are releasably limitedly connected. In some embodiments, the first groove and the bending structure are limitedly connected to limit an axial relative displacement of the extension portion 400 and the bonding member 600, at this time, the extension portion 400 is connected to the bonding member 600. The bending structure may be released from the first groove by deformation, fracture, and displacement when subjected to a force from a distal end to a proximal end, at this time, the extension portion 400 is released from the bonding member 600.

In some embodiments, the bending structure of the bonding member 600, or all of the bonding member 600, is made of an elastic material, so that the bending structure may adaptively deform when the extension portion 400 is moved by an external force, thereby allowing the bending structure to enter the first groove and realize the connection between the first groove and the bending structure, or causing the bending structure to disengage from the first groove to achieve a release of the connection between the first groove and the bending structure.

In some embodiments, the bending structure is bent in a smooth transition bending in a circular arc shape, avoiding a phenomenon of stress concentration, and preventing the phenomenon of fracture of the bending structure caused by external force.

In some embodiments, the bending structure may be formed by performing processing, e.g., mechanical cutting and bending deformation, on the bonding member 600. In some embodiments, the bending structure may be formed on the bonding member 600 through bonding or welding.

In some embodiments, the second bonding portion 620 of the bonding member 600 may include a deformation portion 621, the second docking portion 350 of the clipping portion 310 may include a slot, the deformation portion 621 may limitedly mate with the slot, and the bonding member 600 may be connected to the clipping portion 310. In some embodiments, the deformation portion 621 may include two stand bars, at least a portion of the two stand bars is resilient, and the two stand bars may be deformed outward relative to a central axis of the bonding member 600 when subjected to a force. In some embodiments, a rounded transition may be used at distal ends of the two stand bars to avoid cracking of the deformation portion 621 when subjected to an external force.

In some embodiments, the deformation portion 621 may include a first bevel 622 radially outward inclined from a distal end to a proximal end, and the second docking portion 350 of the clipping portion 310 may include a second bevel 351 parallel or substantially parallel to the first bevel 622. Being substantially parallel refers to that an included angle between the first bevel 622 and the second bevel 351 is within a range of 0-5°. When the bonding member 600 is subjected to a force from a distal end to a proximal end, the first bevel 622 abuts against the second bevel 351, and the second bevel 351 may guide the deformation portion 621 to deform outward along a radial direction. Descriptions regarding the process of the first bevel 622 mating with the second bevel 351 may be found in FIG. 11B and related descriptions thereof.

As shown in FIG. 5 and FIG. 9, in some embodiments, the clipping portion 310 may be provided with a first snap portion 360, the extension portion 400 may be provided with a second snap portion 470, and the first snap portion 360 may be releasably connected to the second snap portion 470. The first snap portion 360 is releasably connected to the second snap portion 470, which realizes a temporary connection between the extension portion 400 and the clipping portions 310 and improves relative stability of the extension portion 400 and the clipping portions 310.

In some embodiments, the second snap portion 470 may be provided on the bonding portion at the distal 410 of the extension portion 400. In some embodiments, the second snap portion 470 may be switchably connected to one of the plurality of clipping portions 310. For example, after the second snap portion 470 is released from the first snap portion 360 of the first clipping portion 310A, the extension portion 400 is moved from a distal end to a proximal end such that the second snap portion 470 is connected to the first snap portion 360 of the second clipping portion 310B. After the second snap portion 470 is connected to the second clipping portion 310B, the extension portion 400 is moved from the proximal end to the distal end, which may drive two support arms of the second clipping portion 310B to separate from each other and open, thereby facilitating the clipping the tissue again.

In some embodiments, the first snap portion 360 may include a second groove, and the second snap portion 470 may include a resilient projection. In some embodiments, a proximal sidewall of the second groove may be inclined from inward to outward toward the distal end of the clipping portions 310, and the resilient projection may be an oblique projection that is inclined at the same or substantially the same angle as the proximal sidewall of the second groove. When the extension portion 400 is moved from the distal end to the proximal end, a proximal end sidewall of the second groove may be oriented for the oblique projection, which may reduce resistance to the oblique projection when the oblique projection is deformed or displaced. A side of the oblique projection close to the extension portion 400 has a certain deformation space, which facilitates the deformation or restoration of the oblique projection to its original state. In some embodiments, a distal end of the resilient projection is connected to the extension portion 400, and a proximal end of the resilient projection is inclined relative to the extension portion 400 to form a free end. When the extension portion 400 is moved from the distal end to the proximal end, the resilient projection is extruded and deformed to be dislodged from the second groove. When the extension portion 400 is moved from the proximal end to the distal end, the resilient projection abuts against the sidewall of the second groove and is not easily dislodged from the second groove, so that the clipping portions 310 remain on the extension portion 400.

In some embodiments, when the second snap portion 470 is connected to the first snap portion 360 of the first clipping portion 310A, the extension portion 400 is moved from the distal end to the proximal end, and the second snap portion 470 deforms or displaces and is dislodged from the first snap portion 360. The second snap portion 470, after being dislodged, continues to be compressed by the extrusion of the extension portion 400 and the clipping portion 310, thereby avoiding affecting the movement of the extension portion 400. When the second snap portion 470 is moved to the first snap portion 360 of the second clipping portion 310B, the second snap portion 470 returns to its original shape under the action of the elasticity, i.e., the resilient projection extends into the second groove to make the first snap portion 360 releasably connected to the second snap portion 470. In some embodiments, the first snap portion 360 may include other structures, and the second snap portion 470 may include other structures, which are not limited in the embodiments of the present disclosure.

Figure 10:
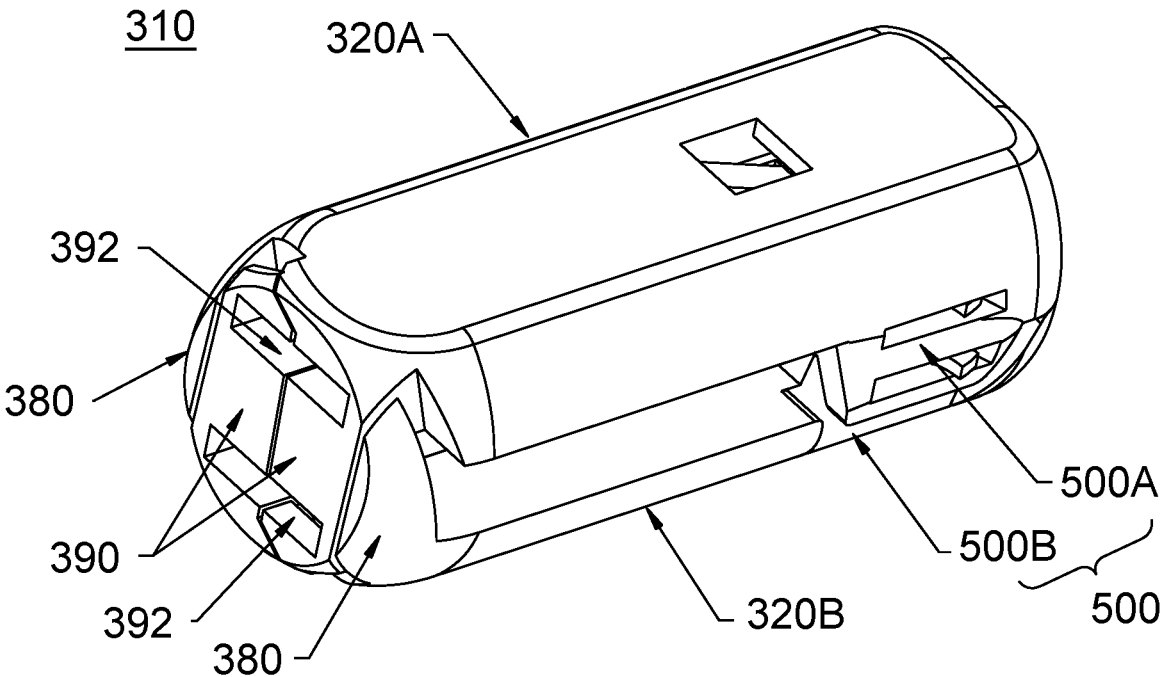
FIG. 10 is an exemplary diagram illustrating a structure of a clipping portion according to some embodiments of the present disclosure.

FIG. 10 is an exemplary diagram illustrating a structure of a clipping portion according to some embodiments of the present disclosure.

As shown in FIG. 7, FIG. 9, and FIG. 10, in some embodiments, the clipping portion 310 may include a first clipping arm 320A, a second clipping arm 320B, and a locking portion 500. The locking portion 500 may include a first locking portion 500A provided on the first clipping arm 320A and a second locking portion 500B provided on the second clipping arm 320B. The first locking portion 500A may include a locking convexity 510 and the second locking portion 500B may include a locking concavity 520. When the first clipping arm 320A and the second clipping arm 320B are in a closed state, the locking convexity 510 may mate with the locking concavity 520, and the first clipping arm 320A and the second clipping arm 320B are locked with each other.

In some embodiments, each side of the first clipping arm 320A may include the locking convexity 510, and each side of the second clipping arm 320B may include the locking concavity 520, and when the two locking convexities 510 mate with the two locking concavities 520, the first clipping arm 320A and the second clipping arm 320B are locked to each other.

In some embodiments, the first clipping arm 320A may include a locking convexity 510 and a locking concavity 520 on both sides, respectively, of the first clipping arm 320A, and the second clipping arm 320B may include a locking concavity 520 and a locking convexity 510 on both sides, respectively, of the second clipping arm 320B. When the locking convexities 510 mate with the locking concavities 520, the first clipping arm 320A and the second clipping arm 320B lock with each other.

In some embodiments, the locking convexity 510 may include a locking block, and the locking concavity 520 may include a locking slot. In some embodiments, the locking block is inclined outward radially relative to an outer surface of the clipping arm 320, one end of the locking block is fixed to the outer surface of the clipping arm 320, and the other end is formed as a free end. The locking slot may be an aperture, a slot, or other structure on the clipping arm 320, which is capable of accommodating the locking block, and the free end of the locking block may be extended into the locking slot and formed into a limiting snap connection with the inner wall of the locking slot, to achieve a locking between the locking convexity 510 and the locking concavity 520.

In some embodiments, the locking convexity 510 is constructed as a limiting clasp, and the locking concavity 520 is constructed as a catch. In some embodiments, one end of the limiting clasp is fixed to the clipping arm 320, and the other end of the limiting clasp is formed as a snap end with an increased cross-section. The catch may be a limiting slot formed by a combination of two support arms. The snap end of the limiting clasp extends into the catch to form a snap fit, and the locking convexity 510 locks with the locking concavity 520.

In some embodiments, the locking portion 500 may be integrally molded with the clipping portions 310. In some embodiments, the locking portion 500 may be molded separately from the clipping portions 310. In some embodiments, the locking convexity 510 and the locking concavity 520 may be constructed in other structures.

As shown in FIGS. 7-10, in some embodiments, the deformation portion 621 of the bonding member 600 has a locking effect on two clipping arms 320 of the clipping portions 310. In some embodiments, the clipping portions 310 may include a first locking slot 511 provided on the locking convexity 510, a second locking slot 512 provided on the locking convexity 510, and a third locking slot 521 provided on the locking concavity 520. When the first clipping arm 320A and the second clipping arm 320B are closed, the second locking slot 512 of the first clipping arm 320A may be connected to the third locking slot 521 of the second clipping arm 320B. The extension portion 400 may be moved from a distal end to a proximal end, causing the deformation portion 621 of the bonding member 600 to deform or be displaced, one of the stand bars of the deformation portion 621 may extend into the first locking slot 511, and the other of the stand bars may simultaneously extend into the second locking slot 512 and the third locking slot 521. At this time, the first clipping arm 320A and the second clipping arm 320B may be locked. In some embodiments, when the clipping portion 310 is released from the extension portion 400, the deformation portion 621 of the bonding member 600 is maintained in a post-deformation state, so that the clipping portion 310, which stays in the body, remains locked.

In some embodiments, the first locking slot 511 and the third locking slot 521 may form a slot of the second docking portion 350, and when the bonding member 600 is not deformed, the two stand bars of the deformation portion 621 of the bonding member 600 may be inserted respectively in the first locking slot 511 and the third locking slot 521 in an original form.

In some embodiments, the clipping arm 320 may include an accommodating slot 370 that extends axially from a distal end of the clipping arm 320 to a through slot at the proximal end of the clipping arm 320, with the extension portion 400 axially movable provided in the accommodating slot 370.

In some embodiments, the clipping arm 320 may include a projection of a first distal end 380 and a projection of a second distal end 390, the projection of the first distal end 380 is spaced apart from the projection of the second distal end 390. In some embodiments, when the two clipping arms 320 are closed, the projection of the second distal end 390 of the first clipping arm 320A is inserted between the projection of the first distal end 380 and the projection of the second distal end 390 of the second clipping arm 320B. The projection of the second distal end 390 of the second clipping arm 320B is inserted between the projection of the first distal end 380 and the projection of the second distal end 390 of the first clipping arm 320A. Thus, as shown in FIG. 10, an end surface of the distal end of the clipping portion 310 is formed. By providing the projection of the first distal end 380 and the projection of the second distal end 390, it is possible to assist in positioning the distal ends of the two clipping arms 320 when closed to improve the docking accuracy of the two clipping arms 320 when closed. Moreover, after the two clipping arms 320 are closed, the projection of the first distal end 380 and the projection of the second distal end 390 may form a mutual limitation, preventing the two clipping arms 320 from being misaligned or moving towards each other, and improving the stability of the closure of the clipping arms 320.

In some embodiments, after the first clipping arm 320A and the second clipping arm 320B are docked, an inner end surface formed by the docking of two projections of the second distal ends 390 is constructed as a second mating portion 340 of the clipping portion 310, and the second mating portion 340 may mate with the connecting member 700 of the second connecting portion 720.

As shown in FIG. 9, in some embodiments, a notch 391 is formed on the projection of the second distal end 390 to allow the extension portion 400 and the connecting member 700 to pass through. When the two clipping arms 320 are closed, as shown in FIG. 10, the notches 391 of the projections of the second distal ends 390 of the two clipping arms 320 are aligned to form a passing hole 392 that allows the extension portion 400 and the connecting member 700 to pass through.

Figure 11A:
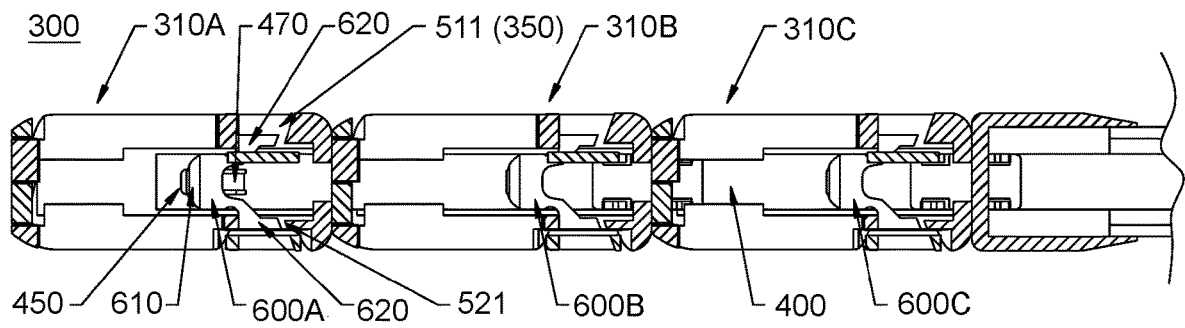
FIG. 11A-FIG. 11C are schematic diagrams illustrating a changing process of a bonding member when clipping portions are released according to some embodiments of the present disclosure.
Figure 11B:
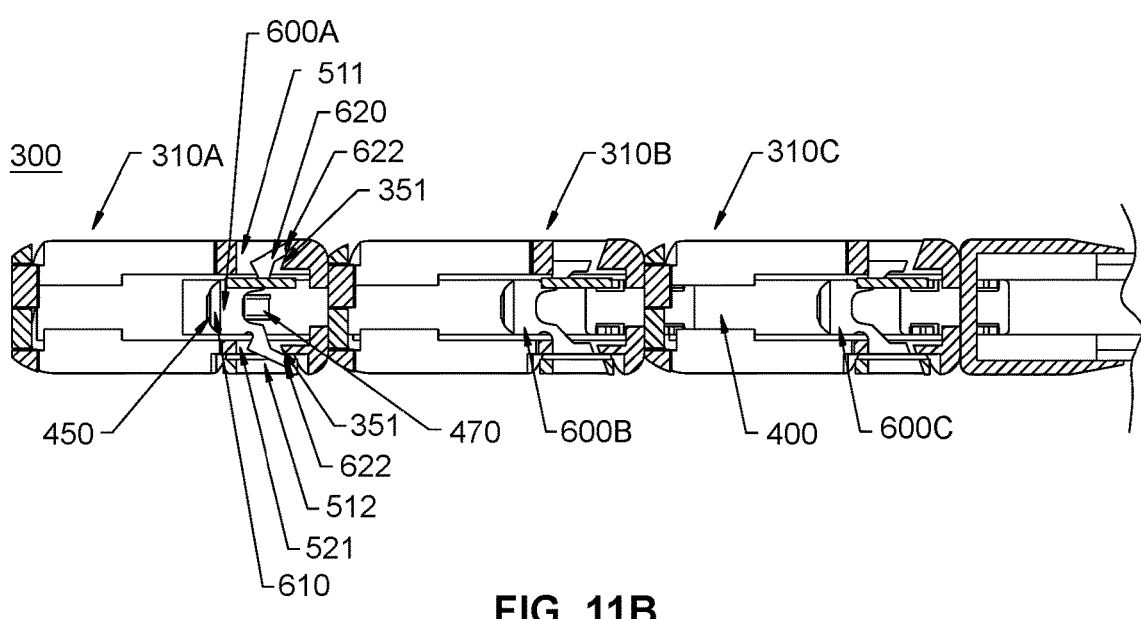
Figure 11C:
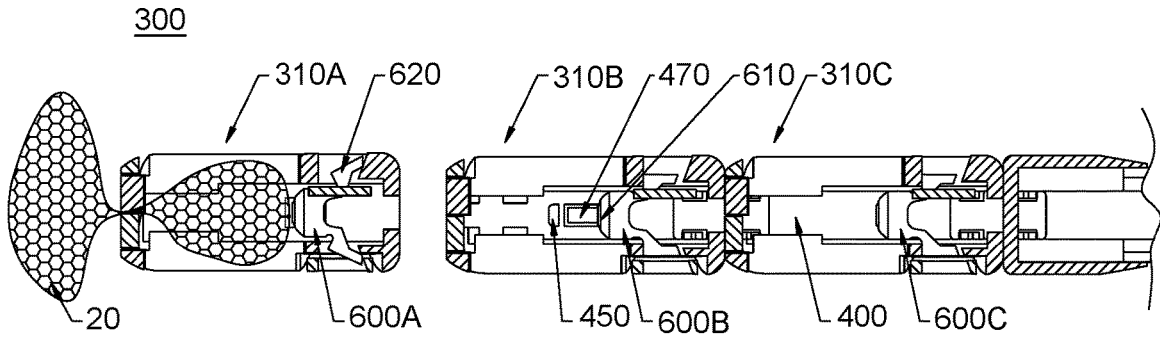

FIG. 11A-FIG. 11C are schematic diagrams illustrating a changing process of a bonding member when clipping portions are released according to some embodiments of the present disclosure. Taking the clip apparatus 10 including three clip devices 300 as an example, the three clip devices 300 respectively include a first clipping portion 310A, a second clipping portion 310B, and a third clipping portion 310C, and the bonding member 600 may include the first bonding member 600A provided on the first clipping portion 310A, the second bonding member 600B provided on the second clipping portion 310B, and the third bonding member 600C provided on the third clipping portion 310C. A count of the clip devices 300 in the embodiment is for illustrative purposes only and does not limit a count of clipping portions 310 in the embodiments of the present disclosure. For a clip apparatus 10 with a different count of clip devices 300, please refer to the clipping process shown in FIGS. 11A-11C.

As shown in FIG. 11A, in some embodiments, the first clipping portion 310A, the second clipping portion 310B, and the third clipping portion 310C are all in a closed and connected state. The first docking portion 450 of the extension portion 400 may mate with the first bonding portion 610 of the first bonding member 600A, and the second bonding portion 620 of the first bonding member 600A may mate with the second docking portion 350 of the first clipping portion 310A. In some embodiments, one stand bar of the second bonding portion 620 of the first bonding member 600A may mate with the first locking slot 511 of the first clipping portion 310A, and the other stand bar may mate with the third locking slot 521 of the first clipping portion 310A, at this time, the two stand bars of the second bonding portion 620 are not deformed. In some embodiments, the first snap portion 360 of the first clipping portion 310A (as illustrated in FIG. 9) may mate with the second snap portion 470 of the extension portion 400.

As shown in FIG. 11B, in some embodiments, the first clipping portion 310A, the second clipping portion 310B, and the third clipping portion 310C are all in a closed and connected state. The extension portion 400 is moved from a distal end to a proximal end so that the first bonding member 600A is subjected to a force from the distal end to the proximal end. In some embodiments, a first bevel 622 of the second bonding portion 620 of the first bonding member 600A abuts against a second bevel 351 of the first clipping portion 310A, and the second bevel 351 guides the second bonding portion 620 to deform the two stand bars of the second bonding portion 620 radially outward so that one of the two stand bars may mate with the first locking slot 511 of the first clipping portion 310A, and the other one of the two stand bars may mate with the second locking slot 512 and the third locking slot 521 of the first clipping portion 310A, thereby locking the two clipping arms 320 of the first clipping portion 310A. In some embodiments, when the force exerted by the extension portion 400 on the first bonding member 600A reaches a predetermined force value, the first bonding portion 610 of the first bonding member 600A may be released from the first docking portion 450 of the extension portion 400 due to deformation, fracture, or displacement. In some embodiments, the first snap portion 360 of the first clipping portion 310A may be released from the second snap portion 470 of the extension portion 400. After the above process, a release of the connection between the extension portion 400 to the first clipping portion 310A may be achieved.

As shown in FIG. 11C, in some embodiments, a release of the connection between the first clipping portion 310A and the second clipping portion 310B may be achieved. In some embodiments, the second bonding portion 620 of the first bonding member 600A is maintained in a post-deformation state so that the first clipping portion 310A stays in the body in a closed state after clipping the tissue 20. In some embodiments, the extension portion 400 continues to move from a distal end to a proximal end, and the second snap portion 470 of the extension portion 400 may mate with the first snap portion 360 of the second clipping portion 310B. The first bonding portion 610 of the second bonding member 600B may mate with the first docking portion 450 of the extension portion 400.

FIG. 12A-FIG. 12E are schematic diagrams illustrating a changing process of a connecting member when clipping portions are released according to some embodiments of the present disclosure. Taking the clip apparatus 10 including three clip devices 300 as an example, the three clip devices 300 respectively include the first clipping portion 310A, the second clipping portion 310B, and the third clipping portion 310C. The connecting member 700 may include the first connecting member 700A and the second connecting member 700B, the first connecting member 700A connects the second clipping portion 310B and the third clipping portion 310C, and the second connecting member 700B connects the third clipping portion 310C and the sheath pipe 210. A count of clip devices 300 in the embodiment is for illustrative purposes only and does not limit a count of clipping portions 310 in the embodiments of the present disclosure. For a clip apparatus 10 with a different count of clip devices 300, please refer to the clipping process shown in FIG. 12A-FIG. 12E.

Figure 12A:
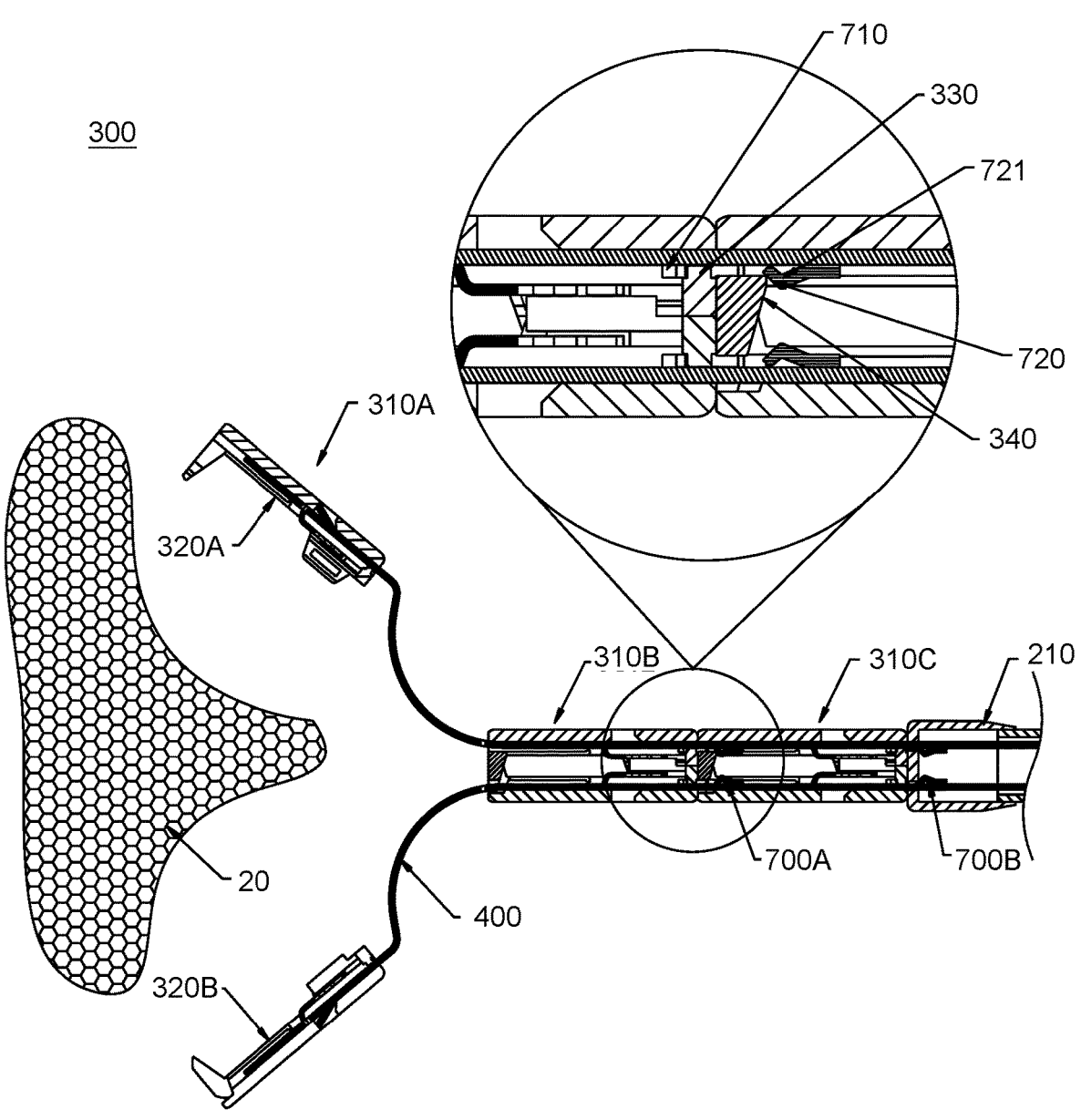
FIG. 12A-FIG. 12E are schematic diagrams illustrating a changing process of a connecting member when clipping portions are released according to some embodiments of the present disclosure.

As shown in FIG. 12A, in some embodiments, the first clipping portion 310A is in an opening state, and the second clipping portion 310B and the third clipping portion 310C are both in a closed and connected state. The extension portion 400 is moved from a proximal end to a distal end, and the first clipping arm 320A and the second clipping arm 320B of the first clipping portion 310A move away from each other and form a clipping space for clipping the tissue 20. In some embodiments, the first connecting portion 710 of the first connecting member 700A may mate with the first mating portion 330 of the second clipping portion 310B, and the tab 721 of the first connecting member 700A may be extruded and deformed, causing the second connecting portion 720 to mate with the second mating portion 340 of the third clipping portion 310C. The first connecting portion 710 of the second connecting member 700B may mate with the first mating portion 330 of the third clipping portion 310C, and the second connecting portion 720 of the second connecting member 700B may be extruded and deformed and may mate with the second mating portion 340 of the sheath pipe 210.

Figure 12B:
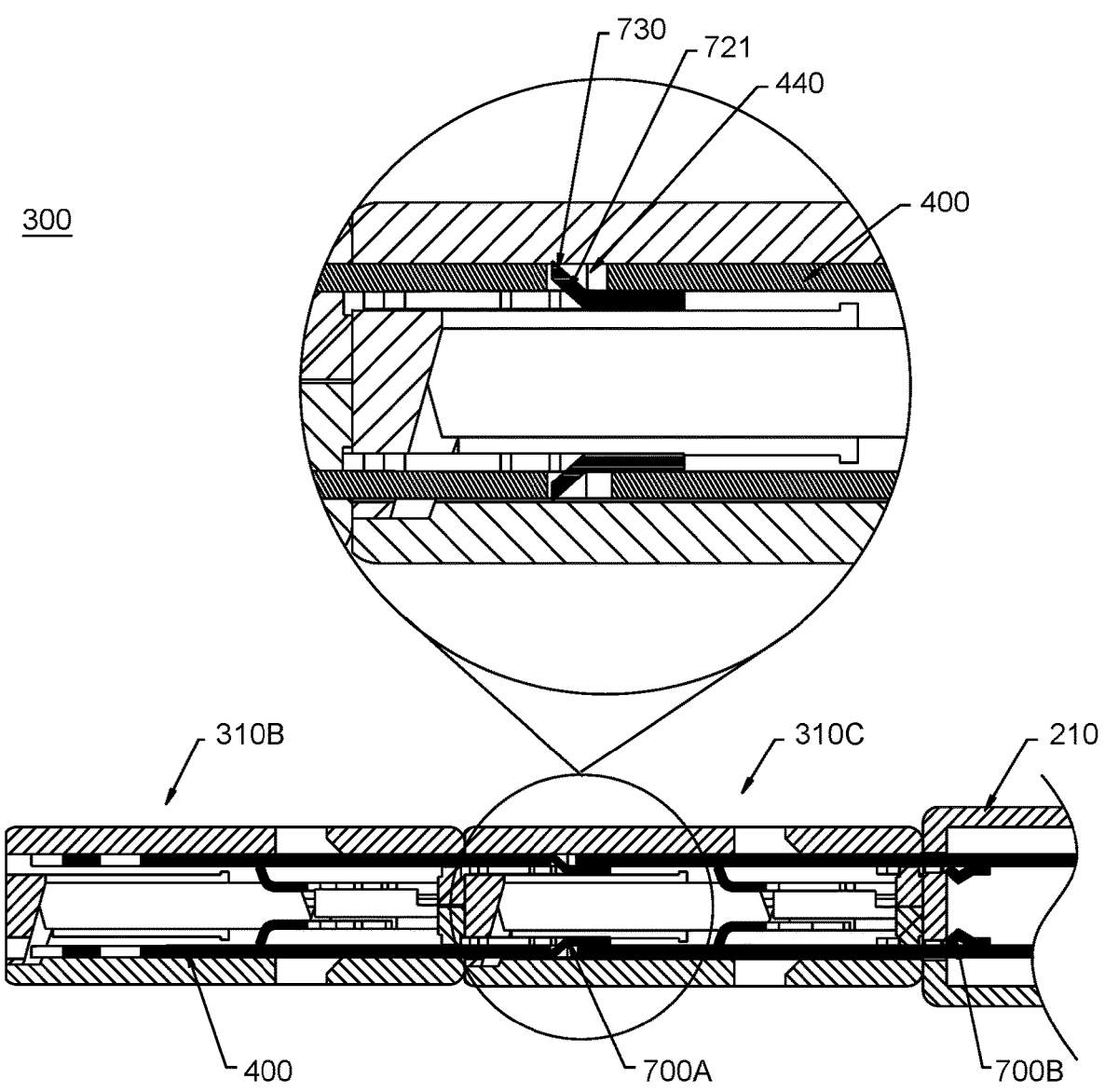

As shown in FIG. 12B, in some embodiments, the first clipping portion 310A is released from the second clipping portion 310B, and both the second clipping portion 310B and the third clipping portion 310C are in a closed and connected state. After released from the first clipping portion 310A, the extension portion 400 continues to move from the distal end to the proximal end, such that the third mating portion 440 of the extension portion 400 may be moved to the second connecting portion 720 of the first connecting member 700A, the tab 721 of the first connecting member 700A may be released from extrusion and returns to its original shape under the elastic force, a release of the mating of the second connecting portion 720 and the second mating portion 340 of the third clipping portion 310C may be achieved, and the third connecting portion 730 formed by the free end of the tab 721 may extend to mate with the third mating portion 440 of the extension portion 400.

Figure 12C:
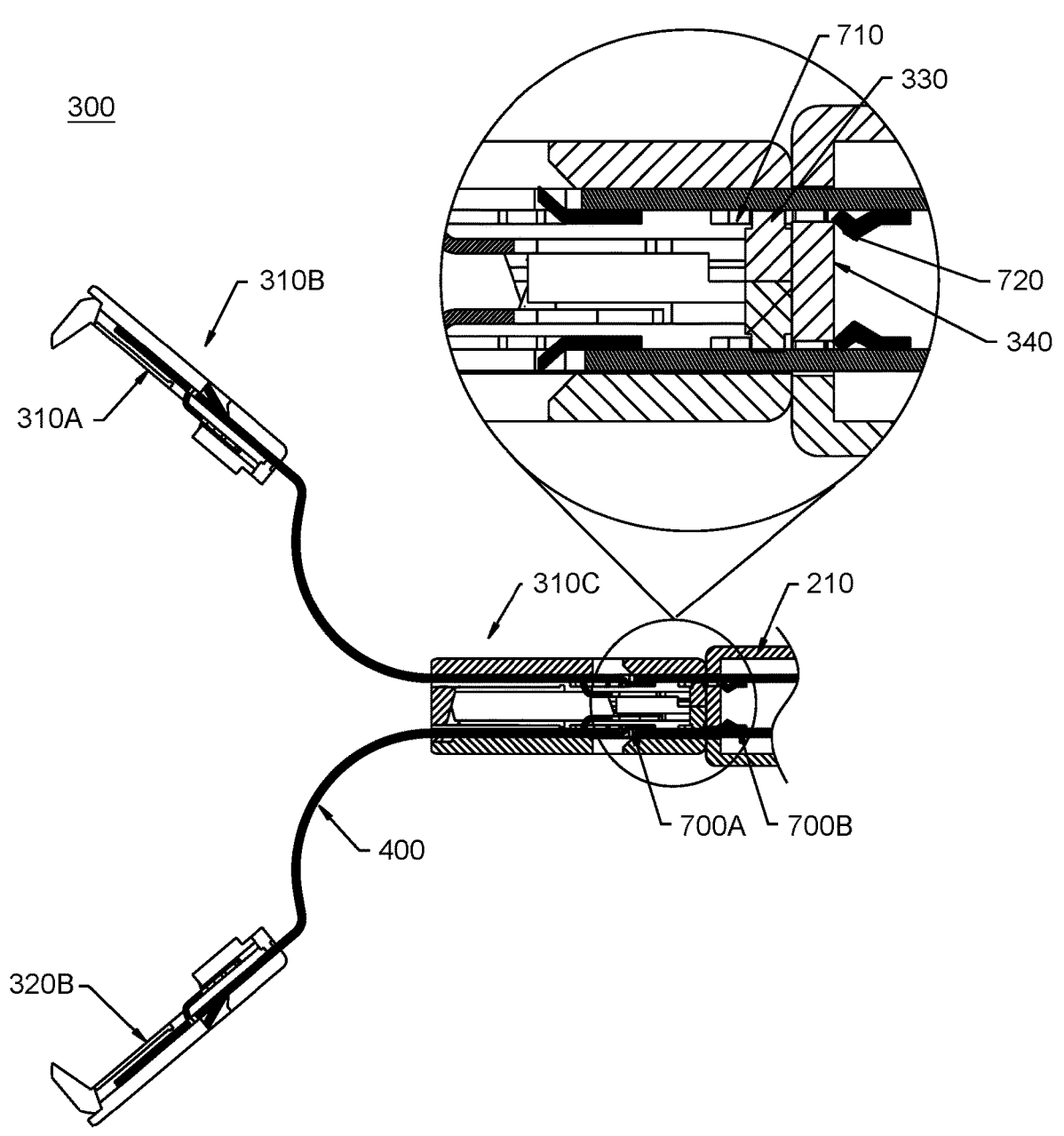

As shown in FIG. 12C, in some embodiments, the second clipping portion 310B is in the opening state and the third clipping portion 310C is in the closed state. The extension portion 400 is moved from the distal end to the proximal end, driving the first connecting member 700A to move into the third clipping portion 310C to achieve a release of the connection between the second clipping portion 310B and the third clipping portion 310C. The extension portion 400 is moved from the proximal end to the distal end. Under the action of the curved portion 420 of the extension portion 400, the first clipping arm 320A and the second clipping arm 320B of the second clipping portion 310B may move away from each other and form a clipping space for clipping the tissue 20.

Figure 12D:
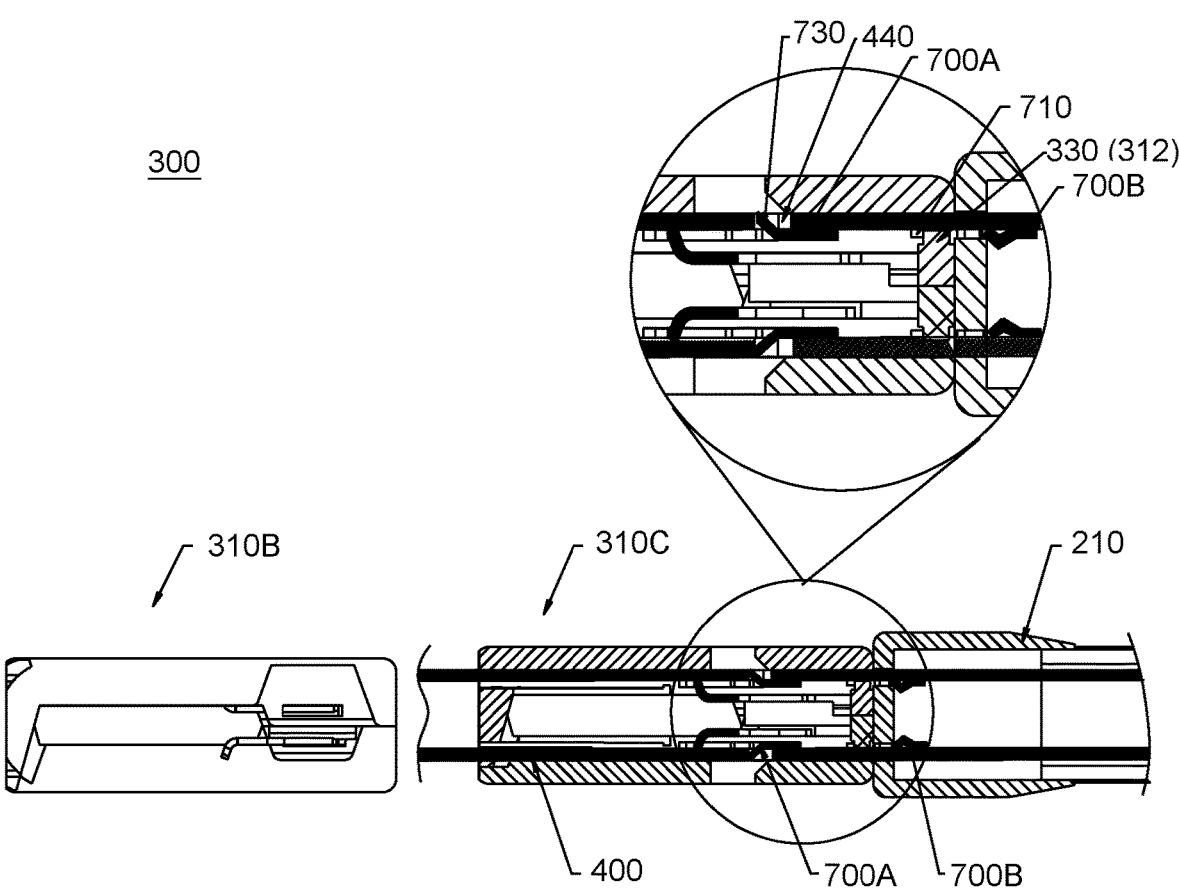

As shown in FIG. 12D, in some embodiments, the second clipping portion 310B is locked and then released from the extension portion 400, and the third clipping portion 310C is in the closed state. The extension portion 400 is moved from the distal end to the proximal end, driving a proximal end of the first connecting member 700A to abut against a distal end of the second connecting member 700B, achieving a release of the mating of the first connecting portion 710 of the second connecting member 700B and the first mating portion 330 of the third clipping portion 310C, and the third clipping portion 310C is released from the sheath pipe 210. At this time, the proximal end of the first connecting member 700A abuts against the resisting portion 312 of the third clipping portion 310C, the extension portion 400 continues to be moved from the distal end to the proximal end, the third connecting portion 730 of the first connecting member 700A deforms or displaces and disengages from the third mating portion 440 of the extension portion 400, and the first connecting member 700A stays within the third clipping portion 310C.

Figure 12E:
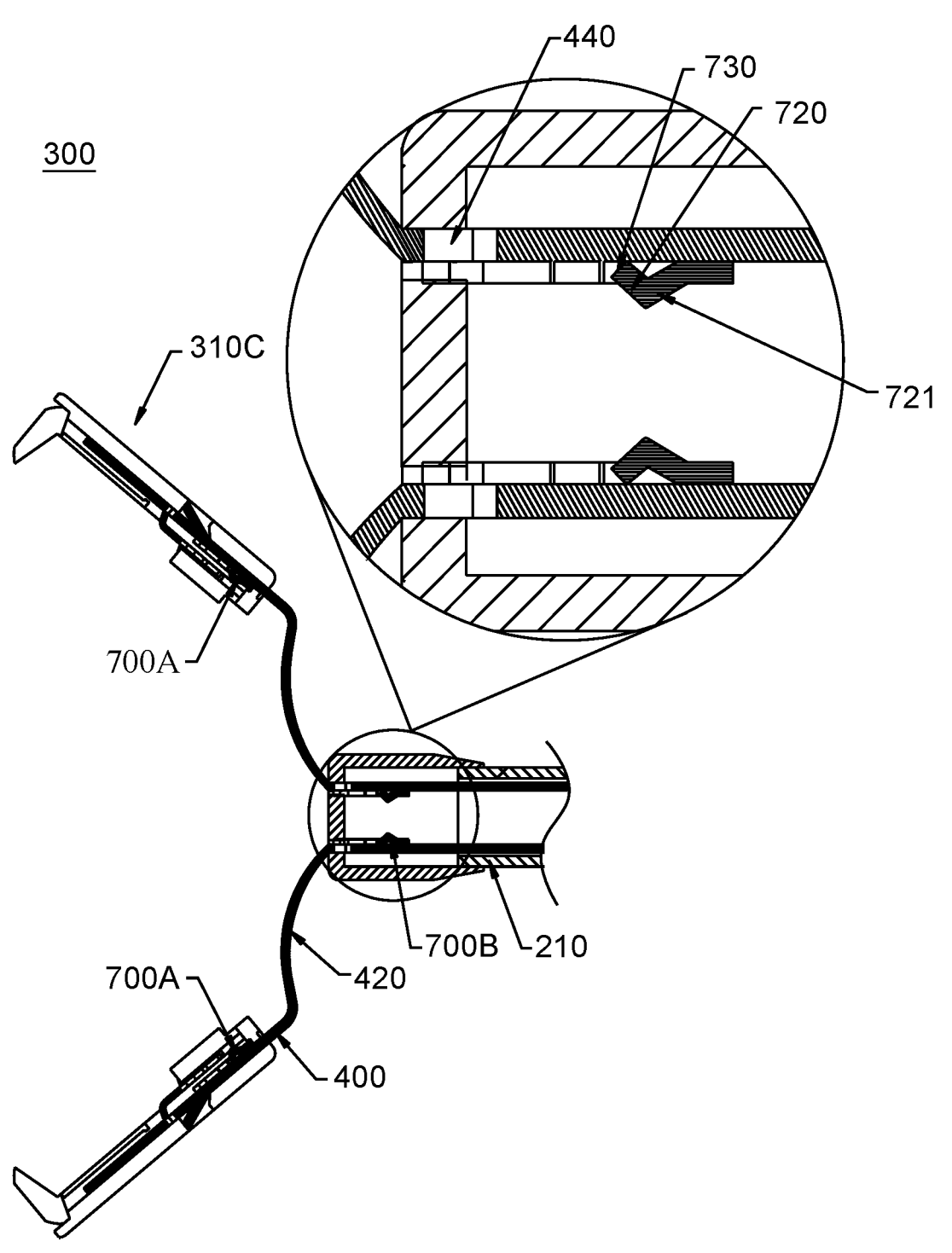

As shown in FIG. 12E, in some embodiments, the third clipping portion 310C is in the opening state. The extension portion 400 is moved from the proximal end to the distal end, and under the action of the curved portion 420 of the extension portion 400, the first clipping arm 320A and the second clipping arm 320B of the second clipping portion 310B move away from each other and form a clipping space for clipping the tissue 20. In some embodiments, the extension portion 400 is moved from the distal end to the proximal end, the third mating portion 440 of the extension portion 400 is moved to a position of the second connecting portion 720 of the second connecting member 700B, and the tab 721 of the second connecting member 700B is released from extrusion and returns to its original shape under the action of the elastic force, and the third connecting portion 730 formed after the free end of the tab 721 extends into and mates with the third mating portion 440 of the extension portion 400. In some embodiments, the extension portion 400 continues to be moved from the distal end to the proximal end, and the first clipping arm 320A and the second clipping arm 320B of the third clipping portion 310C are locked after being closed and released from the extension portion 400. The extension portion 400 drives the second connecting member 700B to move into the sheath pipe 210.

The clip apparatus 10 of example two may be described in detail below in conjunction with FIGS. 13-15C. In the following, differences between the clip apparatus 10 in example two and the clip apparatus 10 in example one in the present disclosure may be described, and the same portions may be referred to in the description of example one, which may not be repeated in the present disclosure.

Figure 13:
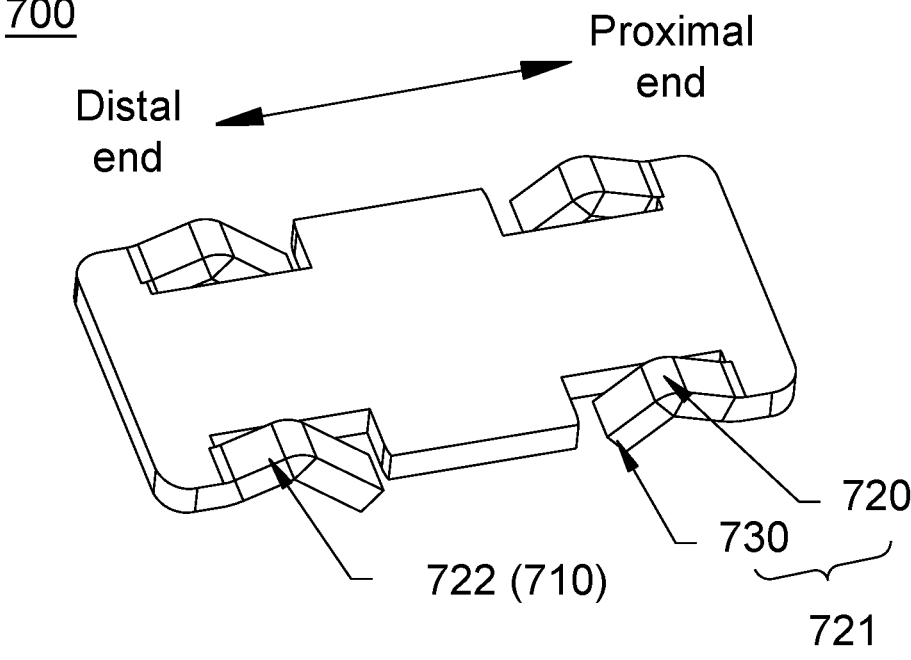
FIG. 13 is an exemplary diagram illustrating a structure of a connecting member according to some embodiments of the present disclosure.
Figure 14:
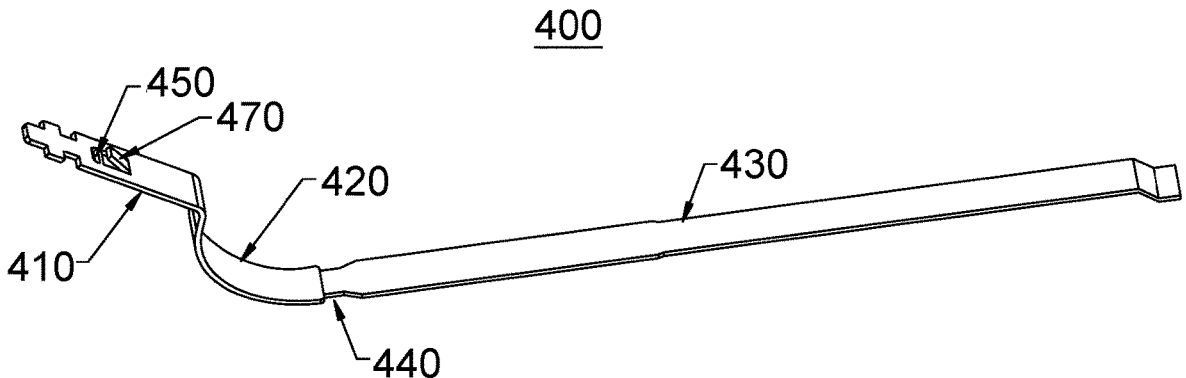
FIG. 14 is an exemplary diagram illustrating a structure of an extension portion according to some embodiments of the present disclosure.

FIG. 13 is an exemplary diagram illustrating a structure of a connecting member according to some embodiments of the present disclosure. FIG. 14 is an exemplary diagram illustrating a structure of an extension position according to some embodiments of the present disclosure.

As shown in FIG. 9 and FIG. 13, in some embodiments, the connecting member 700 is constructed as a tabular structure to minimize a radial space that the connecting member 700 occupies in the clipping portion 310. In some embodiments, the connecting member 700 is constructed in other structures such as an elongated structure, which is not limited in the present disclosure.

In some embodiments, the first connecting portion 710 may include a tongue piece 722, the tongue piece 722 is provided on a distal end of the connecting member 700, and the first mating portion 330 of the clipping portion 310 may include a stop surface, which is provided on a proximal end of the clipping portion 310. In some embodiments, the tongue piece 722 may mate with the stop surface such that the first connecting portion 710 may mate with the first mating portion 330. In some embodiments, deformation or displacement of the tongue piece 722 by a force achieves a release of the mating of the tongue piece 722 and the stop surface to achieve a release of the mating of the first connecting portion 710 and the first mating portion 330.

In some embodiments, the tongue piece 722 is flexible. In some embodiments, the tongue piece 722 is constructed in an arch shape or V-shape, with a distal end of the tongue piece 722 connected to a distal end of the connecting member 700, and a proximal end of the tongue piece 722 is formed as a free end toward a proximal end of the connecting member 700. In some embodiments, at least a portion of an upper arched surface of the tongue piece 722 protrudes from a surface of the connecting member 700 to mate with the stop surface to limit the connecting member 700 from moving from the distal end to the proximal end, the upper arched surface returns to its original shape to achieve a release of the mating with the stop surface when the tongue piece 722 is released from a force. When the connecting member 700 is moved from the distal end to the proximal end, the upper arched surface of the tongue piece 722 is squeezed by the stop surface and deformed or dislocates the tongue piece 722 to be disengaged from the stop surface. In some embodiments, there are two tongue pieces 722 provided on both sides of the distal end of the connecting member 700 along a length direction.

In some embodiments, the connecting member 700 may include the tab 721 constructed as a resilient arch shape or V-shape, one end of the tab 721 is connected to the proximal end of the connecting member 700, and another end is formed toward the distal end of the connecting member 700 as a free end, and the upper arched surface of the tab 721 is constructed as the second connecting portion 720. In some embodiments, the second mating portion 340 of the clipping portion 310 may include a limit surface. The outer arched surface of the tab 721 may mate with the limit surface to achieve a mating between the second connecting portion 720 and the second mating portion 340. A release of the mating of the outer arched surface of the tab 721 and the limit surface achieves a release of the mating of the second connecting portion 720 and the second mating portion 340. In some embodiments, there are two tongue pieces 722 provided on both sides of the proximal end of the connecting member 700 along the length direction.

In some embodiments, the tab 721 is deformed by a force in a thickness direction of the connecting member 700, and the deformation of the tab 721 makes the second connecting portion 720 (i.e., the outer arched surface) protrude out from the surface of the connecting member 700 in the thickness direction, causing the outer arched surface to mate with the limit surface and to return to its original shape to achieve a released of the mating with the limit surface when the tab 721 is released from the force.

In some embodiments, the connecting member 700 may include the third connecting portion 730. The connecting member 700 achieves a release of the connection between at least one clipping portion 310 and at least one of the rest of the clipping portions 310 and/or a release of the connection between the at least one clipping portion 310 and the sheath pipe 210 when the third connecting portion 730 is subjected to a force that satisfies a preset condition. In some embodiments, the preset condition may include that the third connecting portion 730 is subjected to a force from a distal end to a proximal end, and the force reaches a preset threshold. When the preset condition is met, an operating force provided by the extension portion 400 on the third connecting portion 730 is greater than the preset threshold, which may cause the tab 721 to deform, thereby changing the shape or state of the second connecting portion 720 and achieving a release of the mating of the second connecting portion 720 and the second mating portion 340. Subsequently, the extension portion 400 may drive the third connecting portion 730 to move from the distal end to the proximal end. When the third connecting portion 730 is moved from the distal end to the proximal end, a release of the mating of the first connecting portion 710 of the connecting member 700 and the first mating portion 330 of the clipping portions 310 is achieved to achieve a release of the connection between two adjacent clipping portions 310 and/or a release of the connection between the clipping portions 310 and the sheath pipe 210.

In some embodiments, the third connecting portion 730 and the second connecting portion 720 are integrally molded, and the second connecting portion 720 is deformed or displaced to form the third connecting portion 730. In some embodiments, the connecting member 700 may include the tab 721, one end of the tab 721 is connected to the proximal end of the connecting member 700, the other end is formed towards the distal end of the connecting member 700 as a free end, and the free end is constructed to be the third connecting portion 730.

As shown in FIG. 13 and FIG. 14, in some embodiments, the extension portion 400 provides an operating force for the third connecting portion 730. The extension portion 400 may include the third mating portion 440, which is releasably connected to the third connecting portion 730. In some embodiments, the bonding portion at the proximal end 430 of the extension portion 400 is provided with a slot on each radial side, and the slot is constructed to be the third mating portion 440.

In some embodiments, the tab 721 is constructed as a resilient arch. When the connecting member 700 is provided in the clipping portion 310 or the sheath pipe 210, in the thickness direction of the connecting member 700, the tab 721 is deformed by squeezing so that the second connecting portion 720 may mate with the second mating portion 340 of the clipping portion 310. When the extension portion 400 is moved to make the free end of the tab 721 extend into the slot of the third mating portion 440, a squeezing force on the tab 721 is released and the tab 721 returns to its original shape, so that the third mating portion 440 protrudes out from the surface of the connecting member 700, and the third mating portion 440 of the extension portion 400 may mate with the third connecting portion 730 of the tab 721.

In some embodiments, the proximal end of the clipping portion 310 may also be provided with an accommodating slot 370 that accommodates the tongue piece 722 and squeezes the tongue piece 722, which creates friction between the tongue piece 722 and the clipping portion 310.

The connecting member 700 may be releasably limitedly connected by friction between the tongue piece 722 and the clipping portions 310.

Figure 15A:
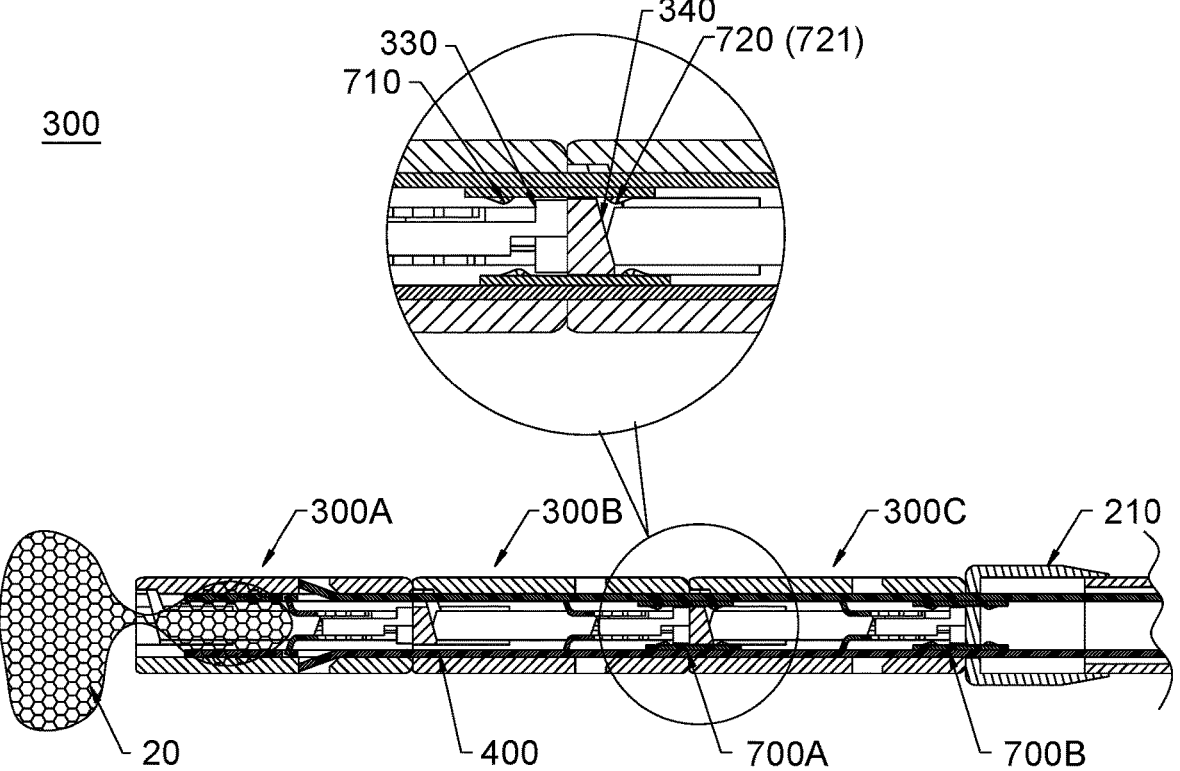
FIG. 15A-FIG. 15C are schematic diagrams illustrating a changing process of a connecting member when clipping portions are released according to some embodiments of the present disclosure.
Figure 15B:
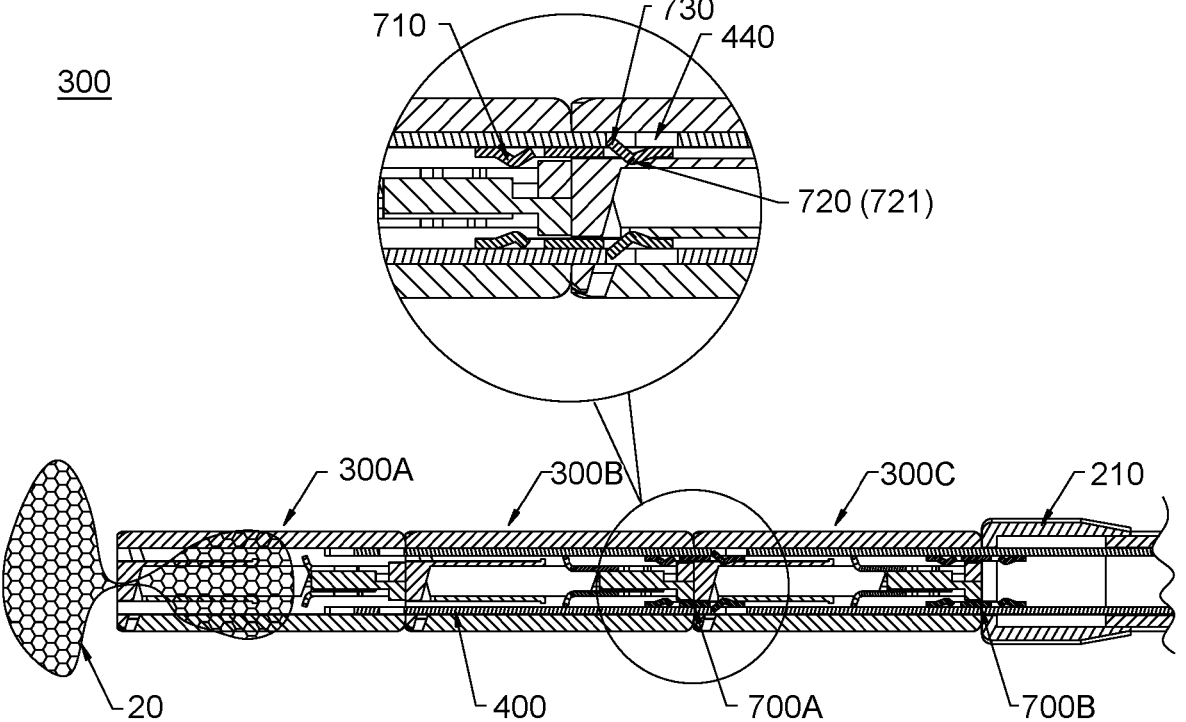
Figure 15C:
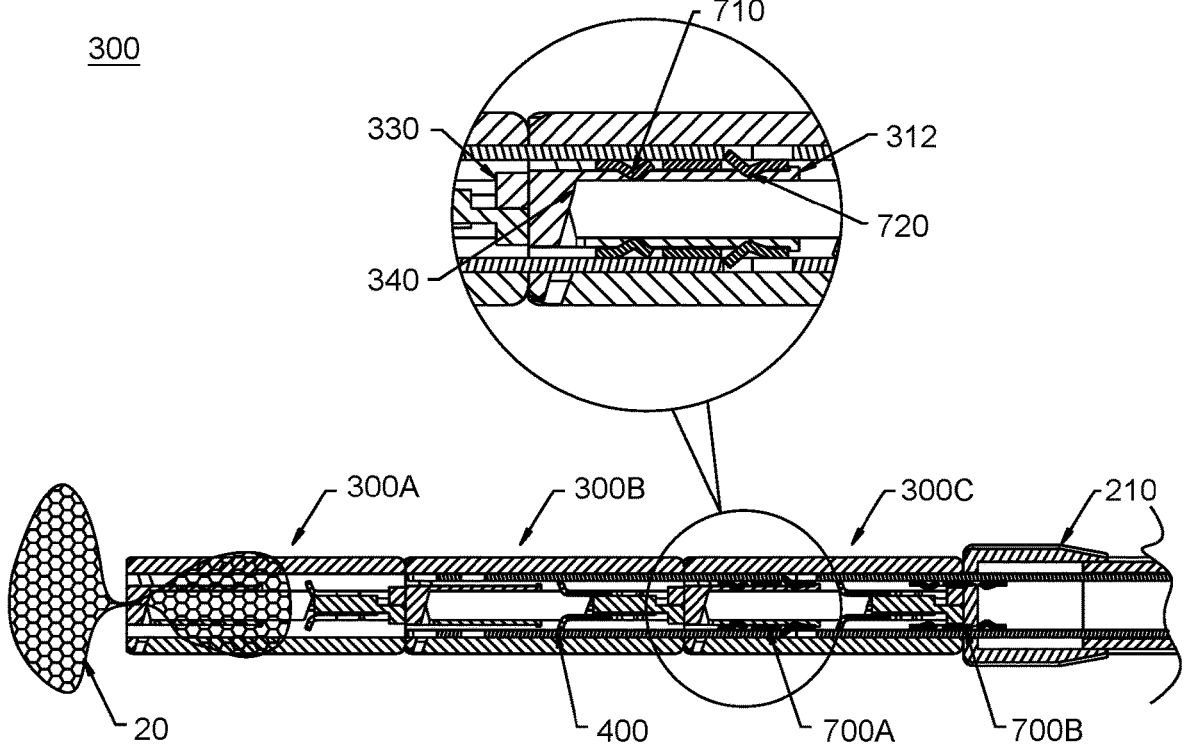

FIG. 15A-FIG. 15C are schematic diagrams illustrating a changing process of a connecting member when clipping portions are released according to some embodiments of the present disclosure. Taking the clip apparatus 10 including three clip devices 300 as an example, the three clip devices 300 respectively include the first clipping portion 310A, the second clipping portion 310B, and the third clipping portion 310C. The connecting member 700 may include the first connecting member 700A and the second connecting member 700B, the first connecting member 700A connects the second clipping portion 310B and the third clipping portion 310C, and the second connecting member 700B connects the third clipping portion 310C and the sheath pipe 210. A count of clip devices 300 in the embodiment is for illustrative purposes only and does not limit a count of clipping portions 310 in the embodiments of the present disclosure. For the clip apparatus 10 with a different count of clip devices 300, please refer to the clipping process shown in FIG. 15A-FIG. 15C.

As shown in FIG. 15A, in some embodiments, the first clipping portion 310A, the second clipping portion 310B, and the third clipping portion 310C are all in a closed and connected state. In some embodiments, the first connecting portion 710 of the first connecting member 700A may mate with the first mating portion 330 of the second clipping portion 310B, and the tab 721 of the first connecting member 700A is deformed squeezing, which achieves a release of the mating of the second connecting portion 720 and the second mating portion 340 of the third clipping portion 310C. The first connecting portion 710 of the second connecting member 700B may mate with the first mating portion 330 of the third clipping portion 310C, and the second connecting portion 720 of the second connecting member 700B is squeezed to be deformed and mates with the second mating portion 340 of the sheath pipe 210.

As shown in FIG. 15B, in some embodiments, the first clipping portion 310A, the second clipping portion 310B, and the third clipping portion 310C are all in a closed and connected state. The extension portion 400 is moved from a distal end to a proximal end and released from the first clipping portion 310A. When the third mating portion 440 of the extension portion 400 is moved to a position of the first connecting portion 710 of the first connecting member 700A, the third mating portion 440 of the extension portion 400 may cross over the first connecting portion 710 because the free end of the first connecting portion 710 is inclined from the distal end to the proximal end. When the third mating portion 440 of the extension portion 400 is moved to a position of the second connecting portion 720 of the first connecting member 700A, the tab 721 of the first connecting member 700A is released from being squeezed and returns to its original shape under the action of an elastic force, and the third connecting portion 730 formed by the free end of the tab 721 extends into the third mating portion 440 of the extension portion 400 to form a mating.

As shown in FIG. 15 C, in some embodiments, the first clipping portion 310A is in a closed state, and the second clipping portion 310B and the third clipping portion 310C are in a closed state. The extension portion 400 is moved from the distal end to the proximal end so that the first connecting portion 710 of the first connecting member 700A crosses over the first mating portion 330 of the second clipping portion 310B, the second connecting portion of the first connecting member 700A separates from the second mating portion 340 of the third clipping portion 310C, thereby driving the first connecting member 700A to move into the third clipping portion 310C, so that a release of the connection between the second clipping portion 310B and the third clipping portion 310C is achieved. The extension portion 400 is moved from the distal end to the proximal end, and a proximal end of the first connecting member 700A abuts against the resisting portion 312 of the third clipping portion 310C. When the extension portion 400 continues to move from the distal end to the proximal end, the third connecting portion 730 of the first connecting member 700A is deformed or displaced and disengages from the third mating portion 440 of the extension portion 400, and the first connecting member 700A stays in the third clipping portion 310C.

The extension portion 400 continues to move from the distal end to the proximal end to control the second connecting member 700B to release the third clipping portion 310C from the sheath pipe 210 in a similar manner to the above-described releasing process, which may not be repeated in the present disclosure.

The clip apparatus 10 in example three may be described in detail in conjunction with FIG. 16-FIG. 25J hereinafter. In the following, differences between the clip apparatus 10 in example three and the clip apparatus 10 in example one in the present disclosure may be described, and the same portions may be referred to in the description of example one, which may not be repeated in the present disclosure.

Figure 16:
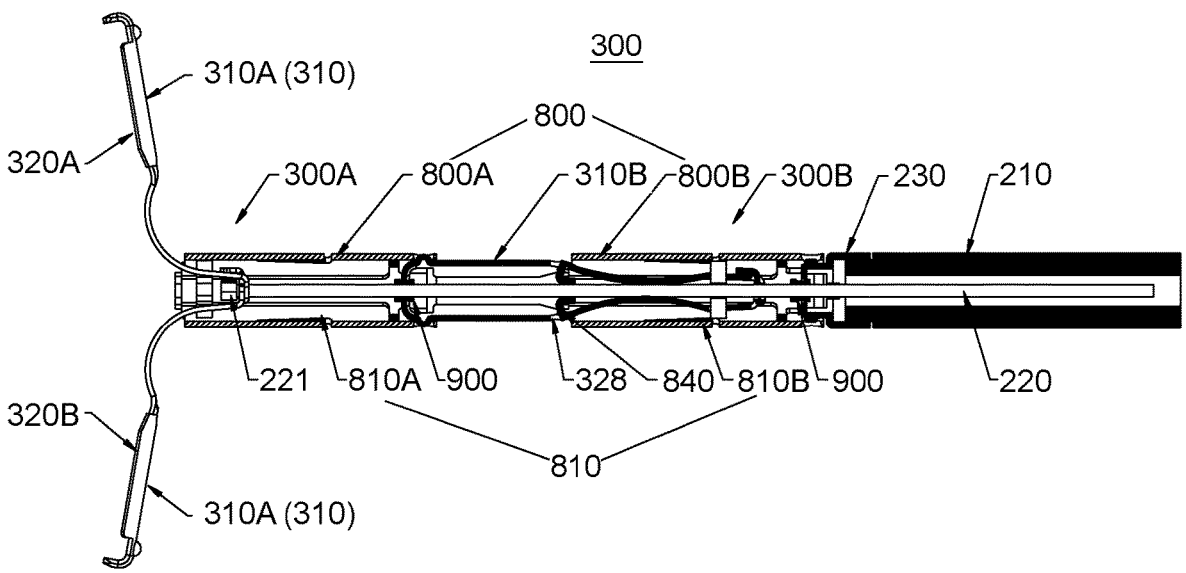
FIG. 16 is a diagram illustrating a cross section of an assembly of a clip device according to some embodiments of the present disclosure.

FIG. 16 is a diagram illustrating a cross section of an assembly of a clip device according to some embodiments of the present disclosure.

As shown in FIG. 16, in some embodiments, the clip apparatus 10 may include at least two clip devices 300, each of which may include a storage pipe 800 and the clipping portions 310. Exemplarily, the first clip device 300A may include a first storage pipe 800A and the first clipping portion 310A, and the second clip device 300B may include a second storage pipe 800B and the second clipping portion 310B. In some embodiments, the proximal end of the first clipping portion 310A is stored in the first storage pipe 800A, and the proximal end of the second clipping portion 310B is stored in the second storage pipe 800B. When the first clip device 300A and the second clip device 300B are connected, at least a portion of the second clipping portion 310B may mate with the first storage pipe 800A within the first storage pipe 800A. By providing the storage pipe 800, the closure stability of the clipping portion 310 may be improved.

In some embodiments, the storage pipe 800 may include a passage 810 that accommodates the clipping portion 310. The first storage pipe 800A may include a first passage 810A, and a proximal end of the first clipping portion 310A may be stored within the first passage 810A. The second storage pipe 800B may include a second passage 810B, and a proximal end of the second clipping portion 310B may be stored within the second passage 810B. Storing the clipping portion 310 through the passage 810 of the storage pipe 800 keeps the clipping portion 310 in a closed state to achieve locking of the clipping portion 310.

In some embodiments, a total length of at least two clip devices 300 when connected to each other is less than a sum of a length of each of the at least two clip devices 300. The clip device 300 may include the clipping portions 310 and the storage pipe 800. The length of each of the clip devices 300 may include a distance from a distal end of each of the clipping portions 310 to a proximal end of the storage pipe 800. When the clip devices 300 are connected to each other, at least a portion of the distal end of the clipping portions 310 extends into the storage pipe 800, the total length of the clip devices 300 when connected to each other may include a distance from the distal end of the clipping portions 310 at a most distal end to the proximal end of the storage pipe 800 at a most proximal end. Since at least a portion of the clipping portions 310 of a latter of the interconnected clip devices 300 is stored within the storage pipe 800 of a former of the clip devices 300, it is known that the total length of the clip devices 300 when connected to each other is less than the sum of the length of each of the clip devices 300.

In some embodiments, at least one of storage pipes 800 is releasably connected to the clipping portion 310 or sheath pipe 210. In some embodiments, a proximal end of the first storage pipe 800A is releasably connected to the distal end of the second clipping portion 310B, and the proximal end of the second storage pipe 800B is releasably connected to the distal end of the sheath pipe 210.

Figure 17:
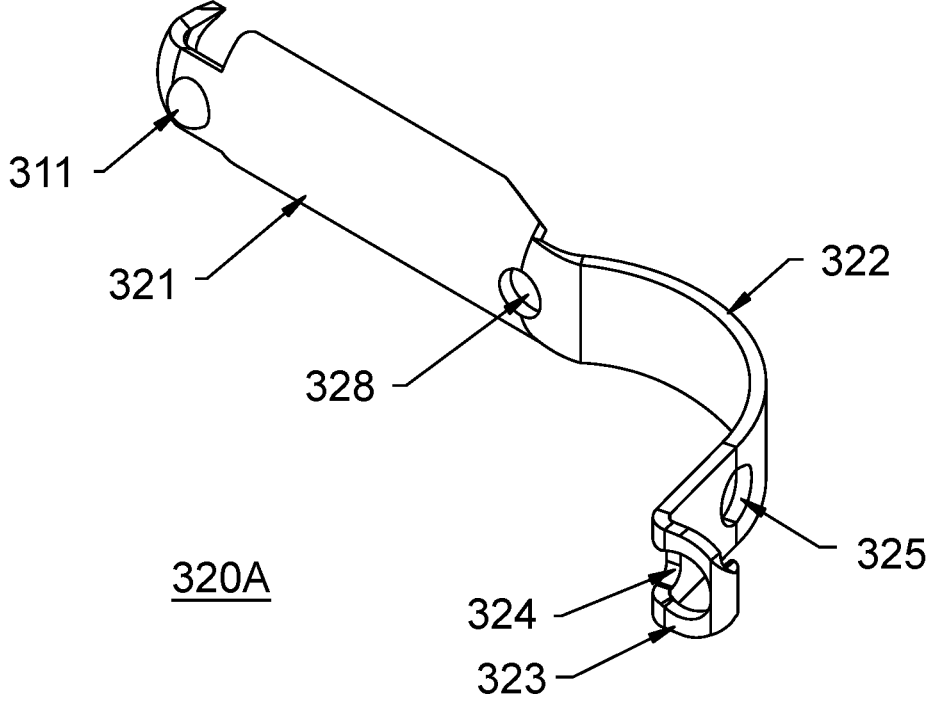
FIG. 17 is an exemplary diagram illustrating a structure of a first clipping arm according to some embodiments of the present disclosure.
Figure 18:
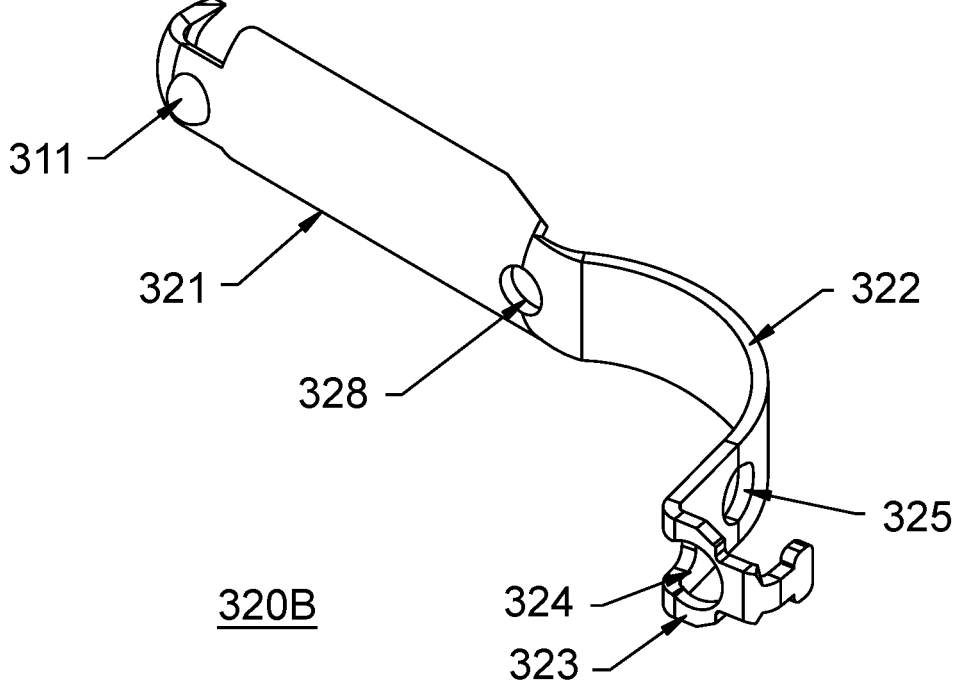
FIG. 18 is an exemplary diagram illustrating a structure of a second clipping arm according to some embodiments of the present disclosure.
Figure 19:
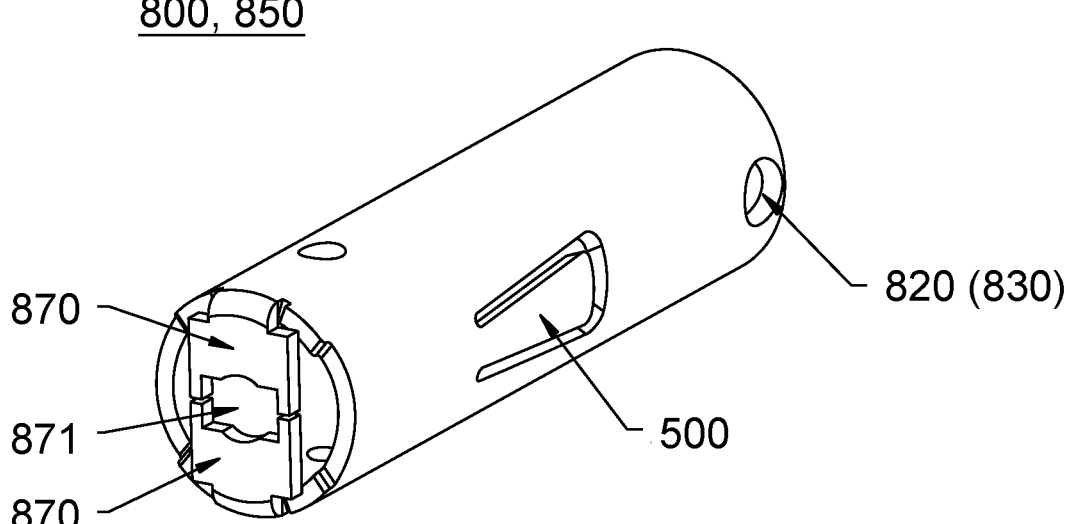
FIG. 19 is an exemplary diagram illustrating a structure of a storage pipe according to some embodiments of the present disclosure.

FIG. 17 is an exemplary diagram illustrating a structure of a first clipping arm according to some embodiments of the present disclosure. FIG. 18 is an exemplary diagram illustrating a structure of a second clipping arm according to some embodiments of the present disclosure. FIG. 19 is an exemplary diagram illustrating a structure of a storage pipe according to some embodiments of the present disclosure.

As shown in FIGS. 16-19, in some embodiments, each of the clipping portions 310 may include the first clipping arm 320A and the second clipping arm 320B. The first clipping arm 320A and the second clipping arm 320B include a clipping claw 321 provided on a distal end and a curved arm 322 provided on a proximal end, respectively, and the clipping claw 321 is configured to clip the tissue. In some embodiments, the curved arm 322 is flexible. At least a portion of the curved arm 322 is curved when located outside of the storage pipe 800, which may provide a greater span for the clipping claw 321. The at least a portion of the curved arm 322 deforms and is stored in the storage pipe 800 when located inside the storage pipe 800, keeping the first clipping arm 320A and the second clipping arm 320B closed. The clip device 300 is in an opening state when the clipping claw 321 of the first clipping arm 320A and the clipping claw 321 of the second clipping arm 320B are away from each other, and the clipping claw 321 of the first clipping arm 320A and the clipping claw 321 of the second clipping arm 320B are in a closed state when the clipping claw 321 of the first clipping arm 320A and the clipping claw 321 of the second clipping arm 320B are close to each other.

In some embodiments, the distal end of the at least one clipping portion 310 is provided with a first outer connecting portion 311, and the proximal end of the at least one storage pipe 800 is provided with a first outer connecting hole 820, the first outer connecting portion 311 may mate with the first outer connecting hole 820, making the clipping portions 310 connected to the storage pipe 800. In some embodiments, when the first outer connecting portion 311 may mate with the first outer connecting hole 820, the first clip device 300A may be connected to the second clip device 300B. A release of the mating of the first outer connecting portion 311 and the first outer connecting hole 820 achieves a release of the connection between the first clip device 300A and the second clip device 300B. For example, the second clipping portion 310B is provided with a first outer connecting portion 311, the first storage pipe 800A is provided with a first outer connecting hole 820, and the first outer connecting portion 311 releasably may mate with the first outer connecting hole 820.

As shown in FIGS. 17-19, in some embodiments, a distal end of the first clipping arm 320A and a distal end of the second clipping arm 320B are respectively provided with a convex portion, the convex portion forms a first outer connecting portion 311, the proximal end of the first storage pipe 800A is provided with a first outer connecting hole 820, and the convex portion releasably may mate with the first outer connecting hole 820.

Figure 20:
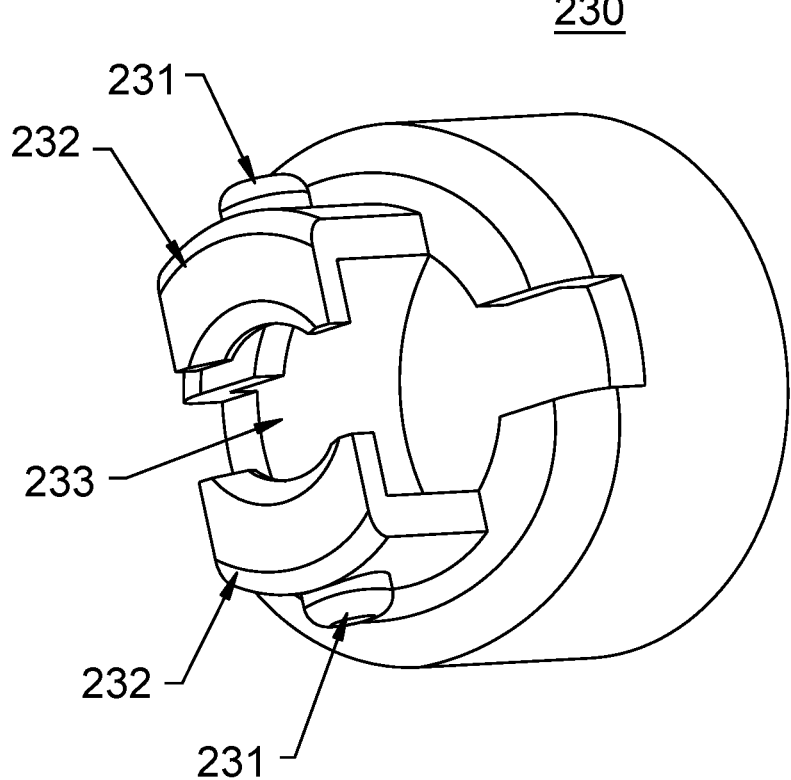
FIG. 20 is an exemplary diagram illustrating a structure of a bushing according to some embodiments of the present disclosure.

FIG. 20 is an exemplary diagram illustrating a structure of a bushing according to some embodiments of the present disclosure.

As shown in FIG. 16 and FIG. 20, in some embodiments, the conveying device 200 further may include a bushing 230, the proximal end of the bushing 230 is removably connected to the distal end of the sheath pipe 210, the bushing 230 is provided with a second outer connecting portion 231, the second storage pipe 800B is provided with a second outer connecting hole 830, the second outer connecting portion 231 releasably cooperates with the second outer connecting hole 830. In some embodiments, the second clip device 300B is connected to the sheath pipe 210 when the second outer connecting portion 231 may mate with the second outer connecting hole 830. A release of the connection between the second clip device 300B and the sheath pipe 210 is achieved when a release of the mating of the second outer connecting portion 231 and the second outer connecting hole 830 is achieved.

As shown in FIG. 19 and FIG. 20, in some embodiments, two elastic arms 232 are provided on the distal end of the bushing 230, with a bonding hole 233 formed between the two elastic arms 232 to allow the core shaft 220 to pass through, and the elastic arms 232 are provided with second outer connecting portion 231 formed by convex portions.

Figure 21:
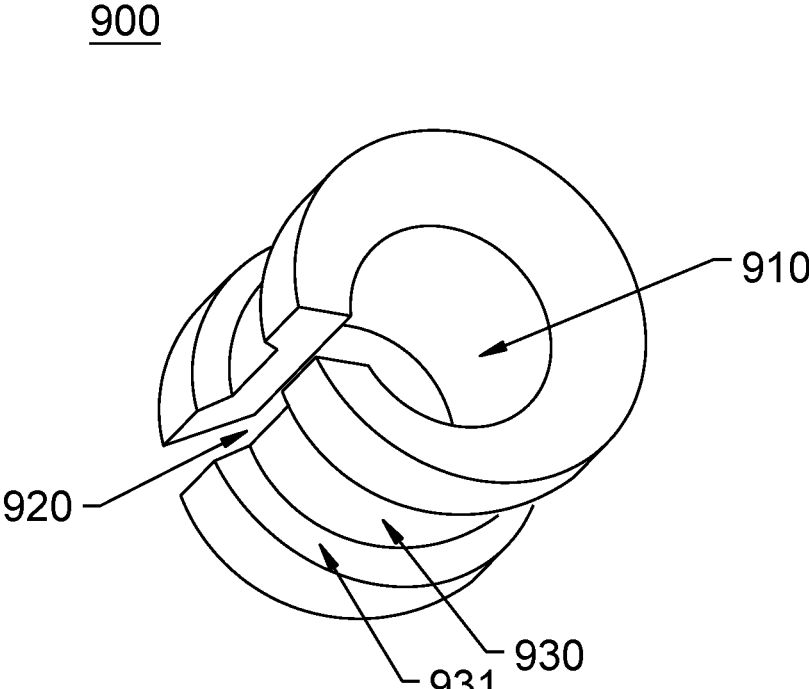
FIG. 21 is an exemplary diagram illustrating a structure of a spacer portion according to some embodiments of the present disclosure.

FIG. 21 is an exemplary diagram illustrating a structure of a spacer portion according to some embodiments of the present disclosure.

As shown in FIG. 16 and FIG. 21, in some embodiments, the core shaft 220 may include a spacer portion 900, the spacer portion 900 is configured to increase a radial distance of a distal end of the clipping portion 310, and/or, the spacer portion 900 is configured to increase a radial distance of a distal end of the bushing 230 of the sheath pipe 210. In some embodiments, there are a plurality of spacer portions 900, the plurality of spacer portions 900 are socketed to the core shaft 220 and may slide axially relative to the core shaft 220.

In some embodiments, the spacer portion 900 is releasably provided on the distal end of the second clipping portion 310B, which may spread the first outer connecting portion 311 in a radial direction. A distal end of the second clipping portion 310B may be stored in the first passage 810A, and when the spacer portion 900 is combined with the distal end of the second clipping portion 310B, the first outer connecting portion 311 provided on the second clipping portion 310B is radially moved outward to be combined with the first outer connecting hole 820 of the first storage pipe 800A, and the second clipping portion 310B is connected to the first storage pipe 800A. When the spacer portion 900 is not connected to the second clipping portion 310B, the first outer connecting portion 311 of the second clipping portion 310B is moved radially inward until the first outer connecting portion 311 is not connected to the first outer connecting hole 820 of the first storage pipe 800A, for example, the first outer connecting portion 311 is separated from the first outer connecting hole 820 of the first storage pipe 800A, and a release of the connection between the second clipping portion 310B and the first storage pipe 800A is achieved.

In some embodiments, the spacer portion 900 is releasably provided on a distal end of the sheath pipe 210, which may spread the second outer connecting portion 231 in the radial direction. The spacer portion 900 combines with two elastic arms 232 of the bushing 230, the elastic arms 232 undergoes resilient outward expansion, the second outer connecting portion 231 provided in the bushing 230 is moved radially outward to combine with the second outer connecting hole 830 of the second storage pipe 800B, and the sheath pipe 210 is connected to the second storage pipe 800B. The spacer portion 900 is not connected to the bushing 230 of the sheath pipe 210, the second outer connecting portion 231 provided on the bushing 230 is moved radially inward, the second outer connecting portion 231 is not connected to the second outer connecting hole 830 of the second storage pipe 800B, and a release of the connection the sheath pipe 210 and the second storage pipe 800B is achieved.

In some embodiments, the spacer portion 900 may include a spacer hole 910, and the core shaft 220 penetrates the spacer hole 910. A connecting head 221 is provided on a distal end of the core shaft 220, and a radial dimension of the connecting head 221 is larger than a radial dimension of the spacer hole 910. The connecting head 221 continues to move from a distal end to a proximal end after abutting against the spacer portion 900, so that the connecting head 221 drives the spacer portion 900 to move from a distal end to a proximal end. When the spacer portion 900 is not connected to the second clipping portion 310B, the distal end of the second clipping portion 310B is moved radially inward, and the first outer connecting portion 311 is not connected to the first outer connecting hole 820, and a release of the connection between the second clipping portion 310B and the first storage pipe 800A is achieved.

In some embodiments, the core shaft 220 is withdrawn from the bonding hole 233 by moving from a distal end to a proximal end, and after the connecting head 221 abuts against the spacer portion 900, the connecting head 221 continues to move from the distal end to the proximal end such that the connecting head 221 drives the spacer portion 900 to move from a distal end to a proximal end. The spacer portion 900 is withdrawn from an accommodating space between the elastic arms 232 of the bushing 230, the elastic arms 232 are resiliently contracted, a size of the bonding hole 233 decreases so that the second outer connecting portion 231 is moved radially inward, the second outer connecting portion 231 is not connected to the second outer connecting hole 830 of the second storage pipe 800B, and a release of the connection between the second storage pipe 800B and the bushing 230 of the sheath pipe 210 is achieved.

In some embodiments, the spacer portion 900 may include a fracture 920, the fracture 920 extends in an axial direction of the spacer portion. The spacer portion 900 is subjected to a force of the connecting head 221 abutting against the spacer portion 900, and the spacer portion 900 is more likely to deform radially outward due to the spacer portion 900 being provided with the fracture 920, and the spacer portion 900 is separated from the connecting head 221.

In some embodiments, the spacer portion 900 may include a mating slot 930, the mating slot 930 is formed on an outer surface of the spacer portion 900 and extends as an annular slot in a circumferential direction of the spacer portion 900. The mating slot 930 is configured to accommodate the distal end of the clipping portion 310, and/or the distal ends of the two elastic arms 232 of the bushing 230 of the sheath pipe 210, such that the clipping portion 310 and/or the elastic arms 232 are releasably axially limited with the spacer portion 900. In some embodiments, the mating slot 930 may include a guiding bevel 931 inclined in a radial direction, and the guiding bevel 931 is located on both sidewalls of the mating slot 930. When the spacer portion 900 is moved in an axial direction, the guiding bevel 931 may guide the distal end of the clipping portion 310 and/or the elastic arm 232 out of the mating slot 930.

In some embodiments, the spacer portion 900 may be integrally molded with the connecting head 221. A diameter of the core shaft 220 is set such that the first outer connecting portion 311 is connected to the first outer connecting hole 820 and the second outer connecting portion 231 is connected to the second outer connecting hole 830. The spacer portion 900 may be a mating slot recessed inward on the connecting head 221, and a structure of the mating slot may be found in the structure of the mating slot 930 of the spacer portion 900 described above. When the connecting head 221 is moved to the distal end of the clipping portion 310, the distal end of the clipping portion 310 is moved radially inward and enters into the mating slot such that the first outer connecting portion 311 is not connected to the first outer connecting hole 820. When the connecting head 221 is moved to the distal end of the bushing 230, the distal end of the elastic arm 232 of the bushing 230 is moved radially inward and enters into the mating slot such that the second outer connecting portion 231 is not connected to the second outer connecting hole 830. In some embodiments, the connecting head 221 may be formed as a tapered structure with a small distal end and a large proximal end. When the connecting head 221 is moved from the distal end to the proximal end, the clipping portion 310 and/or the elastic arm 232 of the bushing 230 the distal end may move radially inward along the bevel of the tapered structure.

Figure 22:
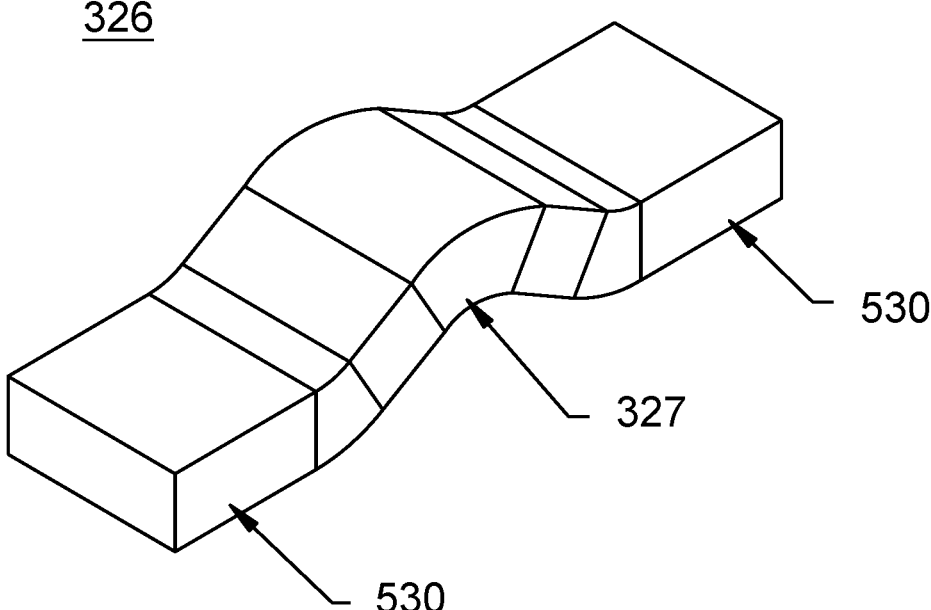
FIG. 22 is an exemplary diagram illustrating a structure of a pin roll according to some embodiments of the present disclosure.

FIG. 22 is an exemplary diagram illustrating a structure of a pin roll according to some embodiments of the present disclosure.

As shown in FIGS. 16-18, and FIG. 22, in some embodiments, a proximal end of the first clipping arm 320A is provided with an inner connecting hole 324, and a proximal end of the second clipping arm 320B is also provided with the inner connecting hole 324. A distal end of the core shaft 220 is provided with a connecting head 221, and the connecting head 221 is provided with a large diameter portion and a small diameter portion from a distal end to a proximal end. The large diameter portion passes through the inner connecting hole 324 of the first clipping arm 320A and the inner connecting hole 324 of the second clipping arm 320B, respectively, and the small diameter portion is snapped into the inner connecting hole 324 of the first clipping arm 320A and the inner connecting hole 324 of the second clipping arm 320B. The connecting head 221 is subjected to a force from a distal end to a proximal end, making a proximal end of the first clipping arm 320A and a proximal end of the second clipping arm 320B deformed or displaced, and the connecting head 221 is withdrawn from the inner connecting hole 324, and the core shaft 220 is separated from the first clipping portion 310A or the second clipping portion 310B.

In some embodiments, the proximal end of the first clipping arm 320A is provided with a bending portion 323, the proximal end of the second clipping arm 320B is also provided with the bending portion 323, and the inner connecting hole 324 is provided on the bending portion 323.

In some embodiments, a first hole 325 is provided on the proximal end of the first clipping arm 320A, and the first hole 325 is also provided on the proximal end of the second clipping arm 320B. In some embodiments, the clipping portion 310 may further include a pin roll 326, the pin roll 326 passes through the first hole 325 of the first clipping arm 320A and the first hole 325 of the second clipping arm 320B, respectively, to achieve a connection between the inner connecting hole 324 of the first clipping arm 320A and the inner connecting hole 324 of the second clipping arm 320B, so that the first clipping arm 320A is fixed to the proximal end of the second clipping arm 320B.

In some embodiments, an arching portion 327 is provided on a middle end of the pin roll 326, and the arching portion 327 constitutes a penetration space that may be utilized for axial movement of the core shaft 220 over the pin roll 326, such that the core shaft 220 fixes the two clipping arms 320 without impeding the axial movement of the core shaft 220 between the two clipping arms 320.

Figure 23:
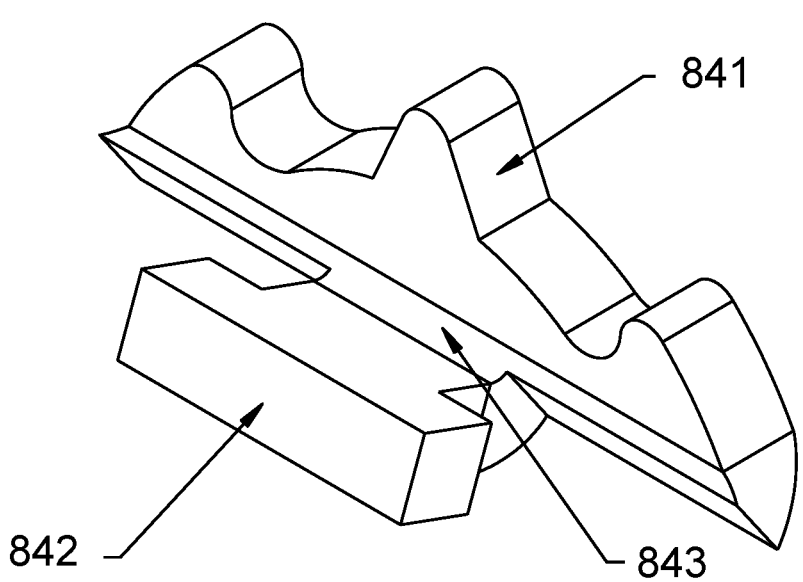
FIG. 23 is an exemplary diagram illustrating a structure of a limit portion according to some embodiments of the present disclosure.

FIG. 23 is an exemplary diagram illustrating a structure of a limit portion according to some embodiments of the present disclosure.

As shown in FIG. 16, FIG. 19, FIG. 20, and FIG. 23, in some embodiments, at least one of the clipping portions 310 may include a fixing hole 328 (or referred to as a second hole), the fixing hole 328 is provided on the first clipping arm 320A and the second clipping arm 320B, respectively. For example, the fixing hole 328 is provided in a junction between the clipping claws 321 and the curved arm 322. The storage pipe 800 may include a limit portion 840, and the limit portion 840 is releasably connected to the fixing hole 328. In some embodiments, the clipping portion 310 is fixed relative to the storage pipe 800 when the limit portion 840 is connected to the fixing hole 328. In some embodiments, when the limit portion 840 is not connected to the fixing hole 328, the clipping portion 310 may move relative to the storage pipe 800.

In some embodiments, a limit portion 840 is radially movable at the distal end of the storage pipe 800, and the limit portion 840 may include a fixing end 842 and a fixing claw 841. The fixing claw 841 moves radially outward and bonds within the fixing hole 328 when the fixing end 842 contacts with the core shaft 220. The fixing claw 841 moves radially inward and withdraws the fixing hole 328 when the fixing end 842 does not in contact with the core shaft 220.

In some embodiments, the fixing claw 841 may snap the fixing hole 328, and the fixing end 842 is provided in the storage pipe 800. The limit portion 840 further may include a sliding slot 843 provided between the fixing end 842 and the fixing claw 841, a distal end of the storage pipe 800 is provided with a blocking portion 870, and the limit portion 840 is connected to the second storage pipe 800B. The distal end of the second storage pipe 800B is provided with a blocking portion 870, the sliding slot 843 is snapped to the blocking portion 870, and the fixing end 842 is stored in the second passage 810B. The blocking portion 870 is also provided with a penetrating hole 871, and the core shaft 220 may move radially axially in the penetrating hole 871. The fixing claw 841 is bonded within the fixing hole 328, and the second clipping portion 310B is fixed relative to the second storage pipe 800B. The fixing claw 841 is not bonded within the fixing hole 328, and the second clipping portion 310B may be moved relative to the second storage pipe 800B.

As shown in FIG. 19 and FIG. 22, in some embodiments, a wall of the storage pipe 800 is provided with a slug, respectively, the slug being radially deflected inward, and the slug forms the locking portion 500. The first clipping portion 310A and the second clipping portion 310B both include a first clipping arm 320A, a second clipping arm 320B, and the pin roll 326 fixedly connecting the first clipping arm 320A to the second clipping arm 320B. Both ends of the pin roll 326 form a locked portion 530. The pin roll 326 moves from a distal end to a proximal end to cross over the slug, the locking portion 500 bonds with the locked portion 530, and the slug limits the movement of the clip device 300 from a proximal end to a distal end, i.e., the first clipping arm 320A and second clipping arm 320B remain closed.

Figure 24:
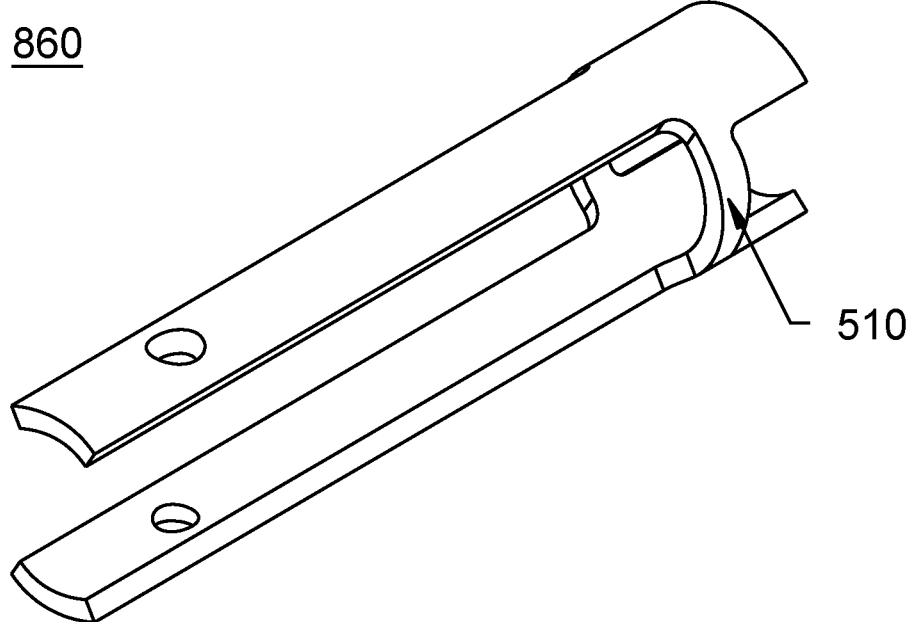
FIG. 24 is an exemplary diagram illustrating a structure of an inner pipe according to some embodiments of the present disclosure.

FIG. 24 is an exemplary diagram illustrating a structure of an inner pipe according to some embodiments of the present disclosure.

As shown in FIG. 19 and FIG. 24, in some embodiments, the first storage pipe 800A and the second storage pipe 800B are both of split-molded structure, and the split-molding processing process is simple, and the cost is lower. In some embodiments, the first storage pipe 800A and the second storage pipe 800B include an external pipe 850 and an internal pipe 860, respectively, and the internal pipe 860 is socketed within the passage 810 of the external pipe 850, and the passage 810 of the first storage pipe 800A and second storage pipe 800B is shared by the external pipe 850 and internal pipe 860. In some embodiments, the wall of the internal pipe 860 forms a locking stopper 540, the locking stopper 540 may limit the pin roll 326 to continually move from the distal end to the proximal end.

In some embodiments, the first storage pipe 800A and the second storage pipe 800B are integrally molded, and the locking stopper 540 is provided directly within the wall of the first storage pipe 800A and the wall of the second storage pipe 800B. The integral molding reduces accessories and makes assembly easier. Whether the storage pipe 800 is molded separately or molded integrally, the locking stopper 540 is provided in conjunction with the ends of the pin roll 326, thereby limiting the movement of the clip device 300 from a distal end to a proximal end.

FIG. 25A-FIG. 25J are schematic diagrams illustrating a clipping and releasing process of a clipping portion according to some embodiments of the present disclosure. Taking the clip apparatus 10 including two clip devices 300 as an example, the two clip devices 300 respectively include the first clipping portion 310A and the second clipping portion 310B. A count of clip devices 300 in the embodiment is for illustrative purposes only and does not limit a count of clipping portions 310 in the embodiments of the present disclosure. For the clip apparatus 10 with a different count of clip devices 300, please refer to the clipping process shown in FIG. 25A-FIG. 25J.

Figure 25A:
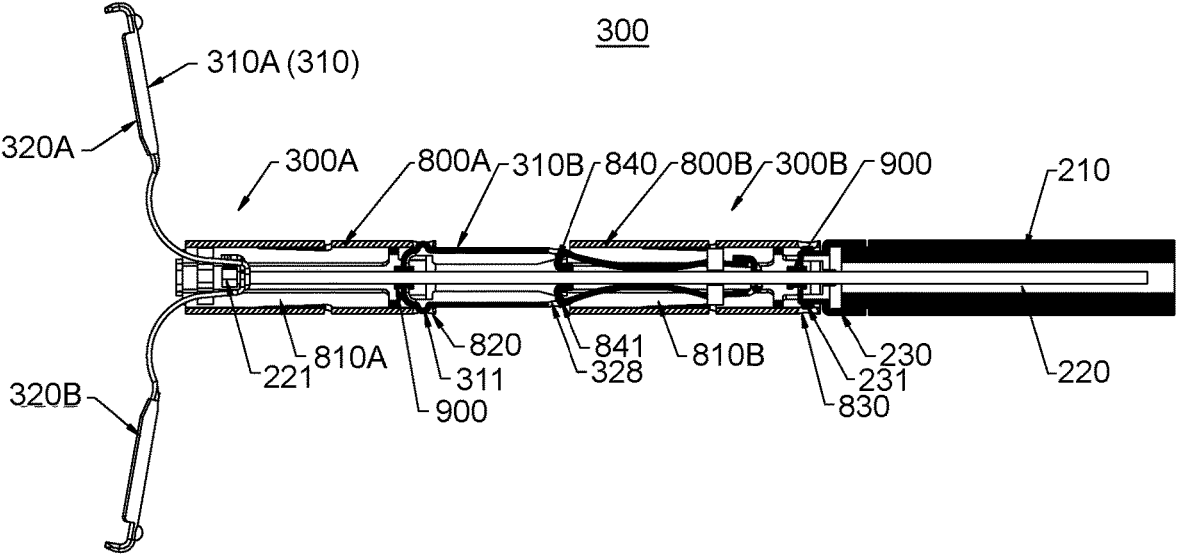
FIG. 25A-FIG. 25J are schematic diagrams illustrating a clipping and releasing process of clipping portions according to some embodiments of the present disclosure.

As shown in FIG. 25A, the clip device 300 is in a first state where the clip device 300 enters into a passage of the endoscopic, and the first clip device 300A provided on a most distal end moves close to the tissue (not shown in the figure). The first clip device 300A and the second clip device 300B are provided from a distal end to a proximal end outside the second storage pipe 800B of the sheath pipe 210 of the conveying device 200. The first clip device 300A may include a first clipping portion 310A and the first storage pipe 800A, the second clip device 300B may include a second clipping portion 310B and a second storage pipe 800B, the first storage pipe 800A is provided with the first passage 810A, the second storage pipe 800B is provided with the second passage 810B, and a proximal end of the first clipping portion 310A is stored in the first passage 810A. A proximal end of the second clipping portion 310B is stored in the second passage 810B, a distal end of the clipping arm 320 of the second clipping portion 310B is provided with a convex portion (the first outer connecting portion 311), and a spacer portion 900 running through the outside of the core shaft 220 is combined with the second clipping portion 310B so that the convex portion (the first outer connecting portion 311) moves radially outward and extends into the first outer connecting hole 820 of the first storage pipe 800A, thereby realizing the connection between the first clip device 300A and the second clip device 300B. The fixing claw 841 of the limit portion 840, which mutually abuts against the core shaft 220, extends into the fixing hole 328 provided in the second clipping portion 310B, to make the second clip device 300B move with the axial movement of the core shaft 220. Another spacer portion 900 running through the outside of the core shaft 220 is combined with the bushing 230 so that the convex portion (the second outer connecting portion 231) moves radially outward and extends into the second outer connecting hole 830 provided in the second storage pipe 800B, so as to realize the connection between the second clip device 300B and the sheath pipe 210. The core shaft 220 moves from the distal end to the proximal end, the first clipping portion 310A of the first clip device 300A provided on the most distal end is in an opening state, i.e., the first clipping arm 320A and the second clipping arm 320B are distal to each other for receiving the tissue. At the same time, the connecting head 221 of the core shaft 220 connected to the first clip device 300A is of a non-circular cross-section, and the proximal end of the core shaft 220 is rotated to drive the first clipping arm 320A and the second clipping arm 320B of the first clipping portion 310A to rotate so that a suitable clipping angle may be adjusted.

Figure 25B:
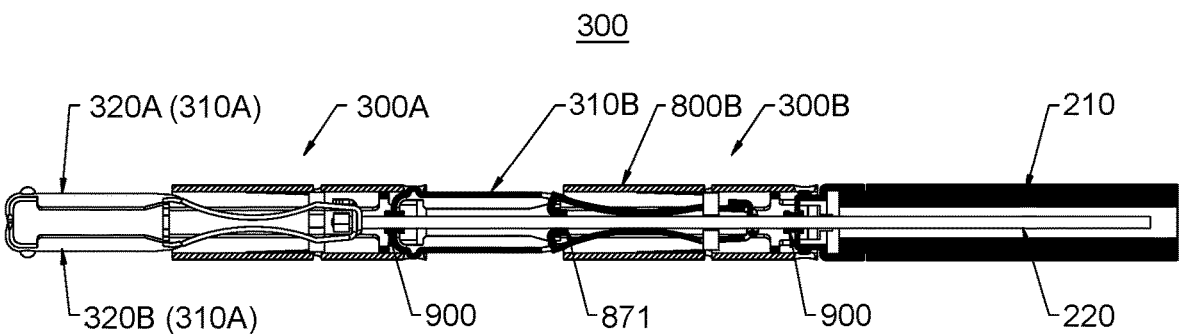

As shown in FIG. 25B, the clip device 300 is in a second state. The core shaft 220 is moved from a distal end to a proximal end, and the first clipping portion 310A provided on the most distal end is in a closed state, i.e., the first clipping arm 320A and the second clipping arm 320B move close to each other after receiving the tissue. The core shaft 220 respectively moves axially and freely in the spacer holes 910 of the plurality of spacer portions 900, and the core shaft 220 also moves axially and freely within the penetrating hole 871 of the blocking portion 870 provided on the second storage pipe 800B, and the first clip device 300A and the second clip device 300B remain connected, and the second clip device 300B and the sheath pipe 210 remain connected. When the first clipping portion 310A has an inappropriate clipping angle, the core shaft 220 moves from the proximal end to the distal end, and the clip device 300 is restored from the second state to the first state.

Figure 25C:
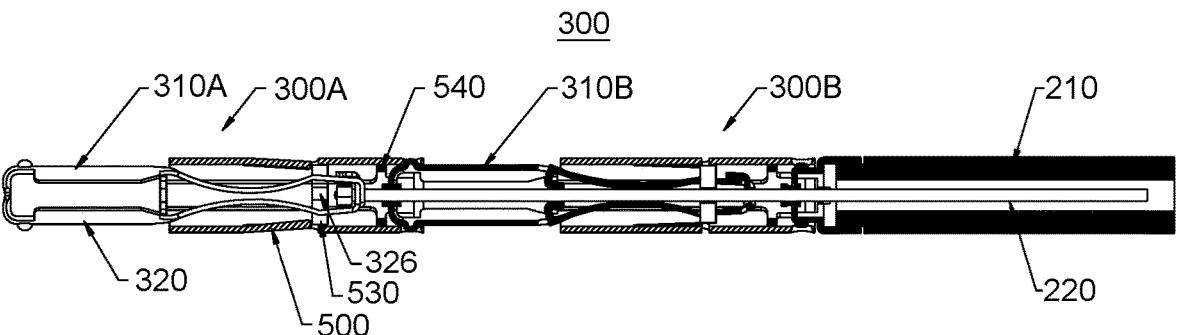

As shown in FIG. 25C, the clip device 300 is in a third state. The core shaft 220 continues to move from the distal end to the proximal end, and the ends of the pin roll 326 fixedly connecting the two clipping arms 320 of the first clipping portion 310A are crossed over the slug, i.e., the locked portion 530 provided in the pin roll 326 is combined with the locking portion 500 of the first storage pipe 800A, i.e., the slug is deflected radially inward when it returns to a free state to block the movement of the pin roll 326 from the proximal end to the distal end, i.e., the combination of the locked portion 530 and the locking portion 500 prevents the two clipping arms 320 of the first clipping portion 310A from being opened again. At the same time, as the locking stopper 540 resisting against the proximal end of the pin roll 326 is provided in the first passage 810A of the first storage pipe 800A, the locking stopper 540 restricts the pin roll 326 from continuing to move from the distal end to the proximal end, i.e., the first clipping portion 310A is locked by the first storage pipe 800A, and the two clipping arms 320 of the first clipping portion 310A are kept in the closed state.

Figure 25D:
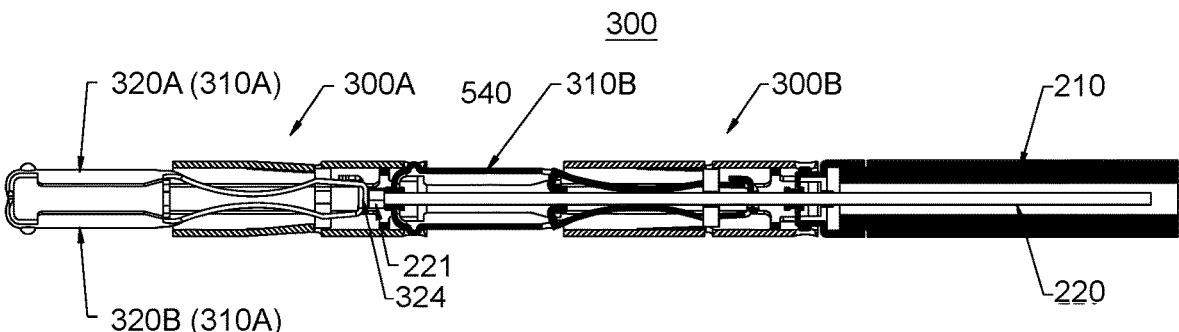

As shown in FIG. 25D, the clip device 300 is in a fourth state. The core shaft 220 continues to move from the distal end to the proximal end, and the connecting head 221 of the distal end of the core shaft 220 exerts a force toward the proximal end on the first clipping portion 310A, the force acts on the proximal end of the first clipping arm 320A and the proximal end of the second clipping arm 320B, causing the proximal end of the first clipping arm 320A and the proximal end of the second clipping arm 320B to be deformed or displaced, the connecting head 221 is withdrawn from the inner connecting hole 324, and the core shaft 220 separates from the first clipping portion 310A.

Figure 25E:
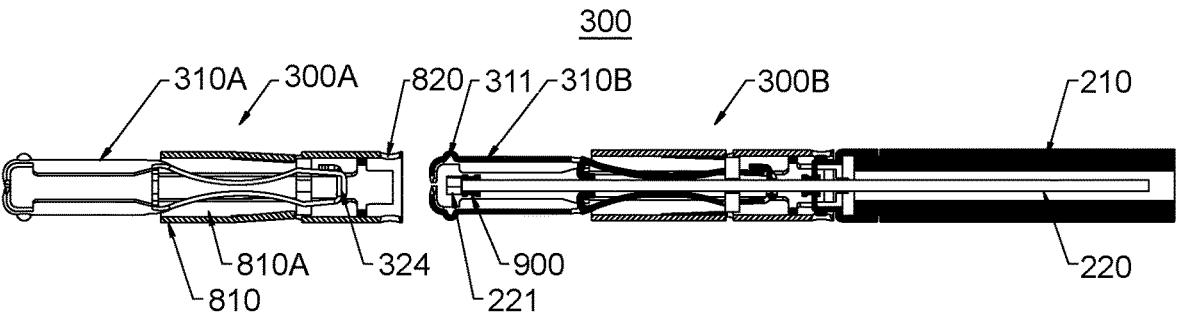

As shown in FIG. 25E, the clip device 300 is in a fifth state. After withdrawing from the inner connecting hole 324 of the first clip device 300A, the connecting head 221 continues to move from the distal end to the proximal end, a radial dimension of the connecting head 221 is larger than a radial dimension of the spacer portion 900, and the connecting head 221 continues to move from the distal end to the proximal end after abutting against the spacer portion 900, so that the connecting head 221 drives the spacer portion 900 to move from the distal end to the proximal end. The spacer portion 900 is not connected to the second clipping portion 310B, and the first outer connecting portion 311 of the second clip device 300B moves radially inward and is dislodged from the first outer connecting hole 820 of the first storage pipe 800A, and the second clipping portion 310B is withdrawn from the first passage 810A of the first storage pipe 800A, the first clip device 300A and the second clip device 300B are separated, and the first clip device 300A stays within the body with the tissue clipped.

Figure 25F:
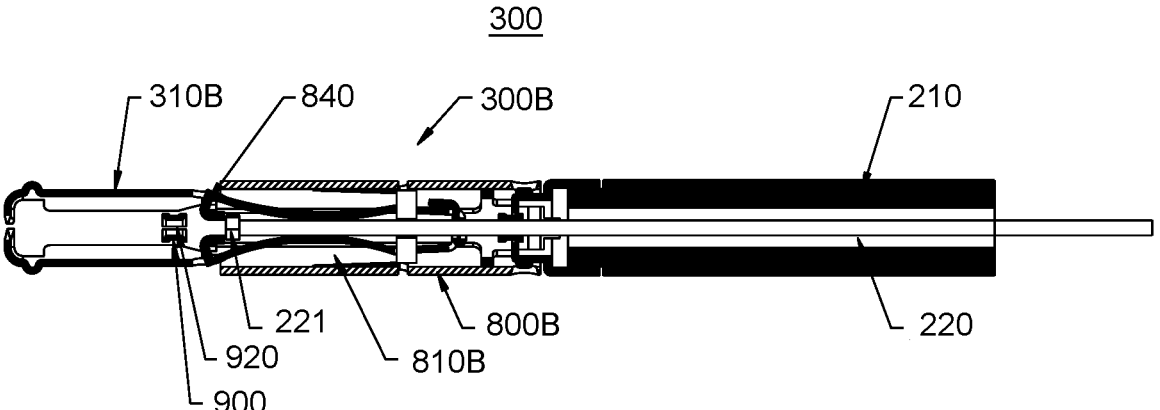

As shown in FIG. 25F, the clip device 300 is in a sixth state. The connecting head 221 continues to drive the spacer portion 900 to move from the distal end to the proximal end, and the spacer portion 900 abuts against the limit portion 840. The spacer portion 900 is subjected to a reaction force from a proximal end to a distal end of the limit portion 840. The spacer portion 900 located at the distal end is deformed and the connecting head 221 is withdrawn from the fracture 920 of the spacer portion 900. The connecting head 221 continues to move from the distal end to the proximal end and enters into the second passage 810B of the second storage pipe 800B, and spacer portion 900 located at the distal end stays outside the second passage 810B of the second storage pipe 800B.

Figure 25G:
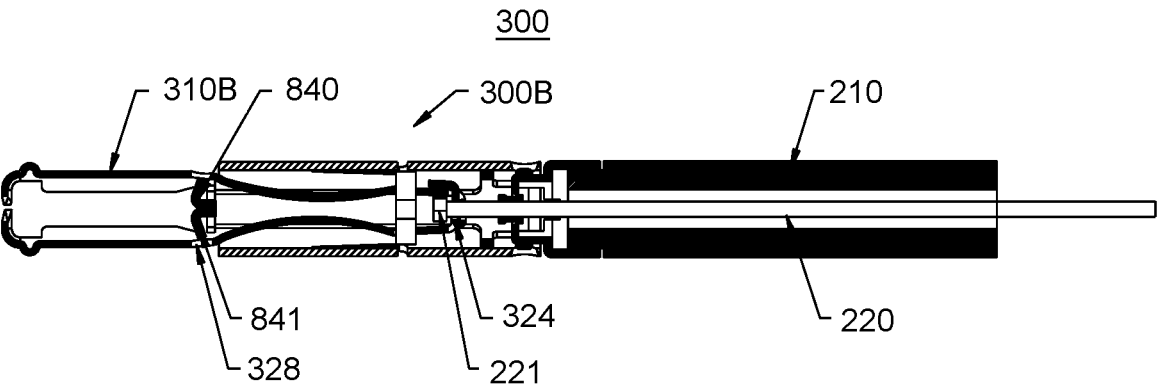

As shown in FIG. 25G, the clip device 300 is in the seventh state. The core shaft 220 continues to move from the distal end to the proximal end, and when the core shaft 220 is not connected to the limit portion 840, the fixing claw 841 of the limit portion 840 is moved radially inward and disengaged from the fixing hole 328 of the second clipping portion 310B, the second clipping portion 310B may move relative to the second storage pipe 800B. The connecting head 221 at the distal end of the core shaft 220 crosses the penetrating space of the pin roll 326 of the second clip device 300B until a small diameter portion of the connecting head 221 snaps within the inner connecting hole 324 of the second clipping portion 310B, thereby completing an inner connecting assembly of the second clip device 300B.

Figure 25H:
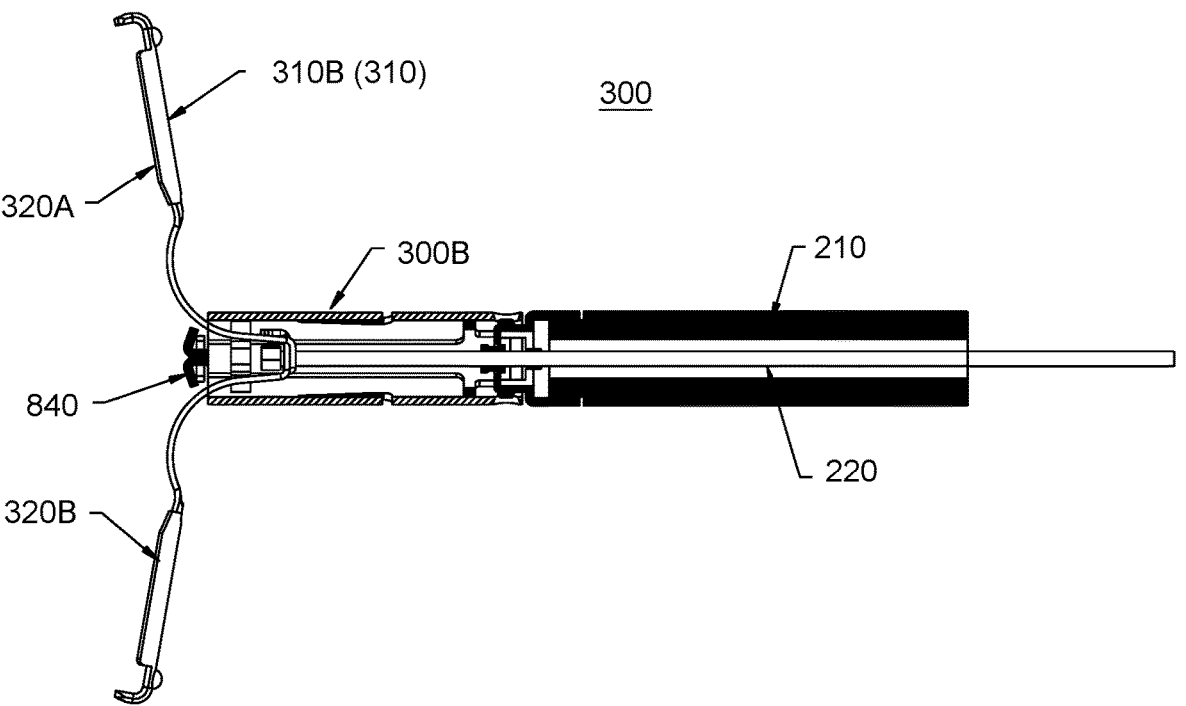
Figure 25I:
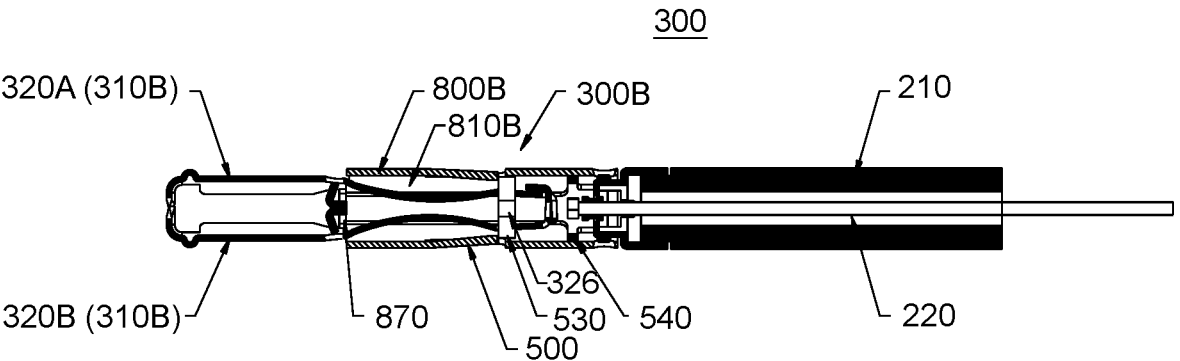
Figure 25J:
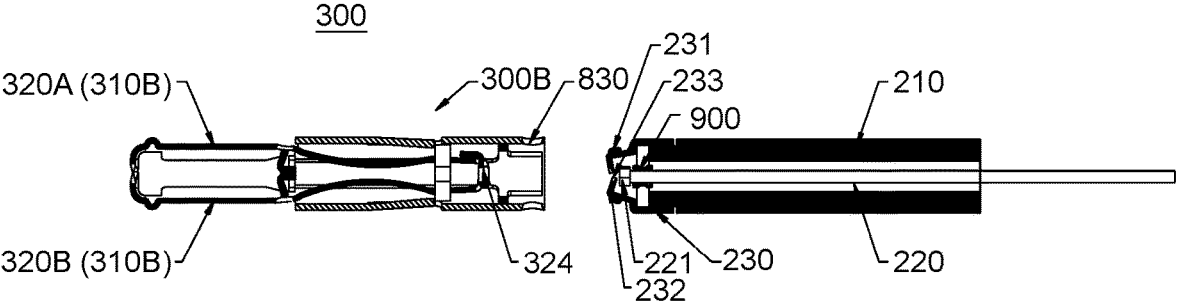

As shown in FIG. 25H, the clip device 300 is in an eighth state. After completion of the inner connection between the core shaft 220 and the second clip device 300B, the core shaft 220 is moved from the proximal end to the distal end, and the second clipping portion 310B is not constrained by the action of the limit portion 840, and the first clipping arm 320A and second clipping arm 320B of the second clipping portion 310B depart away from each other for receiving the tissue.

As shown in FIG. 25 I, the clip device 300 is in the ninth state. The core shaft 220 is moved from the distal end to the proximal end, and the second clipping portion 310B provided on the most distal end is in the closed state, i.e., the first clipping arm 320A and the second clipping arm 320B are close to each other after receiving the tissue. The core shaft 220 moves axially freely from the penetrating hole 871 of the blocking portion 870 provided on the second storage pipe 800B, and the second clip device 300B and the sheath pipe 210 remain connected. The core shaft 220 continues to move from the distal end to the proximal end, making two ends of the pin roll 326 that fixedly connects the first clipping arm 320A to the second clipping arm 320B of the second clipping portion 310B cross over the slug, i.e., the locked portion 530 provided on the pin roll 326 is combined with the locking portion 500 provided on the second storage pipe 800B, i.e., the slug is deflected radially inward when it is restored to the free state, which blocks the pin roll 326 from moving from the proximal end to the distal end, i.e., the combination of the locked portion 530 and the locking portion 500 prevents the first clipping arm 320A and the second clipping arm 320B of the second clipping portion 310B from being opened again. At the same time, since the second passage 810B of the second storage pipe 800B is provided with a locking stopper 540 that abuts against the proximal end of the pin roll 326, the locking stopper 540 restricts the pin roll 326 from continuing to move from the distal end to the proximal end, i.e., the second clipping portion 310B is locked by the second storage pipe 800B, and the first clipping arm 320A and the second clipping arm 320B of the second clipping portion 310B are maintained in the closed state.

As shown in FIG. 25 J, the clip device 300 is in a tenth state. The core shaft 220 continues to move from the distal end to the proximal end, and the force from the distal end to the proximal end subjected to the connecting head 221 of the distal end of the core shaft 220 acts on the proximal end of the first clipping arm 320A and the proximal end of said second clipping arm 320B such that the proximal end of the first clipping arm 320A and the proximal end of the second clipping arm 320B are deformed or displaced, the connecting head 221 is withdrawn from the inner connecting hole 324, and the core shaft 220 separates from the second clipping portion 310B. The core shaft 220 continues to move from the distal end to the proximal end, the connecting head 221 at the distal end of the core shaft 220 drives the spacer portion 900 to move from a distal end to a proximal end and to withdraw from the bonding hole 233 provided on the distal end of the bushing 230, the elastic arm 232 is not combined with the spacer portion 900, and the elastic arm 232 elastically recovers. The convex portion (the second outer connecting portion 231) provided on the elastic arm 232 moves radially inward, and the convex portion (the second outer connecting portion 231) is disengaged from the second outer connecting hole 830 of the second storage pipe 800B, i.e., the distal end of the bushing 230 is separated from the second passage 810B of the second storage pipe 800B, and a release of the connection between the second storage pipe 800B and the conveying device 200 is achieved. To this point, the at least two clip devices 300 provided outside the passage of the sheath pipe 210 sequentially complete the operation of clipping the tissue and stay in the body, and the conveying device 200 is withdrawn from the passage of the endoscopic.

The embodiments of the present disclosure include but are not limited to the following possible beneficial effects.

(1) According to the above-described scheme, the clip apparatus may be provided with different counts of clip devices, and the user may choose the clip apparatus provided with a suitable count of clip devices according to the size of the trauma of tissue to be stopped from bleeding as predicted in the surgery. The operation of clipping the tissue may be performed a plurality of times without repeated insertion, and clipping closure of large wounds or a plurality of bleeding points may be achieved in a shorter time, reducing surgical risks and costs.

(2) The total length of the at least two clip devices when connected to each other is less than the sum of the length of each of the at least two clip devices, making the total length of the at least two clip devices connected to each other outside the sheath pipe smaller and more maneuverable.

(3) By releasably connecting the clipping portion to the extension portion, the extension portion and conveying device that do not in contact with the tissue are withdrawn from the body, and a smaller-sized clipping portion stays in the body, which provides a larger operating space for subsequent surgical operations and reduces the impact on the human body.

(4) Connecting two clipping portions using the connecting member, and/or, connecting the clipping portion and the sheath pipe using the connecting member may improve the stability of the clipping portion, which avoids relative movement or relative rotation of the clipping portions.

(5) By providing the bonding member, the stability of the connection between the clipping portion and the extension portion may be improved.

(6) By providing the storage pipe, the stability of the closure of the clipping portion may be improved.

It should be noted that the beneficial effects that may be produced by different embodiments are different, and the beneficial effects that may be produced in different embodiments may be any one or a combination thereof, or any other beneficial effect that may be obtained.

Having thus described the basic concepts, it may be rather apparent to those skilled in the art after reading this detailed disclosure that the foregoing detailed disclosure is intended to be presented by way of example only and is not limiting. Although not explicitly stated here, those skilled in the art may make various modifications, improvements, and amendments to the present disclosure. These alterations, improvements, and amendments are intended to be suggested by this disclosure and are within the spirit and scope of the exemplary embodiments of the present disclosure.

Moreover, certain terminology has been used to describe embodiments of the present disclosure. For example, the terms "one embodiment," "an embodiment," and/or "some embodiments" mean that a particular feature, structure, or feature described in connection with the embodiment is included in at least one embodiment of the present disclosure. Therefore, it is emphasized and should be appreciated that two or more references to "an embodiment" or "one embodiment" or "an alternative embodiment" in various portions of the present disclosure are not necessarily all referring to the same embodiment. In addition, some features, structures, or characteristics of one or more embodiments in the present disclosure may be properly combined.

Each of the patents, patent applications, publications of patent applications, and other material, such as articles, books, specifications, publications, documents, things, and/or the like, referenced herein is hereby incorporated herein by this reference in its entirety for all purposes. History application documents that are inconsistent or conflictive with the contents of the present disclosure are excluded, as well as documents (currently or subsequently appended to the present specification) limiting the broadest scope of the claims of the present disclosure. By way of example, should there be any inconsistency or conflict between the description, definition, and/or the use of a term associated with any of the incorporated material and that associated with the present document, the description, definition, and/or the use of the term in the present document shall prevail.

In closing, it is to be understood that the embodiments of the present disclosure disclosed herein are illustrative of the principles of the embodiments of the present disclosure. Other modifications that may be employed may be within the scope of the present disclosure. Thus, by way of example, but not of limitation, alternative configurations of the embodiments of the present disclosure may be utilized in accordance with the teachings herein. Accordingly, embodiments of the present disclosure are not limited to that precisely as shown and described.

What is claimed is:

1. A clip apparatus, comprising:
a conveying device, wherein the conveying device includes a sheath pipe provided with a passage and a core shaft extending axially within the passage of the sheath pipe; and
at least two clip devices, wherein the at least two clip devices include a first clip device and a second clip device, the first clip device and the second clip device respectively include at least one clipping portion, the clipping portions include a first clipping portion provided in the first clip device and a second clipping portion provided in the second clip device, the clipping portions are provided outside the passage of the sheath pipe, the at least two clip devices are releasably connected in sequence, and proximal ends of the at least two clip devices are releasably connected to the sheath pipe.

2. The clip apparatus of claim 1, wherein a total length of the at least two clip devices when connected to each other is less than a sum of a length of each of the at least two clip devices.

3. The clip apparatus of claim 1, wherein the at least two clip devices further include an extension portion, a proximal end of the extension portion is connected to the core shaft, and a distal end of the extension portion is switchably connected to one of the clipping portions.

4. The clip apparatus of claim 3, wherein the extension portion and the first clipping portion form the first clip device when the extension portion is connected to the first clipping portion, and the extension portion and the second clipping portion form the second clip device when the extension portion is connected to the second clipping portion.

5. The clip apparatus of claim 3, wherein the clip device further includes at least one bonding member configured to releasably connect at least one of the clipping portions to the extension portion; and
the at least one bonding member includes a first bonding portion and a second bonding portion, the distal end of the extension portion includes a first docking portion, the at least one of the clipping portions includes a second docking portion, the first bonding portion is releasably connected to the first docking portion, and the second bonding portion mates with the second docking portion.

6. The clip apparatus of claim 1, further comprising a connecting member, wherein at least one of the clipping portions is releasably connected to at least one of the rest of the clipping portions through the connecting member; and/or the at least one of the clipping portions is releasably connected to the sheath pipe through the connecting member.

7. The clip apparatus of claim 6, wherein the connecting member includes a first connecting portion and a second connecting portion, a proximal end of the at least one of the clipping portions includes a first mating portion, and a distal end of the at least one of the rest of the clipping portions and/or a distal end of the sheath pipe includes a second mating portion, wherein the first connecting portion mates with the first mating portion and the second connecting portion mates with the second mating portion to achieve a connection between two of the clipping portions, and/or a connection between the clipping portions and the sheath pipe; and a release of the mating of the first connecting portion and the first mating portion and a release of the mating of the second connecting portion and the second mating portion achieve a release of the connection between the two of the clipping portions and/or a release of the connection between the clipping portions and the sheath pipe.

8. The clip apparatus of claim 7, wherein the first connecting portion includes a tongue piece, the tongue piece is provided on a distal end of the connecting member, the tongue piece is resilient, and the first mating portion includes a stop surface, wherein the tongue piece mates with the stop surface to make the first connecting portion mate with the first mating portion; and a release of the mating of the tongue piece and the stop surface achieves a release of the mating of the first connecting and the first mating portion.

9. The clip apparatus of claim 7, wherein the first connecting portion includes a snap hook, and the first mating portion includes a limit column, wherein the snap hook mates with the limit column to make the first connecting portion mate with the first mating portion; and deformation, fracture, or displacement of the snap hook by a force achieves a release of the mating of the snap hook and the limit column, so as to achieve a release of the mating of the first connecting portion and the first mating portion.

10. The clip apparatus of claim 7, the connecting member including a tab, wherein the tab is constructed as a resilient arch, one end of the tab is connected to a distal end of the connecting member, another end of the tab is formed toward a proximal end of the connecting member as a free end, and an outer arched surface of the tab is constructed as the second connecting portion;

the second mating portion includes a limit surface;

the outer arched surface of the tab mates with the limit surface to make the second connecting portion mate with the second mating portion; and a release of the mating of the outer arched surface of the tab and the limit surface achieves a release of the mating of the second connecting portion and the second mating portion.

11. The clip apparatus of claim 7, wherein the connecting member includes a third connecting portion, the third connecting portion and the second connecting portion are integrally molded, and the second connecting portion is deformed or displaced to form the third connecting portion.

12. The clip apparatus of claim 6, wherein the connecting member includes a third connecting portion, and when the third connecting portion is subjected to a force to satisfy a preset condition, the connecting member achieves a release of a connection between the at least one of the clipping portions and the at least one of the rest of the clipping portions, and/or the connecting member achieves a release of a connection between the at least one of the clipping portions and the sheath pipe.

13. The clip apparatus of claim 1, wherein the clipping portions are provided with a first snap portion, an extension portion is provided with a second snap portion, and the first snap portion and the second snap portion are releasably connected.

14. The clip apparatus of claim 1, wherein the clipping portions include a first clipping arm, a second clipping arm, and a locking portion, wherein the locking portion includes a first locking portion provided on the first clipping arm and a second locking portion provided on the second clipping arm; and the first locking portion includes a locking convexity, the second locking portion includes a locking concavity, the locking convexity mates with the locking concavity, and the first clipping arm locks with the second clipping arm.

15. The clip apparatus of claim 1, wherein the first clip device includes a first storage pipe, a proximal end of the first clipping portion is stored in the first storage pipe, the second clip device includes a second storage pipe, a proximal end of the second clipping portion is stored in the second storage pipe; and at least a portion of the second clipping portion mates with the first storage pipe in the first storage pipe when the first clip device is connected to the second clip device.

16. The clip apparatus of claim 15, wherein the second clipping portion is provided with a first outer connecting portion, the first storage pipe is provided with a first outer connecting hole, and the first outer connecting portion releasably mates with the first outer connecting hole.

17. The clip apparatus of claim 16, wherein the core shaft includes a spacer portion;

when the spacer portion is combined with the second clipping portion, the first outer connecting portion moves radially outward into the first outer connecting hole, and the second clipping portion is connected with the first storage pipe; and when the spacer portion is not combined with the second clipping portion, the first outer connecting portion moves radially inward until being separated from the first outer connecting hole, and the second clipping portion is released from the first storage pipe.

18. The clip apparatus of claim 15, wherein the conveying device further includes a bushing, a proximal end of the bushing is fixedly connected to a distal end of the sheath pipe, the bushing is provided with a second outer connecting portion, the second storage pipe is provided with a second outer connecting hole, and the second outer connecting portion releasably mates with the second outer connecting hole.

19. The clip apparatus of claim 15, wherein the clipping portions include a first clipping arm and a second clipping arm, and a proximal end of the first clipping arm and a proximal end of the second clipping arm are respectively provided with an inner connecting hole;

a distal end of the core shaft is provided with a connecting head, the connecting head includes a large diameter portion and a small diameter portion, the large diameter portion passes through the inner connecting hole of the first clipping arm and the inner connecting hole of the second clipping arm, respectively, and the small diameter portion snaps into the inner connecting hole of the first clipping arm and the inner connecting hole of the second clipping arm; and the connecting head is subjected to a force from a distal end to a proximal end such that the proximal end of the first clipping arm and the proximal end of the second clipping arm are deformed or displaced, the connecting head is withdrawn from the inner connecting holes of the first clipping arm and the second clipping arm, and the core shaft and the clipping portion are separated.

* * * * *